(12) United States Patent
Milo et al.

(10) Patent No.: US 9,719,122 B2
(45) Date of Patent: Aug. 1, 2017

(54) METHODS OF PRODUCTION OF PRODUCTS OF METABOLIC PATHWAYS

(71) Applicant: Yeda Research and Development Co. Ltd., Rehovot (IL)

(72) Inventors: Ron Milo, Kfar-Saba (IL); Lior Zelcbuch, Rehovot (IL); Niv Antonovsky, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/415,612

(22) PCT Filed: Jul. 17, 2013

(86) PCT No.: PCT/IL2013/050606
§ 371 (c)(1),
(2) Date: Jan. 19, 2015

(87) PCT Pub. No.: WO2014/013489
PCT Pub. Date: Jan. 23, 2014

(65) Prior Publication Data
US 2015/0211040 A1    Jul. 30, 2015

Related U.S. Application Data

(60) Provisional application No. 61/672,796, filed on Jul. 18, 2012.

(51) Int. Cl.
| C12P 23/00 | (2006.01) |
| C12N 15/52 | (2006.01) |
| C12N 15/70 | (2006.01) |
| C12N 9/02  | (2006.01) |
| C12N 9/10  | (2006.01) |
| C12N 9/90  | (2006.01) |
| C12N 15/67 | (2006.01) |

(52) U.S. Cl.
CPC .............. *C12P 23/00* (2013.01); *C12N 9/001* (2013.01); *C12N 9/0004* (2013.01); *C12N 9/0073* (2013.01); *C12N 9/1085* (2013.01); *C12N 9/90* (2013.01); *C12N 15/52* (2013.01); *C12N 15/70* (2013.01); *C12N 15/67* (2013.01); *C12Y 114/13129* (2013.01); *C12Y 205/01* (2013.01); *C12Y 205/01029* (2013.01); *C12Y 505/01019* (2013.01)

(58) Field of Classification Search
CPC ..................................................... C12P 23/00
See application file for complete search history.

(56) References Cited

U.S. PATENT DOCUMENTS

| 2006/0141558 A1 | 6/2006 | Tang et al. |
| 2012/0015849 A1 | 1/2012 | Soucaille et al. |

FOREIGN PATENT DOCUMENTS

| WO | WO 2006/096392 | 9/2006 |
| WO | WO 2008/008256 | 1/2008 |
| WO | WO 2014/013489 | 1/2014 |

OTHER PUBLICATIONS

T. Ide et al. "Enhanced production of astaxanthin in *Paracoccus* sp. strain N-81106 by using random mutagenesis and genetic engineering", Biochemical Engineering Journal 65:37-43 (Apr. 2012).*
M.A. Scaife et al. Characterization of Cyanobacterial b-Carotene Ketolase and Hydroxylase Genes in *Escherichia coli*, and Their Application for Astaxanthin Biosynthesis, Biotechnol. Bioeng. 103(5): 944-855 (2009).*
Supplementary European Search Report and the European Search Opinion Dated Mar. 2, 2016 From the European Patent Office Re. Application No. 13820518.2.
Wang et al. "Programming Cells by Multiplex Genome Engineering and Accelerated Evolution", Nature, XP055111854, 460(7257): 894-898, Aug. 13, 2009. Abstract, p. 896, Fig.5.
Notification of Office Action and Search Report Dated Feb. 15, 2016 From the State Intellectual Property Office of the People's Republic of China Re. Application No. 201380037848.5 and Its Translation of Office Action in English.
International Preliminary Report on Patentability Dated Jan. 29, 2015 From the International Bureau of WIPO Re. Application No. PCT/IL2013/050606.
International Search Report and the Written Opinion Dated Oct. 20, 2013 From the International Searching Authority Re. Application No. PCT/IL2013/050606.
Lemuth et al. "Engineering of a Plasmid-Free *Escherichia coli* Strain for Improved In Vivo Biosynthesis of Astaxanthin", Microbial Cell Factories, 10(29): 1-12, Apr. 26, 2011.
Levin-Karp et al. Quantifying Translational Coupling in *E. coli* Synthetic Operons Using RBS Modulation and Fluorescent Reporters, ACS Synthetic Biology, 2(6): 327-336, Apr. 16, 2013. Abstract.
Pfleger et al. "Combinatorial Engineering of Intergenic Regions to Tune Expression of Multiple Genes in Operons", Nature Biotechnology, 24(8): 1027-1032, Jul. 16, 2006.
Salis et al. "Automated Design of Synthetic Ribosome Binding Sites to Control Protein Expression", Nature Biotechnology, 27(10): 946-952, Oct. 4, 2009.

(Continued)

*Primary Examiner* — Rebecca Prouty

(57) ABSTRACT

A plurality of isolated polynucleotide sequences encoding enzymes of the astaxanthin pathway is disclosed. The polynucleotides include:
(i) a polynucleotide which encodes Phytoene dehydrogenase (crtI) and a first transcriptional regulatory sequence;
(ii) a polynucleotide which encodes Beta-lycopene cyclase (lcy-B) and a second transcriptional regulatory sequence;
(iii) a polynucleotide which encodes Beta-carotene ketolase (crtW) and a third transcriptional regulatory sequence; and
wherein the first, second and third regulatory sequence are selected such that the expression of the lcy-B and the crtW is greater than a level of expression of the crtI. Methods of generating astaxanthin using the plurality of polynucleotide are also disclosed as well as bacterial cells comprising high levels of astaxanthin.

10 Claims, 20 Drawing Sheets
(20 of 20 Drawing Sheet(s) Filed in Color)

(56) References Cited

OTHER PUBLICATIONS

Zelcbuch et al. "Spanning High-Dimensional Expression Space Using Ribosome-Binding Site Cominatorics", Nucelic Acids Research, 41(9): e98-1-e98-8, Mar. 6, 2013.
Notification of Office Action Dated Aug. 26, 2016 From the State Intellectual Property Office of the People's Republic of China Re. Application No. 201380037848.5 and Its Translation Into English.
Notice of Reasons for Rejection Dated Feb. 28, 2017 From the Japan Patent Office Re. Application No. 2015-522250. (5 Pages).
Translation of Notice of Reasons for Rejection Dated Feb. 28, 2017 From the Japan Patent Office Re. Application No. 2015-522250. (11 Pages).

* cited by examiner

SEQUENCE LISTING

```
<160> NUMBER OF SEQ ID NOS: 103

<210> SEQ ID NO 1
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 1
gctagcgttg atcgggcacg taagag                                          26

<210> SEQ ID NO 2
<211> LENGTH: 12
<212> TYPE: DNA
<213> ORGANISM: Artificial sequence
<220> FEATURE:
<223> OTHER INFORMATION: Ribosome Binding Site A (RBS-A)

<400> SEQUENCE: 2
aggaggtttg ga                                                         12

<210> SEQ ID NO 3
<211> LENGTH: 22
<212> TYPE: DNA
<213> ORGANISM: Artificial sequence
<220> FEATURE:
<223> OTHER INFORMATION: Ribosome Binding Site B (RBS-B)

<400> SEQUENCE: 3
aacaaaatga ggaggtactg ag                                              22

<210> SEQ ID NO 4
<211> LENGTH: 16
<212> TYPE: DNA
<213> ORGANISM: Artificial sequence
<220> FEATURE:
<223> OTHER INFORMATION: Ribosome Binding Site C (RBS-C)

<400> SEQUENCE: 4
aagttaagag gcaaga                                                     16

<210> SEQ ID NO 5
<211> LENGTH: 14
<212> TYPE: DNA
<213> ORGANISM: Artificial sequence
<220> FEATURE:
<223> OTHER INFORMATION: Ribosome Binding Site D (RBS-D)

<400> SEQUENCE: 5
ttcgcagggg gaag                                                       14

<210> SEQ ID NO 6
<211> LENGTH: 18
<212> TYPE: DNA
```

```
<213> ORGANISM: Artificial sequence
<220> FEATURE:
<223> OTHER INFORMATION: Ribosome Binding Site E (RBS-E)

<400> SEQUENCE: 6
taagcaggac cggcggcg                                                    18

<210> SEQ ID NO 7
<211> LENGTH: 12
<212> TYPE: DNA
<213> ORGANISM: Artificial sequence
<220> FEATURE:
<223> OTHER INFORMATION: "Dead-RBS" (RBS-F)

<400> SEQUENCE: 7
caccatacac tg                                                          12

<210> SEQ ID NO 8
<211> LENGTH: 27
<212> TYPE: DNA
<213> ORGANISM: Artificial sequence
<220> FEATURE:
<223> OTHER INFORMATION: Upstream insulator sequence

<400> SEQUENCE: 8
taatagaaat aattttgttt aacttta                                          27

<210> SEQ ID NO 9
<211> LENGTH: 21
<212> TYPE: DNA
<213> ORGANISM: Artificial sequence
<220> FEATURE:
<223> OTHER INFORMATION: A downstream insulator sequence

<400> SEQUENCE: 9
atgcatcatc accatcacca c                                                21

<210> SEQ ID NO 10
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 10
gaattcgcgg ccgcactagt taatagaaat aattttgttt aacttta                    47

<210> SEQ ID NO 11
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 11
gatggtgatg atgcattcca aacctcctta aagttaaaca aaat                       44

<210> SEQ ID NO 12
<211> LENGTH: 54
<212> TYPE: DNA
<213> ORGANISM: Artificial sequence
<220> FEATURE:
<223> OTHER INFORMATION: Single strand DNA oligonucleotide

<400> SEQUENCE: 12
gatggtgatg atgcatctca gtacctcctc attttgttta aagttaaaca aaat            54
```

<210> SEQ ID NO 13
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 13
gatggtgatg atgcattctt gcctcttaac tttaaagtta aacaaaat        48

<210> SEQ ID NO 14
<211> LENGTH: 50
<212> TYPE: DNA
<213> ORGANISM: Artificial sequence
<220> FEATURE:
<223> OTHER INFORMATION: Single strand DNA oligonucleotide

<400> SEQUENCE: 14
gatggtgatg atgcatcgcc gccggtcctg cttataaagt taaacaaaat        50

<210> SEQ ID NO 15
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 15
gatggtgatg atgcatcttc cccctgcgaa taaagttaaa caaaat        46

<210> SEQ ID NO 16
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 16
gatggtgatg atgcatcagt gtatggtgta aagttaaaca aaat        44

<210> SEQ ID NO 17
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 17
gctagcgttg atcgggcacg taagag        26

<210> SEQ ID NO 18
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 18
ggccacatgt ctgcagcggc cgcgctagc        29

<210> SEQ ID NO 19
<211> LENGTH: 30
<212> TYPE: DNA
<213> ORGANISM: Artificial sequence
<220> FEATURE:

<223> OTHER INFORMATION: Single strand DNA oligonucleotide

<400> SEQUENCE: 19
gcgctcgagc ggccgcgcta gcttattacg                              30

<210> SEQ ID NO 20
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 20
gctagcgttg atcgggcacg taagag                                  26

<210> SEQ ID NO 21
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 21
gcggccgcct gcagggcggt aatacggtta tcca                         34

<210> SEQ ID NO 22
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 22
ctctcgctta gtagttagac gtccgacgtt ggagtccacg ttct              44

<210> SEQ ID NO 23
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 23
agaacgtgga ctccaacgtc ggacgtctaa ctactaagcg agag              44

<210> SEQ ID NO 24
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 24
actagtgaat tcgcaacgaa caggtcacta tc                           32

<210> SEQ ID NO 25
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 25
ctcgagaaag tcgacctgca ggcagggcgg taatacggtt a                 41

<210> SEQ ID NO 26
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 26
ctcgaggagg tcgacctgca ggcagggcgg taatacggtt a        41

<210> SEQ ID NO 27
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 27
ctcgagtatg tcgacctgca ggcagggcgg taatacggtt a        41

<210> SEQ ID NO 28
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 28
ctcgagcacg tcgacctgca ggcagggcgg taatacggtt a        41

<210> SEQ ID NO 29
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 29
ctcgagaggg tcgacctgca ggcagggcgg taatacggtt a        41

<210> SEQ ID NO 30
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 30
ctcgagggtg tcgacctgca ggcagggcgg taatacggtt a        41

<210> SEQ ID NO 31
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 31
ttacttgtac agctcgtcca tgc        23

<210> SEQ ID NO 32
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 32
atgcatcatc accatcacca cgtgagcaag ggcgaggag            39

<210> SEQ ID NO 33
<211> LENGTH: 49
<212> TYPE: DNA
<213> ORGANISM: Artificial sequence
<220> FEATURE:
<223> OTHER INFORMATION: Single strand DNA oligonucleotide

<400> SEQUENCE: 33
ctcttacgtg cccgatcaac gctagcttac ttgtacagct cgtccatgc            49

<210> SEQ ID NO 34
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 34
ccaggactcc tccctgcaag acggcgagtt            30

<210> SEQ ID NO 35
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 35
aactcgccgt cttgcaggga ggagtcctgg            30

<210> SEQ ID NO 36
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 36
atgcatcatc accatcacca ccttcgttcg ttgctcagag g            41

<210> SEQ ID NO 37
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 37
atcacatcaa cgaagcgtga gctagcgttg atcgggcacg taagag            46

<210> SEQ ID NO 38
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 38
cacaagttcc taccacatca gcccgcaggc c            31

<210> SEQ ID NO 39
<211> LENGTH: 31

```
<212> TYPE: DNA
<213> ORGANISM: Artificial sequence
<220> FEATURE:
<223> OTHER INFORMATION: Single strand DNA oligonucleotide

<400> SEQUENCE: 39
ggcctgcggg ctgatgtggt aggaacttgt g                                  31

<210> SEQ ID NO 40
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 40
gtggacgaac acctgctgta gccacccttt                                    30

<210> SEQ ID NO 41
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 41
aaagggtggc tacagcaggt gttcgtccac                                    30

<210> SEQ ID NO 42
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 42
atgcatcatc accatcacca ctatccgttt ataaggacag cc                      42

<210> SEQ ID NO 43
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 43
ctcttacgtg cccgatcaac gctagcttaa ctgacggcag cgagt                   45

<210> SEQ ID NO 44
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 44
atgcatcatc accatcacca caataatccg tcgttactca a                       41

<210> SEQ ID NO 45
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 45
```
ctcttacgtg cccgatcaac gctagcttat gccggtactg ccgggc          46

<210> SEQ ID NO 46
<211> LENGTH: 42
<212> TYPE: DNA
<213> ORGANISM: Artificial sequence
<220> FEATURE:
<223> OTHER INFORMATION: Single strand DNA oligonucleotide

<400> SEQUENCE: 46
atgcatcatc accatcacca caaaccaact acggtaattg gt               42

<210> SEQ ID NO 47
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 47
ctcttacgtg cccgatcaac gctagctcat atcagatcct ccagca          46

<210> SEQ ID NO 48
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 48
gcacctcaac tggcgaaact tcaggcatgg a                          31

<210> SEQ ID NO 49
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 49
tccatgcctg aagtttcgcc agttgaggtg c                          31

<210> SEQ ID NO 50
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 50
cggttaagca gtccaacaaa cttcagacta a                          31

<210> SEQ ID NO 51
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 51
ttagtctgaa gtttgttgga ctgcttaacc g                          31

<210> SEQ ID NO 52
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 52
atgcatcatc accatcacca cgatactttg ttgaaaaccc c        41

<210> SEQ ID NO 53
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 53
ctcttacgtg cccgatcaac gctagctcat tctttatcct gtaacaaatt g        51

<210> SEQ ID NO 54
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 54
gctgtggttg gtggtggccc tgcgggactt        30

<210> SEQ ID NO 55
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 55
aagtcccgca gggccaccac caaccacagc        30

<210> SEQ ID NO 56
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 56
caagaaggtt ctttgatgcg ttctttgact        30

<210> SEQ ID NO 57
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 57
agtcaaagaa cgcatcaaag aaccttcttg        30

<210> SEQ ID NO 58
<211> LENGTH: 41
<212> TYPE: DNA
<213> ORGANISM: Artificial sequence
<220> FEATURE:
<223> OTHER INFORMATION: Single strand DNA oligonucleotide

<400> SEQUENCE: 58
atgcatcatc accatcacca cgttcagtgt caaccatcat c        41

<210> SEQ ID NO 59
<211> LENGTH: 53
<212> TYPE: DNA
<213> ORGANISM: Artificial sequence
<220> FEATURE:
<223> OTHER INFORMATION: Single strand DNA oligonucleotide

<400> SEQUENCE: 59
ctcttacgtg cccgatcaac gctagcttat aaagatattt tgtgagcttc agg    53

<210> SEQ ID NO 60
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 60
atgcatcatc accatcacca cttgtggatt tggaatgccc    40

<210> SEQ ID NO 61
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 61
ctcttacgtg cccgatcaac gctagcttat tacttcccgg atgcggg    47

<210> SEQ ID NO 62
<211> LENGTH: 302
<212> TYPE: PRT
<213> ORGANISM: Pantoea agglomerans

<400> SEQUENCE: 62

Met Thr Val Cys Ala Lys Lys His Val His Pro Thr Arg Ser Ala Ala
1               5                   10                  15

Glu Gln Leu Leu Ala Asp Ile Asp Arg Arg Leu Glu Gln Leu Leu Pro
            20                  25                  30

Val Glu Gly Glu Arg Asp Phe Val Gly Ala Ala Met Arg Glu Gly Ala
        35                  40                  45

Leu Ala Pro Gly Lys Arg Ile Arg Pro Met Leu Leu Leu Thr Ala
    50                  55                  60

Arg Asp Leu Gly Cys Ala Val Ser His Glu Gly Leu Leu Asp Ile Ala
65                  70                  75                  80

Cys Ala Val Glu Met Val His Ala Ala Ser Leu Ile Leu Asp Asp Met
                85                  90                  95

Pro Cys Met Asp Asp Ala Gln Ile Val Gly Gly Arg Pro Thr Val His
            100                 105                 110

Cys Gln Tyr Gly Glu His Val Ala Ile Leu Ala Ala Val Ala Leu Leu
        115                 120                 125

Ser Lys Ala Phe Gly Val Ile Ala Asp Ala Asp Gly Leu Thr Ala Leu
    130                 135                 140

Ala Lys Asn Arg Ala Val Ser Glu Leu Ser Asn Ala Ile Gly Met Gln
145                 150                 155                 160

Gly Leu Val Gln Gly Gln Phe Lys Asp Leu Ser Glu Gly Asp Lys Arg
                165                 170                 175

Arg Ser Ala Glu Ala Ile Leu Met Thr Asn His Phe Lys Thr Ser Thr
            180                 185                 190

```
Leu Phe Cys Ala Ser Met Gln Met Ala Ser Ile Val Ala Asn Ala Ser
            195                 200                 205

Ser Glu Arg Arg Asp Tyr Leu His Arg Phe Ser Leu Asp Leu Gly Gln
210                 215                 220

Ala Phe Gln Leu Leu Asp Asp Leu Thr Asp Gly Met Ala Asp Thr Gly
225                 230                 235                 240

Lys Asp Ile Asn Gln Asp Glu Gly Lys Ser Thr Leu Val Asn Leu Leu
                245                 250                 255

Gly Ser Arg Ala Val Glu Arg Leu Arg His Ser Leu His Leu Ala
                260                 265                 270

Ser Glu His Leu Ser Ala Ala Cys Gln Asn Gly His Ser Thr Gln Gln
                275                 280                 285

Phe Ile Gln Ala Trp Phe Asp Lys Lys Leu Ala Ala Val Ser
                290                 295                 300

<210> SEQ ID NO 63
<211> LENGTH: 296
<212> TYPE: PRT
<213> ORGANISM: Pantoea agglomerans

<400> SEQUENCE: 63

Met Ala Val Gly Ser Lys Ser Phe Ala Thr Ala Ser Lys Leu Phe Asp
1               5                   10                  15

Ala Lys Thr Arg Arg Ser Val Leu Met Leu Tyr Ser Trp Cys Arg His
                20                  25                  30

Cys Asp Asp Val Ile Asp Asp Gln Thr Leu Gly Phe Gln Thr Asp Gln
            35                  40                  45

Pro Ser Leu Gln Thr Pro Glu Gln Arg Leu Met Gln Leu Glu Met Lys
        50                  55                  60

Thr Arg Gln Ala Tyr Ala Gly Ser Gln Met His Glu Pro Ala Phe Ala
65                  70                  75                  80

Ala Phe Gln Glu Val Ala Met Ala His Asp Ile Ala Pro Ala Tyr Ala
                85                  90                  95

Phe Asp His Leu Glu Gly Phe Ala Met Asp Val Arg Glu Ala Glu Tyr
                100                 105                 110

Ile Gln Leu Asp Asp Thr Leu Arg Tyr Cys Tyr His Val Ala Gly Val
                115                 120                 125

Val Gly Leu Met Met Ala Gln Ile Met Gly Val Arg Asp Asn Ala Thr
            130                 135                 140

Leu Asp Arg Ala Cys Asp Leu Gly Leu Ala Phe Gln Leu Thr Asn Ile
145                 150                 155                 160

Ala Arg Asp Ile Val Glu Asp Ala His Val Gly Arg Cys Tyr Leu Pro
                165                 170                 175

Ala Ser Trp Leu Glu Asn Glu Gly Leu Asn Lys Glu Asn Tyr Ala Ala
                180                 185                 190

Pro Glu Asn Arg Gln Ala Leu Ser Arg Ile Ala Arg Arg Leu Val Gln
                195                 200                 205

Glu Ala Glu Pro Tyr Tyr Leu Cys Ala Thr Ala Gly Leu Ala Gly Leu
            210                 215                 220

Pro Leu Arg Ser Ala Trp Ala Ile Ala Thr Ala Lys Gln Val Tyr Arg
225                 230                 235                 240

Lys Ile Gly Val Lys Val Glu Gln Ala Gly Thr Glu Ala Trp Asp His
                245                 250                 255

Arg Gln Ser Thr Thr Thr Pro Glu Lys Leu Ser Leu Leu Leu Met Ala
```

```
            260                 265                 270
Ser Gly Gln Ala Ile Thr Ser Arg Met Arg Pro His Pro Pro Arg Pro
            275                 280                 285

Ala His Leu Trp Gln Arg Pro Ile
        290             295

<210> SEQ ID NO 64
<211> LENGTH: 492
<212> TYPE: PRT
<213> ORGANISM: Pantoea agglomerans

<400> SEQUENCE: 64

Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
            20                  25                  30

Arg Asp Lys Pro Gly Gly Arg Ala Tyr Val Tyr Glu Asp Gln Gly Phe
        35                  40                  45

Thr Phe Asp Ala Gly Pro Thr Val Ile Thr Asp Pro Ser Ala Ile Glu
    50                  55                  60

Glu Leu Phe Thr Leu Ala Gly Lys Gln Leu Lys Asp Tyr Val Glu Leu
65                  70                  75                  80

Leu Pro Val Ala Pro Phe Tyr Arg Leu Cys Trp Glu Ser Gly Lys Val
                85                  90                  95

Phe Asn Tyr Asp Asn Asp Gln Ala Gln Leu Glu Ala Gln Ile Gln Gln
            100                 105                 110

Phe Asn Pro Arg Asp Val Glu Gly Tyr Arg Gln Phe Leu Asp Tyr Ser
        115                 120                 125

Arg Ala Val Phe Lys Glu Gly Tyr Leu Lys Leu Gly Thr Val Pro Phe
    130                 135                 140

Leu Ser Phe Arg Asp Met Leu Arg Ala Ala Pro Gln Leu Ala Lys Leu
145                 150                 155                 160

Gln Ala Trp Arg Thr Val Tyr Ser Lys Val Ala Ser Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220

Lys Gly Met Ile Lys Leu Phe Gln Asp Leu Gly Gly Glu Val Val Leu
225                 230                 235                 240

Asn Ala Lys Val Ser His Met Glu Thr Thr Gly Asp Thr Ile Glu Ala
                245                 250                 255

Val His Leu Glu Asp Gly Arg Arg Phe Pro Thr Arg Ala Val Ala Ser
            260                 265                 270

Asn Ala Asp Val Val His Thr Tyr Arg Asp Leu Leu Ser Gln His Pro
        275                 280                 285

Ala Ala Val Lys Gln Ser Lys Lys Leu Gln Thr Lys Arg Met Ser Asn
    290                 295                 300

Ser Leu Phe Val Leu Tyr Phe Gly Leu Asn His His Asp Gln Leu
305                 310                 315                 320

Ala His His Thr Val Cys Phe Gly Pro Arg Tyr Arg Glu Leu Ile His
                325                 330                 335
```

```
Glu Ile Phe Asn His Asp Gly Leu Ala Asp Asp Phe Ser Leu Tyr Leu
                340                 345                 350

His Ala Pro Cys Val Thr Asp Ser Ser Leu Ala Pro Glu Gly Cys Gly
            355                 360                 365

Ser Tyr Tyr Val Leu Ala Pro Val Pro His Leu Gly Thr Ala Asn Leu
        370                 375                 380

Asp Trp Thr Val Glu Gly Pro Arg Leu Arg Asp Arg Ile Phe Glu Tyr
385                 390                 395                 400

Leu Glu Gln His Tyr Met Pro Gly Leu Arg Ser Gln Leu Val Thr Gln
                405                 410                 415

Arg Met Phe Thr Pro Phe Asp Phe Arg Asp Gln Leu Asn Ala Tyr Gln
            420                 425                 430

Gly Ser Ala Phe Ser Val Glu Pro Val Leu Thr Gln Ser Ala Trp Phe
        435                 440                 445

Arg Pro His Asn Arg Asp Lys Thr Ile Asn Asn Leu Tyr Leu Val Gly
    450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490

<210> SEQ ID NO 65
<211> LENGTH: 305
<212> TYPE: PRT
<213> ORGANISM: Haematococcus pluvialis

<400> SEQUENCE: 65

Met Leu Arg Ser Leu Leu Arg Gly Leu Thr His Ile Pro Arg Val Asn
1               5                   10                  15

Ser Ala Gln Gln Pro Ser Cys Ala His Ala Arg Leu Gln Phe Lys Leu
            20                  25                  30

Arg Ser Met Gln Met Thr Leu Met Gln Pro Ser Ile Ser Ala Asn Leu
        35                  40                  45

Ser Arg Ala Glu Asp Arg Thr Asp His Met Arg Gly Ala Ser Thr Trp
    50                  55                  60

Ala Gly Gly Gln Ser Gln Asp Glu Leu Met Leu Lys Asp Glu Cys Ile
65                  70                  75                  80

Leu Val Asp Val Glu Asp Asn Ile Thr Gly His Ala Ser Lys Leu Glu
                85                  90                  95

Cys His Lys Phe Leu Pro His Gln Pro Ala Gly Leu Leu His Arg Ala
            100                 105                 110

Phe Ser Val Phe Leu Phe Asp Asp Gln Gly Arg Leu Leu Leu Gln Gln
        115                 120                 125

Arg Ala Arg Ser Lys Ile Thr Phe Pro Ser Val Trp Thr Asn Thr Cys
    130                 135                 140

Cys Ser His Pro Leu His Gly Gln Thr Pro Asp Glu Val Asp Gln Leu
145                 150                 155                 160

Ser Gln Val Ala Asp Gly Thr Val Pro Gly Ala Lys Ala Ala Ile
                165                 170                 175

Arg Lys Leu Glu His Glu Leu Gly Ile Pro Ala His Gln Leu Pro Ala
            180                 185                 190

Ser Ala Phe Arg Phe Leu Thr Arg Leu His Tyr Cys Ala Ala Asp Val
        195                 200                 205

Gln Pro Ala Ala Thr Gln Ser Ala Leu Trp Gly Glu His Glu Met Asp
    210                 215                 220
```

```
Tyr Ile Leu Phe Ile Arg Ala Asn Val Thr Leu Ala Pro Asn Pro Asp
225                 230                 235                 240

Glu Val Asp Glu Val Arg Tyr Val Thr Gln Glu Leu Arg Gln Met
            245                 250                 255

Met Gln Pro Asp Asn Gly Leu Gln Trp Ser Pro Trp Phe Arg Ile Ile
            260                 265                 270

Ala Ala Arg Phe Leu Glu Arg Trp Ala Asp Leu Asp Ala Ala Leu
            275                 280                 285

Asn Thr Asp Lys His Glu Asp Trp Gly Thr Val His His Ile Asn Glu
            290                 295                 300

Ala
305

<210> SEQ ID NO 66
<211> LENGTH: 500
<212> TYPE: PRT
<213> ORGANISM: Lycopersicon esculentum

<400> SEQUENCE: 66

Met Asp Thr Leu Leu Lys Thr Pro Asn Asn Leu Glu Phe Leu Asn Pro
1               5                   10                  15

His His Gly Phe Ala Val Lys Ala Ser Thr Phe Arg Ser Glu Lys His
                20                  25                  30

His Asn Phe Gly Ser Arg Lys Phe Cys Glu Thr Leu Gly Arg Ser Val
            35                  40                  45

Cys Val Lys Gly Ser Ser Ser Ala Leu Leu Glu Leu Val Pro Glu Thr
50                  55                  60

Lys Lys Glu Asn Leu Asp Phe Glu Leu Pro Met Tyr Asp Pro Ser Lys
65                  70                  75                  80

Gly Val Val Val Asp Leu Ala Val Val Gly Gly Pro Ala Gly Leu
                85                  90                  95

Ala Val Ala Gln Gln Val Ser Glu Ala Gly Leu Ser Val Cys Ser Ile
                100                 105                 110

Asp Pro Asn Pro Lys Leu Ile Trp Pro Asn Asn Tyr Gly Val Trp Val
                115                 120                 125

Asp Glu Phe Glu Ala Met Asp Leu Leu Asp Cys Leu Asp Ala Thr Trp
            130                 135                 140

Ser Gly Ala Ala Val Tyr Ile Asp Asp Asn Thr Ala Lys Asp Leu His
145                 150                 155                 160

Arg Pro Tyr Gly Arg Val Asn Arg Lys Gln Leu Lys Ser Lys Met Met
                165                 170                 175

Gln Lys Cys Ile Met Asn Gly Val Lys Phe His Gln Ala Lys Val Ile
                180                 185                 190

Lys Val Ile His Glu Glu Ser Lys Ser Met Leu Ile Cys Asn Asp Gly
            195                 200                 205

Ile Thr Ile Gln Ala Thr Val Val Leu Asp Ala Thr Gly Phe Ser Arg
210                 215                 220

Ser Leu Val Gln Tyr Asp Lys Pro Tyr Asn Pro Gly Tyr Gln Val Ala
225                 230                 235                 240

Tyr Gly Ile Leu Ala Glu Val Glu Glu His Pro Phe Asp Val Asn Lys
                245                 250                 255

Met Val Phe Met Asp Trp Arg Asp Ser His Leu Lys Asn Asn Thr Asp
                260                 265                 270

Leu Lys Glu Arg Asn Ser Arg Ile Pro Thr Phe Leu Tyr Ala Met Pro
```

```
                275                 280                 285
Phe Ser Ser Asn Arg Ile Phe Leu Glu Glu Thr Ser Leu Val Ala Arg
290                 295                 300

Pro Gly Leu Arg Ile Asp Asp Ile Gln Glu Arg Met Val Ala Arg Leu
305                 310                 315                 320

Asn His Leu Gly Ile Lys Val Lys Ser Ile Glu Glu Asp Glu His Cys
                325                 330                 335

Leu Ile Pro Met Gly Gly Pro Leu Pro Val Leu Pro Gln Arg Val Val
                340                 345                 350

Gly Ile Gly Gly Thr Ala Gly Met Val His Pro Ser Thr Gly Tyr Met
                355                 360                 365

Val Ala Arg Thr Leu Ala Ala Ala Pro Val Val Ala Asn Ala Ile Ile
370                 375                 380

Gln Tyr Leu Gly Ser Glu Arg Ser His Ser Gly Asn Glu Leu Ser Thr
385                 390                 395                 400

Ala Val Trp Lys Asp Leu Trp Pro Ile Glu Arg Arg Gln Arg Glu
                405                 410                 415

Phe Phe Cys Phe Gly Met Asp Ile Leu Leu Lys Leu Asp Leu Pro Ala
                420                 425                 430

Thr Arg Arg Phe Phe Asp Ala Phe Asp Leu Glu Pro Arg Tyr Trp
                435                 440                 445

His Gly Phe Leu Ser Ser Arg Leu Phe Leu Pro Glu Leu Ile Val Phe
                450                 455                 460

Gly Leu Ser Leu Phe Ser His Ala Ser Asn Thr Ser Arg Phe Glu Ile
465                 470                 475                 480

Met Thr Lys Gly Thr Val Pro Leu Val Asn Met Ile Asn Asn Leu Leu
                485                 490                 495

Gln Asp Lys Glu
            500

<210> SEQ ID NO 67
<211> LENGTH: 175
<212> TYPE: PRT
<213> ORGANISM: Pantoea ananatis

<400> SEQUENCE: 67

Met Leu Trp Ile Trp Asn Ala Leu Ile Val Phe Val Thr Val Ile Gly
1               5                   10                  15

Met Glu Val Ile Ala Ala Leu Ala His Lys Tyr Ile Met His Gly Trp
                20                  25                  30

Gly Trp Gly Trp His Leu Ser His Glu Pro Arg Lys Gly Ala Phe
            35                  40                  45

Glu Val Asn Asp Leu Tyr Ala Val Val Phe Ala Ala Leu Ser Ile Leu
50                  55                  60

Leu Ile Tyr Leu Gly Ser Thr Gly Met Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
                100                 105                 110

Leu Lys Arg Leu Tyr Met Ala His Arg Met His His Ala Val Arg Gly
                115                 120                 125

Lys Glu Gly Cys Val Ser Phe Gly Phe Leu Tyr Ala Pro Pro Leu Ser
                130                 135                 140
```

```
Lys Leu Gln Ala Thr Leu Arg Glu Arg His Gly Ala Arg Ala Gly Ala
145                 150                 155                 160

Ala Arg Asp Ala Gln Gly Gly Glu Asp Glu Pro Ala Ser Gly Lys
                165                 170                 175

<210> SEQ ID NO 68
<211> LENGTH: 258
<212> TYPE: PRT
<213> ORGANISM: Nostoc sp. PCC 7120

<400> SEQUENCE: 68

Met Val Gln Cys Gln Pro Ser Ser Leu His Ser Glu Lys Leu Val Leu
1               5                   10                  15

Leu Ser Ser Thr Ile Arg Asp Asp Lys Asn Ile Asn Lys Gly Ile Phe
                20                  25                  30

Ile Ala Cys Phe Ile Leu Phe Leu Trp Ala Ile Ser Leu Ile Leu Leu
            35                  40                  45

Leu Ser Ile Asp Thr Ser Ile Ile His Lys Ser Leu Leu Gly Ile Ala
        50                  55                  60

Met Leu Trp Gln Thr Phe Leu Tyr Thr Gly Leu Phe Ile Thr Ala His
65                  70                  75                  80

Asp Ala Met His Gly Val Val Tyr Pro Lys Asn Pro Arg Ile Asn Asn
                85                  90                  95

Phe Ile Gly Lys Leu Thr Leu Ile Leu Tyr Gly Leu Leu Pro Tyr Lys
                100                 105                 110

Asp Leu Leu Lys Lys His Trp Leu His His Gly His Pro Gly Thr Asp
            115                 120                 125

Leu Asp Pro Asp Tyr Tyr Asn Gly His Pro Gln Asn Phe Phe Leu Trp
        130                 135                 140

Tyr Leu His Phe Met Lys Ser Tyr Trp Arg Trp Thr Gln Ile Phe Gly
145                 150                 155                 160

Leu Val Met Ile Phe His Gly Leu Lys Asn Leu Val His Ile Pro Glu
                165                 170                 175

Asn Asn Leu Ile Ile Phe Trp Met Ile Pro Ser Ile Leu Ser Ser Val
            180                 185                 190

Gln Leu Phe Tyr Phe Gly Thr Phe Leu Pro His Lys Lys Leu Glu Gly
        195                 200                 205

Gly Tyr Thr Asn Pro His Cys Ala Arg Ser Ile Pro Leu Pro Leu Phe
    210                 215                 220

Trp Ser Phe Val Thr Cys Tyr His Phe Gly Tyr His Lys Glu His His
225                 230                 235                 240

Glu Tyr Pro Gln Leu Pro Trp Trp Lys Leu Pro Glu Ala His Lys Ile
                245                 250                 255

Ser Leu

<210> SEQ ID NO 69
<211> LENGTH: 620
<212> TYPE: PRT
<213> ORGANISM: Escherichia coli

<400> SEQUENCE: 69

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
                20                  25                  30

Asp Glu Leu Arg Arg Tyr Leu Leu Asp Ser Val Ser Arg Ser Ser Gly
```

-continued

```
                35                  40                  45
    His Phe Ala Ser Gly Leu Gly Thr Val Glu Leu Thr Val Ala Leu His
    50                  55                  60
Tyr Val Tyr Asn Thr Pro Phe Asp Gln Leu Ile Trp Asp Val Gly His
65                  70                  75                  80
Gln Ala Tyr Pro His Lys Ile Leu Thr Gly Arg Arg Asp Lys Ile Gly
                85                  90                  95
Thr Ile Arg Gln Lys Gly Gly Leu His Pro Phe Pro Trp Arg Gly Glu
            100                 105                 110
Ser Glu Tyr Asp Val Leu Ser Val Gly His Ser Ser Thr Ser Ile Ser
            115                 120                 125
Ala Gly Ile Gly Ile Ala Val Ala Ala Glu Lys Glu Gly Lys Asn Arg
            130                 135                 140
Arg Thr Val Cys Val Ile Gly Asp Gly Ala Ile Thr Ala Gly Met Ala
145                 150                 155                 160
Phe Glu Ala Met Asn His Ala Gly Asp Ile Arg Pro Asp Met Leu Val
                165                 170                 175
Val Leu Asn Asp Asn Glu Met Ser Ile Ser Glu Asn Val Gly Ala Leu
            180                 185                 190
Asn Asn His Leu Ala Gln Leu Leu Ser Gly Lys Leu Tyr Ser Ser Leu
            195                 200                 205
Arg Glu Gly Gly Lys Lys Val Phe Ser Gly Val Pro Pro Ile Lys Glu
            210                 215                 220
Leu Leu Lys Arg Thr Glu Glu His Ile Lys Gly Met Val Val Pro Gly
225                 230                 235                 240
Thr Leu Phe Glu Glu Leu Gly Phe Asn Tyr Ile Gly Pro Val Asp Gly
                245                 250                 255
His Asp Val Leu Gly Leu Ile Thr Thr Leu Lys Asn Met Arg Asp Leu
            260                 265                 270
Lys Gly Pro Gln Phe Leu His Ile Met Thr Lys Lys Gly Arg Gly Tyr
            275                 280                 285
Glu Pro Ala Glu Lys Asp Pro Ile Thr Phe His Ala Val Pro Lys Phe
            290                 295                 300
Asp Pro Ser Ser Gly Cys Leu Pro Lys Ser Ser Gly Gly Leu Pro Ser
305                 310                 315                 320
Tyr Ser Lys Ile Phe Gly Asp Trp Leu Cys Glu Thr Ala Ala Lys Asp
                325                 330                 335
Asn Lys Leu Met Ala Ile Thr Pro Ala Met Arg Glu Gly Ser Gly Met
            340                 345                 350
Val Glu Phe Ser Arg Lys Phe Pro Asp Arg Tyr Phe Asp Val Ala Ile
            355                 360                 365
Ala Glu Gln His Ala Val Thr Phe Ala Ala Gly Leu Ala Ile Gly Gly
            370                 375                 380
Tyr Lys Pro Ile Val Ala Ile Tyr Ser Thr Phe Leu Gln Arg Ala Tyr
385                 390                 395                 400
Asp Gln Val Leu His Asp Val Ala Ile Gln Lys Leu Pro Val Leu Phe
                405                 410                 415
Ala Ile Asp Arg Ala Gly Ile Val Gly Ala Asp Gly Gln Thr His Gln
            420                 425                 430
Gly Ala Phe Asp Leu Ser Tyr Leu Arg Cys Ile Pro Glu Met Val Ile
            435                 440                 445
Met Thr Pro Ser Asp Glu Asn Glu Cys Arg Gln Met Leu Tyr Thr Gly
            450                 455                 460
```

Tyr His Tyr Asn Asp Gly Pro Ser Ala Val Arg Tyr Pro Arg Gly Asn
465                 470                 475                 480

Ala Val Gly Val Glu Leu Thr Pro Leu Glu Lys Leu Pro Ile Gly Lys
            485                 490                 495

Gly Ile Val Lys Arg Arg Gly Glu Lys Leu Ala Ile Leu Asn Phe Gly
        500                 505                 510

Thr Leu Met Pro Asp Ala Ala Lys Val Ala Glu Ser Leu Asn Ala Thr
    515                 520                 525

Leu Val Asp Met Arg Phe Val Lys Pro Leu Asp Glu Ala Leu Ile Leu
530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
            580                 585                 590

Pro Gln Gly Thr Gln Glu Met Arg Ala Glu Leu Gly Leu Asp Ala
        595                 600                 605

Ala Gly Met Glu Ala Lys Ile Lys Ala Trp Leu Ala
    610                 615                 620

<210> SEQ ID NO 70
<211> LENGTH: 6
<212> TYPE: RNA
<213> ORGANISM: Artificial sequence
<220> FEATURE:
<223> OTHER INFORMATION: Exemplary RBS sequence

<400> SEQUENCE: 70 aggaaa                                                                    6

<210> SEQ ID NO 71
<211> LENGTH: 6
<212> TYPE: RNA
<213> ORGANISM: Artificial sequence
<220> FEATURE:
<223> OTHER INFORMATION: Exemplary RBS sequence

<400> SEQUENCE: 71 agaaaa                                                                    6

<210> SEQ ID NO 72
<211> LENGTH: 6
<212> TYPE: RNA
<213> ORGANISM: Artificial sequence
<220> FEATURE:
<223> OTHER INFORMATION: Exemplary RBS sequence

<400> SEQUENCE: 72 agaaga                                                                    6

<210> SEQ ID NO 73
<211> LENGTH: 6
<212> TYPE: RNA
<213> ORGANISM: Artificial sequence
<220> FEATURE:
<223> OTHER INFORMATION: Exemplary RBS sequence

<400> SEQUENCE: 73 aggaga                                                                    6

```
<210> SEQ ID NO 74
<211> LENGTH: 10
<212> TYPE: RNA
<213> ORGANISM: Artificial sequence
<220> FEATURE:
<223> OTHER INFORMATION: Exemplary RBS sequence

<400> SEQUENCE: 74
aagaaggaaa                                                          10

<210> SEQ ID NO 75
<211> LENGTH: 8
<212> TYPE: RNA
<213> ORGANISM: Artificial sequence
<220> FEATURE:
<223> OTHER INFORMATION: Exemplary RBS sequence

<400> SEQUENCE: 75 aaggaaaa                                                             8

<210> SEQ ID NO 76
<211> LENGTH: 8
<212> TYPE: RNA
<213> ORGANISM: Artificial sequence
<220> FEATURE:
<223> OTHER INFORMATION: Exemplary RBS sequence

<400> SEQUENCE: 76 aaggaaag                                                             8

<210> SEQ ID NO 77
<211> LENGTH: 8
<212> TYPE: RNA
<213> ORGANISM: Artificial sequence
<220> FEATURE:
<223> OTHER INFORMATION: Exemplary RBS sequence

<400> SEQUENCE: 77 aaggaaau                                                             8

<210> SEQ ID NO 78
<211> LENGTH: 9
<212> TYPE: RNA
<213> ORGANISM: Artificial sequence
<220> FEATURE:
<223> OTHER INFORMATION: Exemplary RBS sequence

<400> SEQUENCE: 78 aaggaaaaa                                                            9

<210> SEQ ID NO 79
<211> LENGTH: 9
<212> TYPE: RNA
<213> ORGANISM: Artificial sequence
<220> FEATURE:
<223> OTHER INFORMATION: Exemplary RBS sequence

<400> SEQUENCE: 79 aaggaaaag                                                            9

<210> SEQ ID NO 80
<211> LENGTH: 9
<212> TYPE: RNA
<213> ORGANISM: Artificial sequence
<220> FEATURE:
<223> OTHER INFORMATION: Exemplary RBS sequence
```

```
<400> SEQUENCE: 80 aaggaaaau                                                              9

<210> SEQ ID NO 81
<211> LENGTH: 10
<212> TYPE: RNA
<213> ORGANISM: Artificial sequence
<220> FEATURE:
<223> OTHER INFORMATION: Exemplary RBS sequence

<400> SEQUENCE: 81
aaggaaaaaa                                                            10

<210> SEQ ID NO 82
<211> LENGTH: 10
<212> TYPE: RNA
<213> ORGANISM: Artificial sequence
<220> FEATURE:
<223> OTHER INFORMATION: Exemplary RBS sequence

<400> SEQUENCE: 82
aaggaaaaag                                                            10

<210> SEQ ID NO 83
<211> LENGTH: 10
<212> TYPE: RNA
<213> ORGANISM: Artificial sequence
<220> FEATURE:
<223> OTHER INFORMATION: Exemplary RBS sequence

<400> SEQUENCE: 83
aaggaaaaau                                                            10

<210> SEQ ID NO 84
<211> LENGTH: 11
<212> TYPE: RNA
<213> ORGANISM: Artificial sequence
<220> FEATURE:
<223> OTHER INFORMATION: Exemplary RBS sequence

<400> SEQUENCE: 84
aaggaaaaaa a                                                          11

<210> SEQ ID NO 85
<211> LENGTH: 11
<212> TYPE: RNA
<213> ORGANISM: Artificial sequence
<220> FEATURE:
<223> OTHER INFORMATION: Exemplary RBS sequence

<400> SEQUENCE: 85
aaggaaaaaa g                                                          11

<210> SEQ ID NO 86
<211> LENGTH: 11
<212> TYPE: RNA
<213> ORGANISM: Artificial sequence
<220> FEATURE:
<223> OTHER INFORMATION: Exemplary RBS sequence

<400> SEQUENCE: 86
aaggaaaaaa u                                                          11

<210> SEQ ID NO 87
```

```
<211> LENGTH: 12
<212> TYPE: RNA
<213> ORGANISM: Artificial sequence
<220> FEATURE:
<223> OTHER INFORMATION: Exemplary RBS sequence

<400> SEQUENCE: 87
aaggaaaaaa aa                                                              12

<210> SEQ ID NO 88
<211> LENGTH: 12
<212> TYPE: RNA
<213> ORGANISM: Artificial sequence
<220> FEATURE:
<223> OTHER INFORMATION: Exemplary RBS sequence

<400> SEQUENCE: 88
aaggaaaaaa ag                                                              12

<210> SEQ ID NO 89
<211> LENGTH: 12
<212> TYPE: RNA
<213> ORGANISM: Artificial sequence
<220> FEATURE:
<223> OTHER INFORMATION: Exemplary RBS sequence

<400> SEQUENCE: 89
aaggaaaaaa au                                                              12

<210> SEQ ID NO 90
<211> LENGTH: 13
<212> TYPE: RNA
<213> ORGANISM: Artificial sequence
<220> FEATURE:
<223> OTHER INFORMATION: Exemplary RBS sequence

<400> SEQUENCE: 90
aaggaaaaaa aaa                                                             13

<210> SEQ ID NO 91
<211> LENGTH: 13
<212> TYPE: RNA
<213> ORGANISM: Artificial sequence
<220> FEATURE:
<223> OTHER INFORMATION: Exemplary RBS sequence

<400> SEQUENCE: 91
aaggaaaaaa aag                                                             13

<210> SEQ ID NO 92
<211> LENGTH: 13
<212> TYPE: RNA
<213> ORGANISM: Artificial sequence
<220> FEATURE:
<223> OTHER INFORMATION: Exemplary RBS sequence

<400> SEQUENCE: 92
aaggaaaaaa aau                                                             13

<210> SEQ ID NO 93
<211> LENGTH: 14
<212> TYPE: RNA
<213> ORGANISM: Artificial sequence
<220> FEATURE:
<223> OTHER INFORMATION: Exemplary RBS sequence

<400> SEQUENCE: 93
```

```
aaggaaaaaa aaaa                                            14

<210> SEQ ID NO 94
<211> LENGTH: 14
<212> TYPE: RNA
<213> ORGANISM: Artificial sequence
<220> FEATURE:
<223> OTHER INFORMATION: Exemplary RBS sequence

<400> SEQUENCE: 94
aaggaaaaaa aaag                                            14

<210> SEQ ID NO 95
<211> LENGTH: 10
<212> TYPE: RNA
<213> ORGANISM: Artificial sequence
<220> FEATURE:
<223> OTHER INFORMATION: Exemplary RBS sequence

<400> SEQUENCE: 95
aaggaggaaa                                                 10

<210> SEQ ID NO 96
<211> LENGTH: 14
<212> TYPE: RNA
<213> ORGANISM: Artificial sequence
<220> FEATURE:
<223> OTHER INFORMATION: Exemplary RBS sequence

<400> SEQUENCE: 96
aaggaaaaaa aaau                                            14

<210> SEQ ID NO 97
<211> LENGTH: 33
<212> TYPE: DNA
<213> ORGANISM: Artificial sequence
<220> FEATURE:
<223> OTHER INFORMATION: Preferred mRNA stabilizing sequence

<400> SEQUENCE: 97
ggtcgagtta tctcgagtga gatattgttg acg                       33

<210> SEQ ID NO 98
<211> LENGTH: 33
<212> TYPE: DNA
<213> ORGANISM: Artificial sequence
<220> FEATURE:
<223> OTHER INFORMATION: Preferred mRNA stabilizing sequence

<400> SEQUENCE: 98
ggtggactta tctcgagtga gatattgttg acg                       33

<210> SEQ ID NO 99
<211> LENGTH: 33
<212> TYPE: DNA
<213> ORGANISM: Artificial sequence
<220> FEATURE:
<223> OTHER INFORMATION: Preferred mRNA stabilizing sequence

<400> SEQUENCE: 99
cctcgagtta tctcgagtga gatattgttg acg                       33

<210> SEQ ID NO 100
<211> LENGTH: 33
<212> TYPE: DNA
```

```
<213> ORGANISM: Artificial sequence
<220> FEATURE:
<223> OTHER INFORMATION: Preferred mRNA stabilizing sequence

<400> SEQUENCE: 100
gctcgagtta tctcgagtga gatattgttg acg                              33

<210> SEQ ID NO 101
<211> LENGTH: 33
<212> TYPE: DNA
<213> ORGANISM: Artificial sequence
<220> FEATURE:
<223> OTHER INFORMATION: Preferred mRNA stabilizing sequence

<400> SEQUENCE: 101
cgtcgagtta tctcgagtga gatattgttg acg                              33

<210> SEQ ID NO 102
<211> LENGTH: 33
<212> TYPE: DNA
<213> ORGANISM: Artificial sequence
<220> FEATURE:
<223> OTHER INFORMATION: Preferred mRNA stabilizing sequence

<400> SEQUENCE: 102
ggtggagtta tctcgagtga gatattgttg acg                              33

<210> SEQ ID NO 103
<211> LENGTH: 33
<212> TYPE: DNA
<213> ORGANISM: Artificial sequence
<220> FEATURE:
<223> OTHER INFORMATION: Preferred mRNA stabilizing sequence

<400> SEQUENCE: 103
gctggactta tctcgagtga gatattgttg acg                              33
```

METHODS OF PRODUCTION OF PRODUCTS OF METABOLIC PATHWAYS

RELATED APPLICATIONS

This application is a National Phase of PCT Patent Application No. PCT/IL2013/050606 having International filing date of Jul. 17, 2013, which claims the benefit of priority under 35 USC §119(e) of U.S. Provisional Patent Application No. 61/672,796 filed on Jul. 18, 2012. The contents of the above applications are all incorporated by reference as if fully set forth herein in their entirety.

SEQUENCE LISTING STATEMENT

The ASCII file, entitled 61011SequenceListing.txt, created on Dec. 3, 2014, comprising 45,281 bytes, submitted concurrently with the filing of this application is incorporated herein by reference.

FIELD AND BACKGROUND OF THE INVENTION

The present invention, in some embodiments thereof, relates to biotechnological methods for generation of products of metabolic pathways such as astaxanthin.

Native protein abundance in bacteria spans over five orders of magnitude. The balancing of protein expression levels is at the heart of proper functioning of natural biological systems and is often critical to metabolic engineering efforts. While the manipulation of intracellular protein levels, such as strong over and under-expression is widely used to elucidate the functions of biological systems, an ability to fine-tune the levels of many genes in parallel is a major outstanding challenge. In contrast to native biological systems, where the balancing of protein levels is selected for during evolution, the expression of a synthetic system can lead to imbalances in protein concentrations. As a result, synthetic pathways rarely function optimally when first introduced and the enzyme levels must be fine-tuned.

FIG. 15A schematically depicts the major challenges associated with imbalanced enzyme concentrations based on a two-step metabolic pathway model. First, low enzyme expression can limit the pathway flux and therefore product synthesis rate (blue region). At the other extreme, excessive expression might lead to protein burden, resulting in the depletion of cellular resources that limit growth (purple region). Finally, imbalances between enzymes producing and consuming an intermediate metabolite can result in a metabolic bottleneck and a high concentration of potentially toxic pathway intermediates (green region).

Approaches for controlling the intracellular abundance of proteins include altering the promoter K. Hammer, I. Mijakovic, P. R. Jensen, Synthetic promoter libraries—tuning of gene expression, Trends in Biotechnology 24, 53-55 (2006)] or the ribosome binding site (RBS) [H. M. Salis, E. A. Mirsky, C. A. Voigt, Automated design of synthetic ribosome binding sites to control protein expression, Nat Biotechnol 27, 946-950 (2009); H. H. Wang et al., Programming cells by multiplex genome engineering and accelerated evolution, Nature 460, 894-898 (2009)] sequences, modulating the stability of transcripts and varying the degradation rate of the mature protein.

Carotenoids, such as astaxanthin, are natural pigments that are responsible for many of the yellow, orange and red colors seen in living organisms. Carotenoids are widely distributed in nature and have, in various living systems, two main biological functions: they serve as light-harvesting pigments in photosynthesis, and they protect against photo oxidative damage.

Astaxanthin is the most expensive commercially used carotenoid compound (today's market value is greater than 3,500 $/kg). It is utilized mainly as nutritional supplement which provides pigmentation in a wide variety of aquatic animals. In the Far-East it is used also for feeding poultry to yield a typical pigmentation of chickens. It is also a desirable and effective nontoxic coloring for the food industry and is valuable in cosmetics. Recently it was reported that astaxanthin is a potent antioxidant in humans and thus is a desirable food additive.

Although astaxanthin is synthesized in a variety of bacteria, fungi and algae, the key limitation to the use of biological systems for its production is its low yield. One of the reasons for the low yield is the complexity of the astaxanthin pathway, whereby 7 genes of the pathway must be expressed in the cells for efficient expression. Fine tuning of the amount of expression of each of these genes is essential for optimizing astaxanthin expression.

Lemuth et al., [Microbial Cell Factories 10, 29, 2011] teaches expression of astaxanthin in *E. coli*.

Salis et al., Nature Biotechnology Volume 27, No. 10, pages 946-950, 2009 teaches sequences of ribosome binding sites.

U.S. Patent Application No. 20120015849 teaches a method of creating DNA libraries that include an artificial promoter library and/or a modified ribosome binding site library and transforming bacterial host cells with the library to obtain a population of bacterial clones having a range of expression levels for a chromosomal gene of interest.

SUMMARY OF THE INVENTION

According to an aspect of some embodiments of the present invention there is provided a plurality of isolated polynucleotide sequences encoding enzymes of the astaxanthin pathway comprising:
 (i) a polynucleotide which encodes Phytoene dehydrogenase (crtI) and a first transcriptional regulatory sequence;
 (ii) a polynucleotide which encodes Beta-lycopene cyclase (lcy-B) and a second transcriptional regulatory sequence;
 (iii) a polynucleotide which encodes Beta-carotene ketolase (crtW) and a third transcriptional regulatory sequence; and
 wherein the first, second and third regulatory sequence are selected such that the expression of the lcy-B and the crtW is greater than a level of expression of the crtI.

According to an aspect of some embodiments of the present invention there is provided a bacterial cell comprising more than 2 mg/g cell dry weight of astaxanthin.

According to an aspect of some embodiments of the present invention there is provided a bacterial cell comprising more than 5 mg/g cell dry weight of astaxanthin.

According to an aspect of some embodiments of the present invention there is provided a method of generating astaxanthin comprising expressing polynucleotides encoding enzymes of an astaxanthin pathway, the polynucleotides comprising:
 (i) a polynucleotide which encodes Phytoene dehydrogenase (crtI) and a first transcriptional regulatory sequence;

(ii) a polynucleotide which encodes Beta-lycopene cyclase (lcy-B) and a second transcriptional regulatory sequence;

(iii) a polynucleotide which encodes Beta-carotene ketolase (crtW) and a third transcriptional regulatory sequence; and wherein the first, second and third regulatory sequence are selected such that the expression of the lcy-B and the crtW is greater than a level of expression of the crtI.

According to an aspect of some embodiments of the present invention there is provided a method of generating astaxanthin comprising expressing polynucleotides encoding enzymes of an astaxanthin pathway, the polynucleotides comprising:

(i) a polynucleotide which encodes Isopentenyl pyrophosphate (idi) and a first transcriptional regulatory sequence;

(ii) a polynucleotide which encodes Geranylgeranyl pyrophosphate synthase (crtE) and a second transcriptional regulatory sequence;

(iii) a polynucleotide which encodes Prephytoene pyrophosphate synthase (crtB) and a third transcriptional regulatory sequence;

(iv) a polynucleotide which encodes Phytoene dehydrogenase (crtI) and a fourth transcriptional regulatory sequence;

(v) a polynucleotide which encodes Beta-lycopene cyclase (lcy-B) and a fifth transcriptional regulatory sequence;

(vi) a polynucleotide which encodes Beta-carotene ketolase (crtW) and a sixth transcriptional regulatory sequence; and (vii) a polynucleotide which encodes Beta-carotene hydroxylase (crtZ) and a seventh transcriptional regulatory sequence wherein the fourth, fifth and sixth regulatory sequence are selected such that the expression of the lcy-B and the crtW is greater than a level of expression of the crtI.

According to an aspect of some embodiments of the present invention there is provided a plurality of isolated polynucleotide sequences encoding enzymes of the astaxanthin pathway comprising:

(i) a polynucleotide which encodes Isopentenyl pyrophosphate (idi) and a first transcriptional regulatory sequence;

(ii) a polynucleotide which encodes Geranylgeranyl pyrophosphate synthase (crtE) and a second transcriptional regulatory sequence;

(iii) a polynucleotide which encodes Prephytoene pyrophosphate synthase (crtB) and a third transcriptional regulatory sequence;

(iv) a polynucleotide which encodes Phytoene dehydrogenase (crtI) and a fourth transcriptional regulatory sequence;

(v) a polynucleotide which encodes Beta-lycopene cyclase (lcy-B) and a fifth transcriptional regulatory sequence;

(vi) a polynucleotide which encodes Beta-carotene ketolase (crtW) and a sixth transcriptional regulatory sequence; and (vii) a polynucleotide which encodes Beta-carotene hydroxylase (crtZ) and a seventh transcriptional regulatory sequence wherein the fourth, fifth and sixth regulatory sequence are selected such that the expression of the lcy-B and the crtW is greater than a level of expression of the crtI.

According to some embodiments of the invention, the plurality of isolated polynucleotide sequences further comprises at least one of:

(iv) a polynucleotide which encodes Isopentenyl pyrophosphate (idi) and a fourth transcriptional regulatory sequence; or (v) a polynucleotide which encodes Geranylgeranyl pyrophosphate synthase (crtE) and a fifth transcriptional regulatory sequence; or (vi) a polynucleotide which encodes Prephytoene pyrophosphate synthase (crtB) and a sixth transcriptional regulatory sequence; or (vii) a polynucleotide which encodes Beta-carotene hydroxylase (crtZ) and a seventh transcriptional regulatory sequence.

According to some embodiments of the invention, each of the first regulatory sequence, said second regulatory sequence and said third regulatory sequence is a ribosome binding site (RBS).

According to some embodiments of the invention, each of the first regulatory sequence, the second regulatory sequence and the third regulatory sequence is a promoter.

According to some embodiments of the invention, the first regulatory sequence, the second regulatory sequence and the third regulatory sequence are selected such that the expression of said lcy-B and said crtW is at least ten times greater than a level of expression of said crtI.

According to some embodiments of the invention, a sequence of an RBS of (i) is selected to bring about expression of the crtI to at least 80% of the extent as the RBS having a sequence as set forth in SEQ ID NO: 4, 5, 6 or 7;

wherein a sequence of an RBS of (ii) is selected to bring about expression of the lcy-B to at least 80% of the extent as the RBS having a sequence as set forth in SEQ ID NO: 2 or 3;

wherein a sequence of an RBS of (iii) is selected to bring about expression of the crtW to at least 80% of the extent as the RBS having a sequence as set forth in SEQ ID NO: 2 or 3.

According to some embodiments of the invention, a sequence of an RBS of (iv) is selected to bring about expression of the crtI to at least 80% of the extent as the RBS having a sequence as set forth in SEQ ID NO: 4, 5, 6 or 7;

wherein a sequence of an RBS of (v) is selected to bring about expression of the lcy-B to at least 80% of the extent as the RBS having a sequence as set forth in SEQ ID NO: 2 or 3;

wherein a sequence of an RBS of (vi) is selected to bring about expression of the crtW to at least 80% of the extent as the RBS having a sequence as set forth in SEQ ID NO: 2 or 3.

According to some embodiments of the invention, a sequence of an RBS of (i) is selected to bring about expression of the idi to at least 80% of the extent as the RBS having a sequence as set forth in SEQ ID NO: 5;

wherein a sequence of an RBS of (ii) is selected to bring about expression of the crtE to at least 80% of the extent as the RBS having a sequence as set forth in SEQ ID NO: 5;

wherein a sequence of an RBS of (iii) is selected to bring about expression of the crtB to at least 80% of the extent as the RBS having a sequence as set forth in SEQ ID NO: 3;

wherein a sequence of an RBS of (iv) is selected to bring about expression of the crtI to at least 80% of the extent as the RBS having a sequence as set forth in SEQ ID NO: 7;

wherein a sequence of an RBS of (v) is selected to bring about expression of the lcy-B to at least 80% of the extent as the RBS having a sequence as set forth in SEQ ID NO: 2;

wherein a sequence of an RBS of (v) is selected to bring about expression of the crtW to at least 80% of the extent as the RBS having a sequence as set forth in SEQ ID NO: 3; and wherein a sequence of an RBS of (vi) is selected to bring about expression of the crtZ to at least 80% of the extent as the RBS having a sequence as set forth in SEQ ID NO: 6.

According to some embodiments of the invention, a sequence of an RBS of (i) is selected to bring about expression of the idi to at least 80% of the extent as the RBS having a sequence as set forth in SEQ ID NO: 6;

wherein a sequence of an RBS of (ii) is selected to bring about expression of the crtE to at least 80% of the extent as the RBS having a sequence as set forth in SEQ ID NO: 3;

wherein a sequence of an RBS of (iii) is selected to bring about expression of the crtB to at least 80% of the extent as the RBS having a sequence as set forth in SEQ ID NO: 7;

wherein a sequence of an RBS of (iv) is selected to bring about expression of the crtI to at least 80% of the extent as the RBS having a sequence as set forth in SEQ ID NO: 5;

wherein a sequence of an RBS of (v) is selected to bring about expression of the lcy-B to at least 80% of the extent as the RBS having a sequence as set forth in SEQ ID NO: 2;

wherein a sequence of an RBS of (v) is selected to bring about expression of the crtW to at least 80% of the extent as the RBS having a sequence as set forth in SEQ ID NO: 2; and wherein a sequence of an RBS of (vi) is selected to bring about expression of the crtZ to at least 80% of the extent as the RBS having a sequence as set forth in SEQ ID NO: 2.

According to some embodiments of the invention, the plurality of polynucleotide sequences further comprise:

(viii) a polynucleotide encoding a deoxyxylulose-5-phosphate synthase (DXS) and an eighth transcriptional regulatory sequence.

According to some embodiments of the invention, the eighth transcriptional regulatory sequence is selected to bring about expression of the DXS to at least 80% of the extent as the RBS having a sequence as set forth in SEQ ID NO: 6.

According to some embodiments of the invention, the plurality of polynucleotide sequences are comprised in a single expression vector.

According to some embodiments of the invention, the plurality of polynucleotide sequences are comprised in a plurality of expression vectors.

According to some embodiments of the invention, each of the RBS is flanked by a spacer sequence.

According to some embodiments of the invention, the spacer sequence upstream of each of the RBS is at least 80% homologous to the sequence as set forth in SEQ ID NO: 8.

According to some embodiments of the invention, the spacer downstream of each of the RBS is at least 80% homologous to the sequence as set forth in SEQ ID NO: 9.

According to some embodiments of the invention, the bacterial cell is an *E. coli* cell.

According to some embodiments of the invention, the astaxanthin is expressed in an inclusion body in the bacterial cell.

According to some embodiments of the invention, the bacterial cell is genetically modified.

According to some embodiments of the invention, the bacterial cell expresses the plurality of polynucleotides of the present invention. According to some embodiments of the invention, each of the first regulatory sequence, the second regulatory sequence, the third regulatory sequence, the fourth regulatory sequence, the fifth regulatory sequence, the sixth regulatory sequence and the seventh regulatory sequence is a RBS.

According to some embodiments of the invention, the regulatory sequences are selected such that the expression of the lcy-B and the crtW is at least ten times greater than a level of expression of the crtI.

According to some embodiments of the invention, the sequence of the RBS of (iv) is selected to bring about expression of the crtI to at least 80% of the extent as the RBS having a sequence as set forth in SEQ ID NO: 4, 5, 6 or 7;

wherein a sequence of the RBS of (v) is selected to bring about expression of the lcy-B to at least 80% of the extent as the RBS having a sequence as set forth in SEQ ID NO: 2 or 3;

wherein a sequence of the RBS of (vi) is selected to bring about expression of the crtW to at least 80% of the extent as the RBS having a sequence as set forth in SEQ ID NO: 2 or 3.

According to some embodiments of the invention, the sequence of the RBS of (i) is selected to bring about expression of the idi to at least 80% of the extent as the RBS having a sequence as set forth in SEQ ID NO: 5;

wherein a sequence of the RBS of (ii) is selected to bring about expression of the crtE to at least 80% of the extent as the RBS having a sequence as set forth in SEQ ID NO: 5;

wherein a sequence of the RBS of (iii) is selected to bring about expression of the crtB to at least 80% of the extent as the RBS having a sequence as set forth in SEQ ID NO: 3;

wherein a sequence of the RBS of (iv) is selected to bring about expression of the crtI to at least 80% of the extent as the RBS having a sequence as set forth in SEQ ID NO: 7;

wherein a sequence of the RBS of (v) is selected to bring about expression of the lcy-B to at least 80% of the extent as the RBS having a sequence as set forth in SEQ ID NO: 2;

wherein a sequence of the RBS of (vi) is selected to bring about expression of the crtW to at least 80% of the extent as the RBS having a sequence as set forth in SEQ ID NO: 3; and wherein a sequence of the RBS of (vii) is selected to bring about expression of the crtZ to at least 80% of the extent as the RBS having a sequence as set forth in SEQ ID NO: 6.

According to some embodiments of the invention, the sequence of the RBS of (i) is selected to bring about expression of the idi to at least 80% of the extent as the RBS having a sequence as set forth in SEQ ID NO: 6;

wherein a sequence of the RBS of (ii) is selected to bring about expression of the crtE to at least 80% of the extent as the RBS having a sequence as set forth in SEQ ID NO: 3;

wherein a sequence of the RBS of (iii) is selected to bring about expression of the crtB to at least 80% of the extent as the RBS having a sequence as set forth in SEQ ID NO: 7;

wherein a sequence of the RBS of (iv) is selected to bring about expression of the crtI to at least 80% of the extent as the RBS having a sequence as set forth in SEQ ID NO: 5;

wherein a sequence of the RBS of (v) is selected to bring about expression of the lcy-B to at least 80% of the extent as the RBS having a sequence as set forth in SEQ ID NO: 2;

wherein a sequence of the RBS of (vi) is selected to bring about expression of the crtW to at least 80% of the extent as the RBS having a sequence as set forth in SEQ ID NO: 2; and wherein a sequence of the RBS of (vii) is selected to bring about expression of the crtZ to at least 80% of the extent as the RBS having a sequence as set forth in SEQ ID NO: 2.

According to some embodiments of the invention, the method further comprises introducing into the cell a polynucleotide encoding a deoxyxylulose-5-phosphate synthase (DXS).

According to some embodiments of the invention, a sequence of an RBS of the polynucleotide expressing DXS is selected to bring about expression of the DXS to at least 80% of the extent as the RBS having a sequence as set forth in SEQ ID NO: 6.

According to some embodiments of the invention, the expressing is effected in a bacterial cell.

According to some embodiments of the invention, the bacterial cell comprises an *E. coli* cell.

According to some embodiments of the invention, each of the RBS is flanked by a spacer sequence.

According to some embodiments of the invention, the spacer sequence upstream of each of the RBS is at least 80% homologous to the sequence as set forth in SEQ ID NO: 8.

According to some embodiments of the invention, the spacer downstream of each of the RBS is at least 80% homologous to the sequence as set forth in SEQ ID NO: 9.

According to some embodiments of the invention, each of the polynucleotides are comprised on a single expression vector.

According to some embodiments of the invention, the method further comprises isolating the astaxanthin following the expressing.

According to an aspect of some embodiments of the present invention there is provided an isolated polynucleotide comprising:

(i) a first RBS operatively linked to a first enzyme coding sequence;

(ii) a second RBS operatively linked to a second enzyme coding sequence; and (iii) a third RBS operatively linked to a third enzyme coding sequence;

wherein the second RBS is selected such that the level of expression of the second enzyme coding sequence is greater than the level of expression of the first enzyme coding sequence;

wherein the third RBS is selected such that the level of expression of the third enzyme coding sequence is greater than the level of expression of the second enzyme coding sequence;

wherein the first enzyme, the second enzyme and the third enzyme are non-identical enzymes and each part of a biosynthesis pathway of an identical product of interest.

According to some embodiments of the invention, the isolated polynucleotide further comprises:

(iv) a fourth RBS operatively linked to a fourth enzyme coding sequence.

According to some embodiments of the invention, the fourth enzyme is non-identical to the first, second and third enzyme and is part of a biosynthesis pathway of the identical product.

According to some embodiments of the invention, the isolated polynucleotide further comprises:

(v) a fifth RBS operatively linked to a fifth enzyme coding sequence.

According to some embodiments of the invention, the fifth enzyme is non-identical to the first, second, third and fourth enzyme and is part of a biosynthesis pathway of the identical product of interest.

According to some embodiments of the invention, the isolated polynucleotide further comprises:

(vi) a sixth RBS operatively linked to a sixth enzyme coding sequence.

According to some embodiments of the invention, the sixth enzyme is non-identical to the first, second, third, fourth and fifth enzyme and is part of a biosynthesis pathway of the identical product of interest.

According to some embodiments of the invention, each of the RBS is flanked by a spacer sequence.

According to some embodiments of the invention, the spacer sequence upstream of each of the RBS is at least 80% homologous to the sequence as set forth in SEQ ID NO: 8.

According to some embodiments of the invention, the spacer downstream of each of the RBS is at least 80% homologous to the sequence as set forth in SEQ ID NO: 9.

According to some embodiments of the invention, the product of interest is a protein.

According to some embodiments of the invention, the product of interest is selected from the group consisting of a food product, a pharmaceutical and a fuel.

According to an aspect of some embodiments of the present invention there is provided a method of selecting polynucleotide sequences for synthesizing an optimal amount of a product of interest which is the product of a biosynthesis pathway comprising at least three enzymes, the method comprising:

(a) introducing the polynucleotide described herein into a cell under conditions which allow synthesis of the product of interest in the cell; and (b) measuring the amount of the product of interest, wherein an amount of the product of interest is indicative of the polynucleotide sequences to be selected.

According to some embodiments of the invention, the cell is selected from the group consisting of a bacterial cell, a mammalian cell, a plant cell, a fungal cell and an algae cell.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
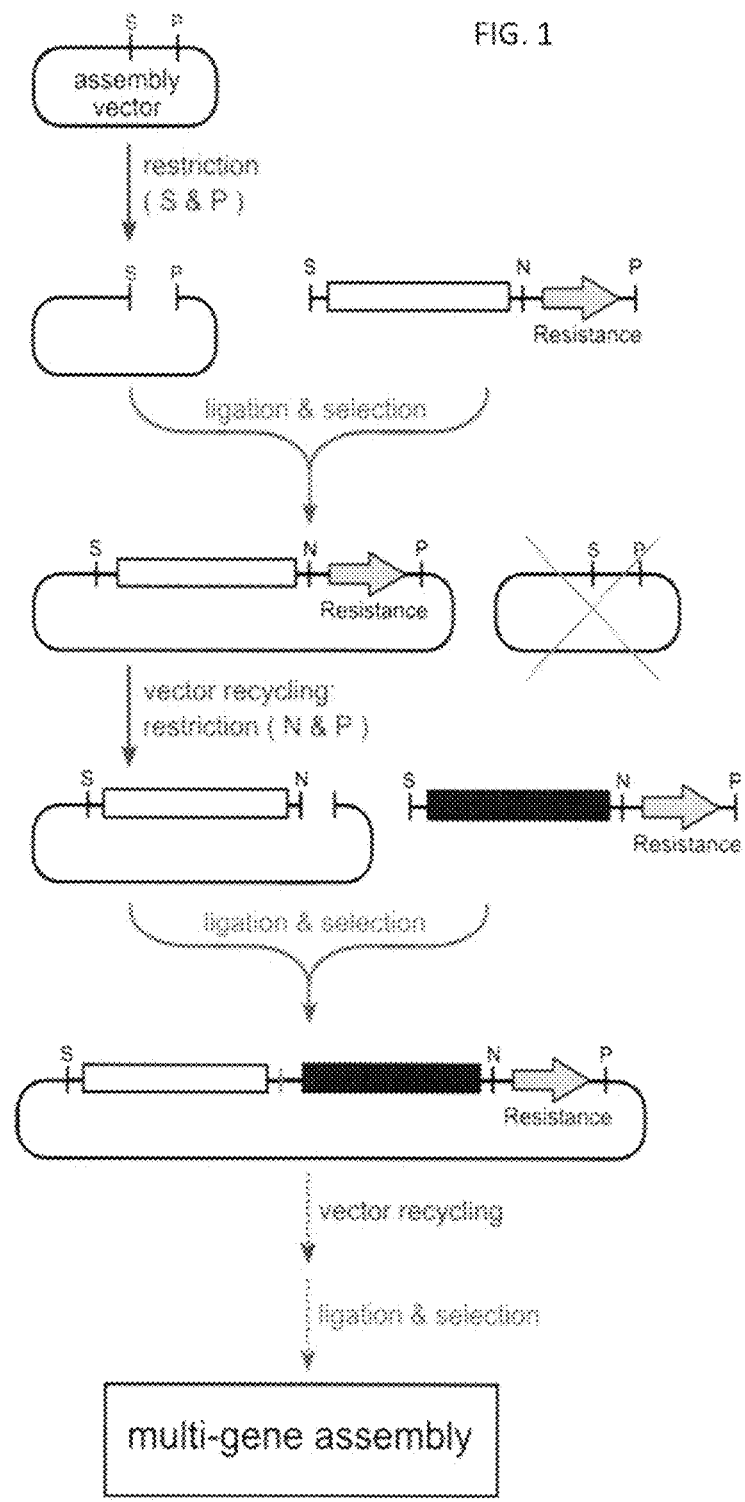

FIG. 1 illustrates a modular cloning strategy for combinatorial assembly of multi-gene constructs. A method of eliminating false-positive clones by a direct selection for correctly assembled constructs was developed. Each gene of interest was joined with a chloramphenicol (Cm) resistance cassette flanked by NheI ('N') and PciI('P') restriction sites. The sequence designated for assembly contains an upstream SpeI ('S') restriction site. To assemble the first target sequence into a vector the DNA was first digested using SpeI and PciI, followed by ligation and transformation. Cells were plated on a selective agar supplemented with Cm. Since the backbone vector does not include Cm resistance, only clones which were properly assembled (i.e. contain the designated sequence and the resistance marker) will be able to form colonies. To incorporate the next target sequence, the assembly product was extracted from the cells and digested with NheI and PciI, effectively discarding the resistance marker from the construct. The second target sequence, as the first one, was digested using SpeI and PciI and assembled to the vector. Importantly, the sticky ends of NheI and SpeI restriction sites are compatible and joined together to form a scar, a sequence that cannot be cleavage by either NheI or SpeI ('x'). After the second assembly round the new construct now contains both target sequences and the Cm resistance, enabling once more a direct selection for positive constructs. This sequence of events can be repeated to assemble multi-gene operons.

Figure 2:
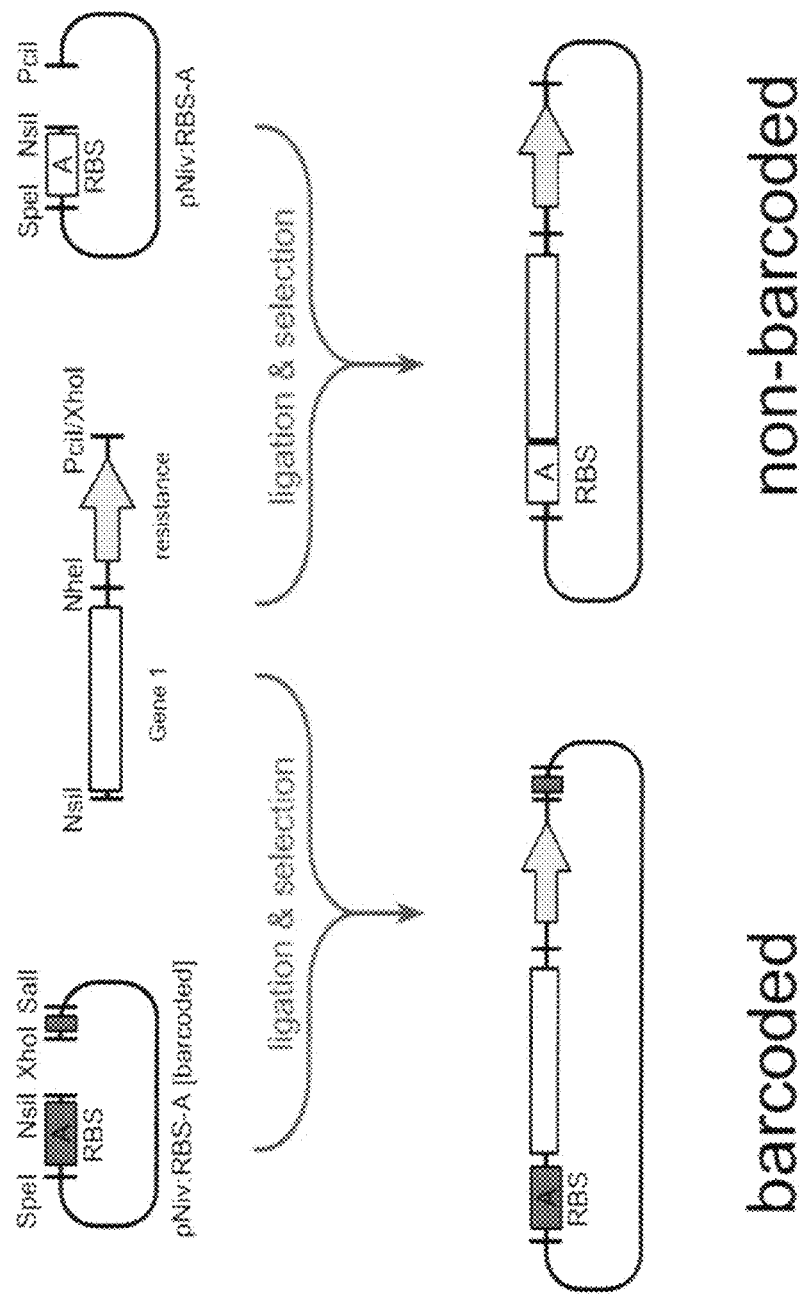

FIG. 2 illustrates RBS modulation of a target ORF. The desired coding sequence is paired with the resistance cassette and then assembled upon a vector containing a RBS upstream to the insertion site. Barcoded and non-barcoded assemblies rely on the same logic but differ in the restriction sites due to technical reasons.

Figure 3:
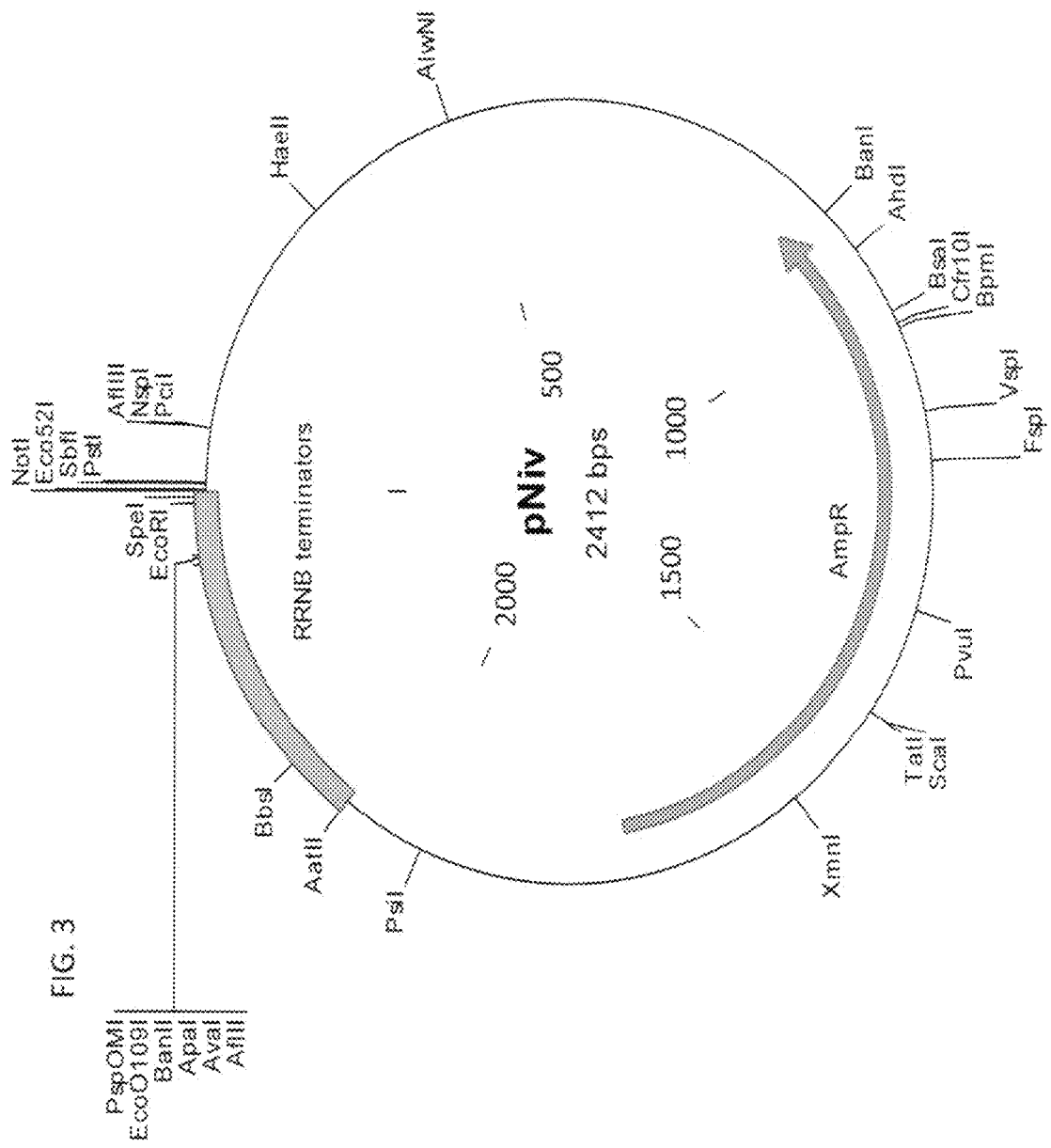

FIG. 3 illustrates the pNiv backbone plasmid. RRNB terminator was placed upstream to the multiple cloning site to minimize leaky expression throughout the assembly process.

Figure 4:
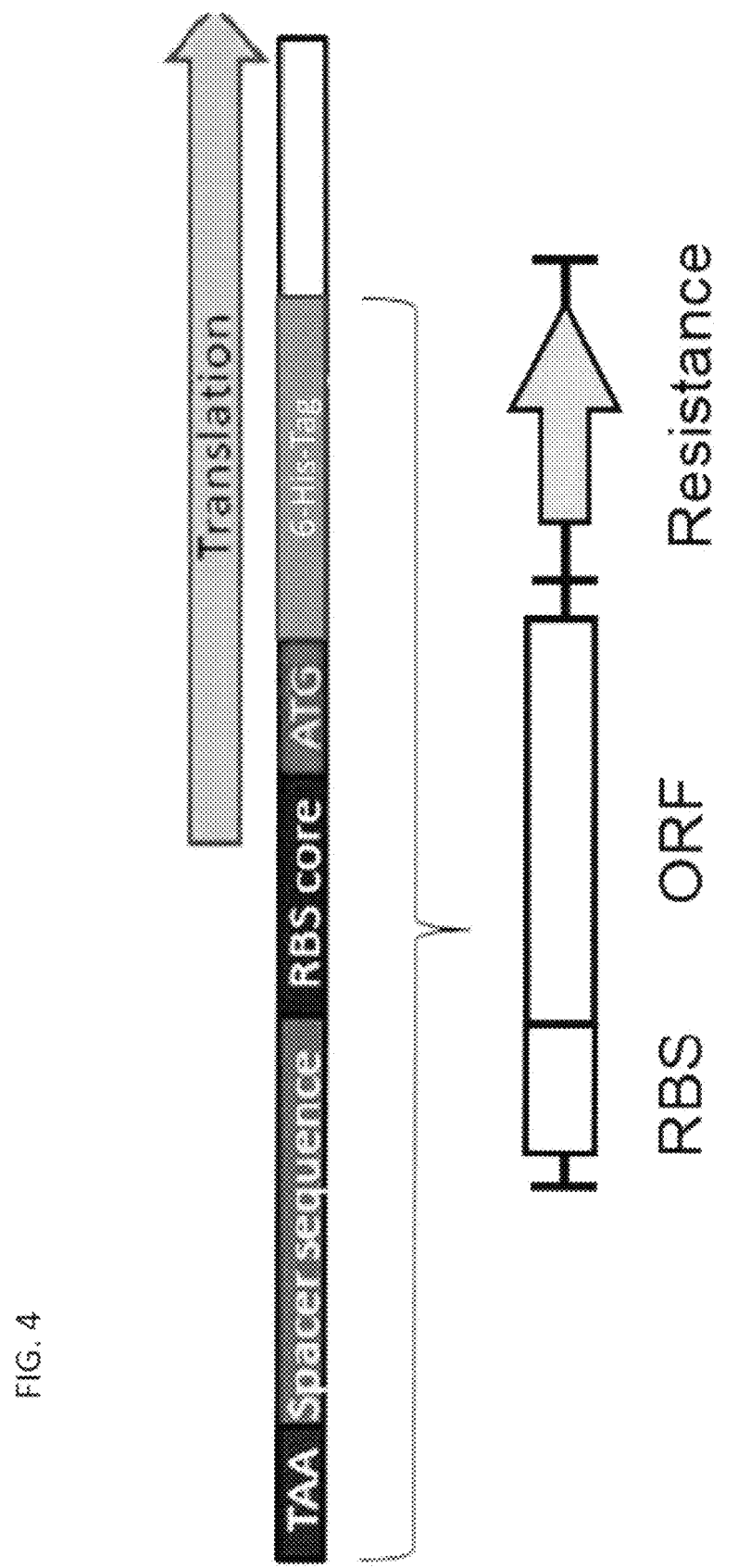

FIG. 4 is a schematic representation of the insulated RBS unit design. The composition of the flanking sequences has been shown to affect the expression level of a given RBS. In an effort to minimize such secondary effects, a constant spacer and tag sequences were introduced up- and downstream to the RBS sequence.

Figure 5:
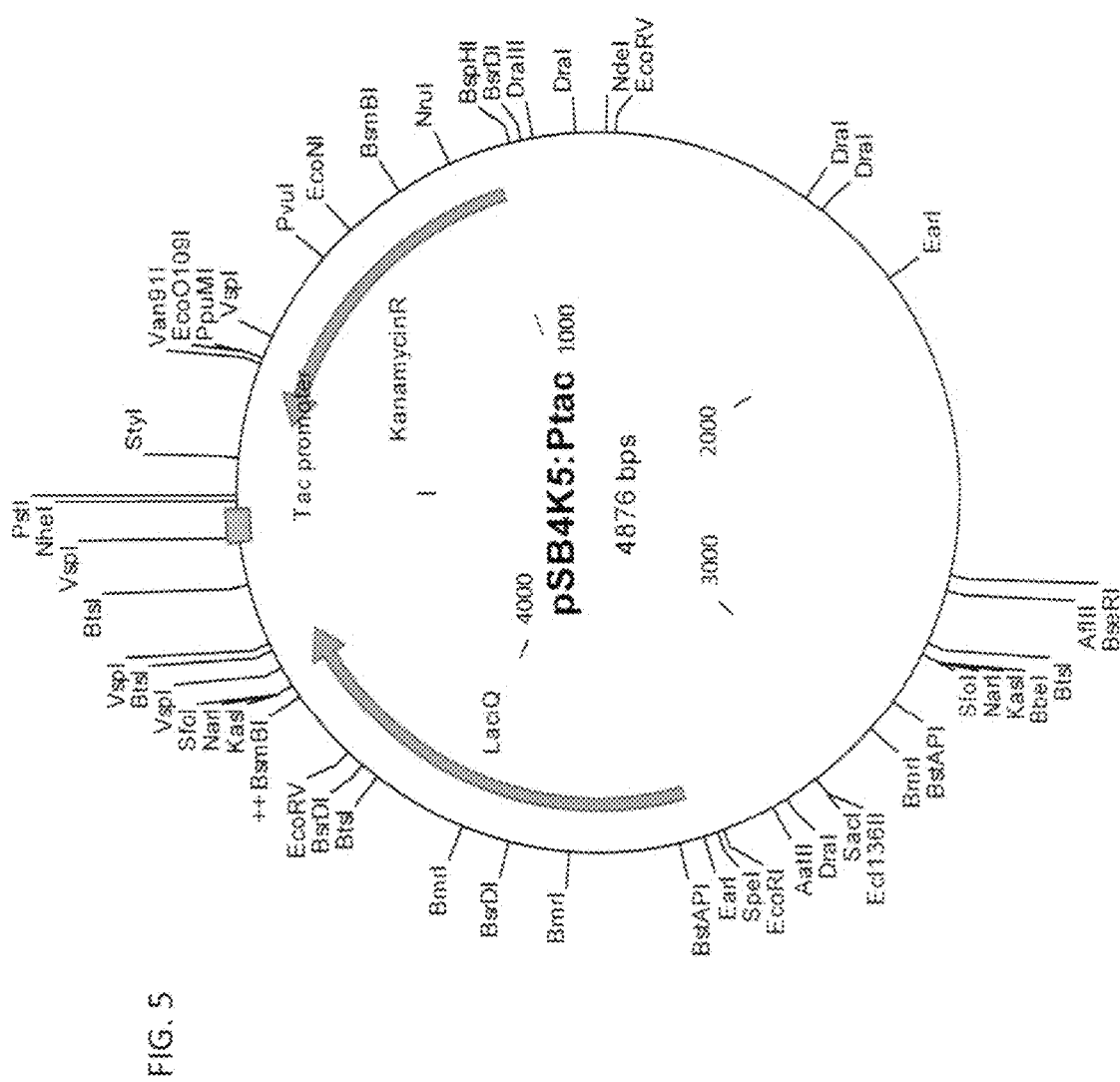
Figure 6:
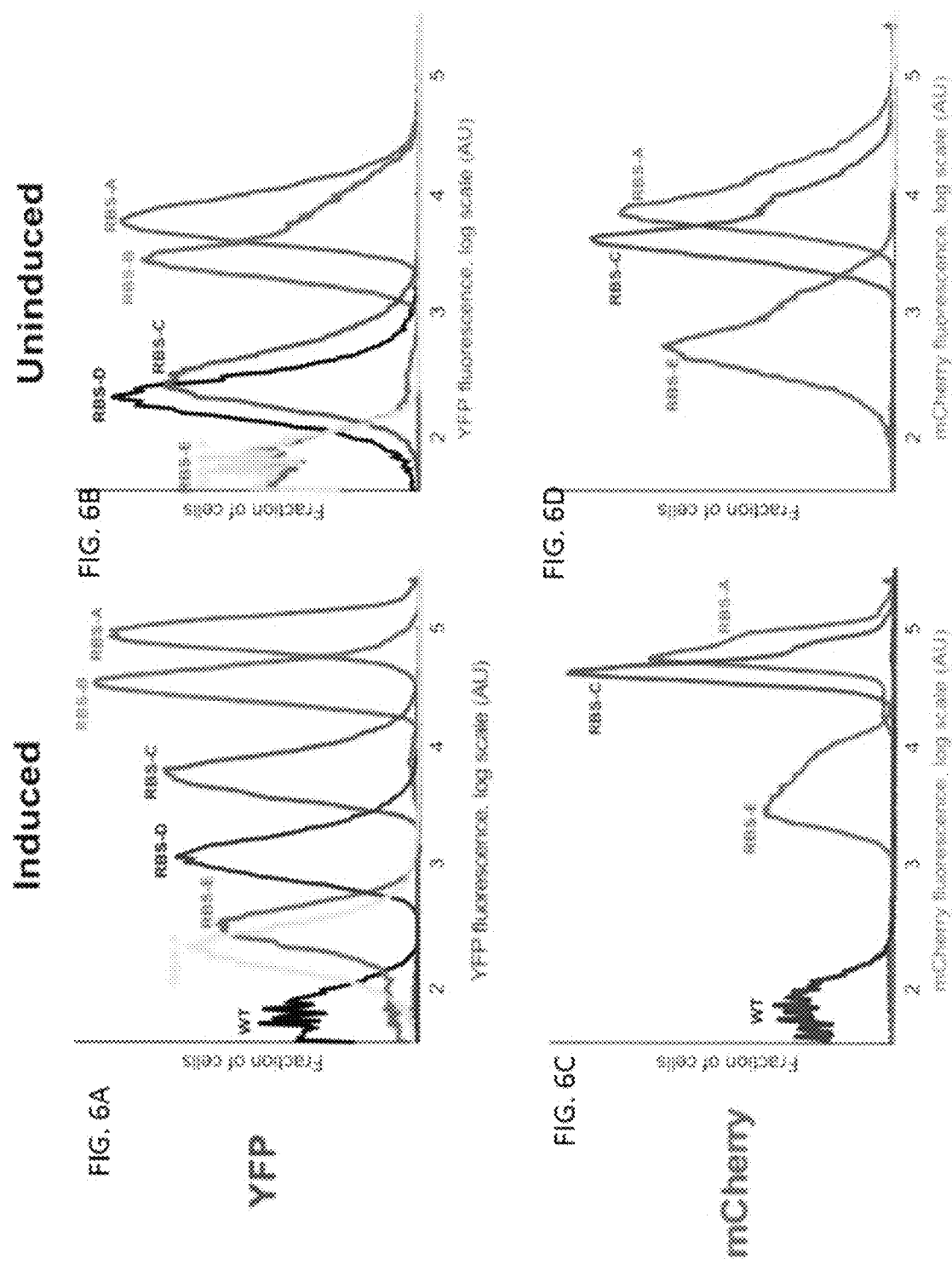

FIG. 5 illustrates the pSB4K5:Ptac—the expression plasmid. The hybrid Ptac promoter was placed on a pSB4K5 plasmid backbone, upstream to the multiple cloning site.

FIGS. 6A-D are graphs illustrating flow cytometry fluorescence measurements of the RBS set using different fluorescence proteins and induction conditions.

Figure 7:
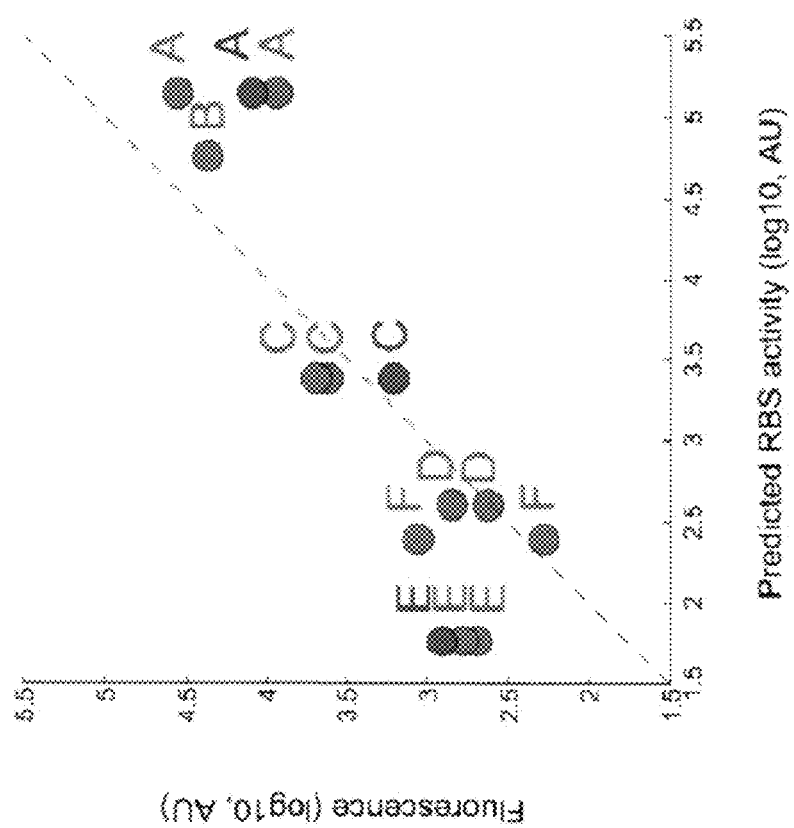

FIG. 7 is a graph comparing predicted RBS activity to experimental fluorescence measurements. CFP (blue), YFP (green) and mCherry (red) reporters were each paired to an RBS sequences (A-F, as denoted by letters). The x-axis represents the predicted RBS activity for each sequence while the y-axis represents the measured fluorescence levels. Fluorescence levels were normalized so the mid-point of the predicted dynamic range–(Predicted$_{max}$–Predicted$_{min}$/2)– corresponds to the mid-point of the experimentally measured dynamic range for each reporter–(Measured$_{max}$–Measured$_{min}$/2).

Figure 8:
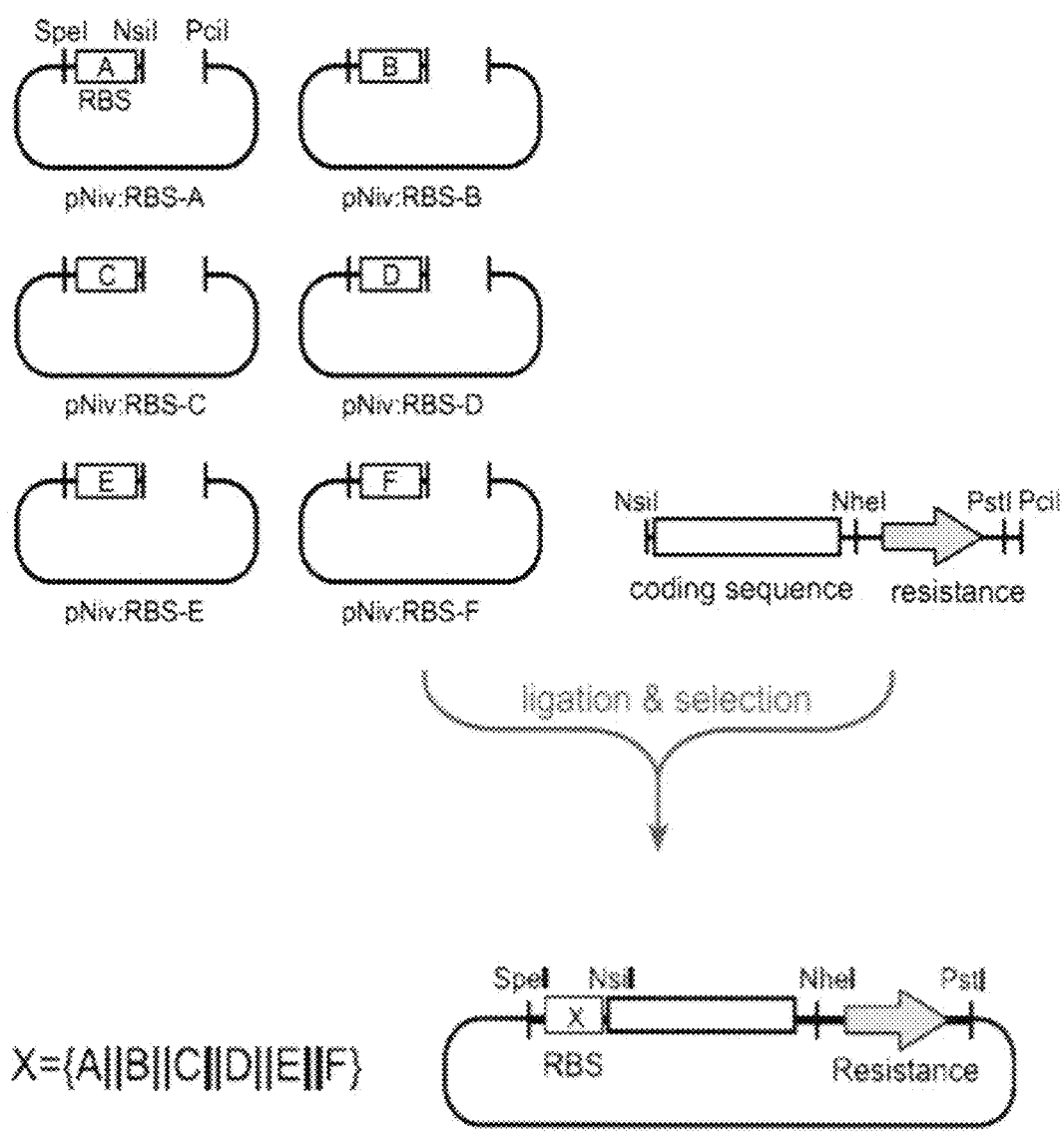

FIG. 8 illustrates single tube combinatorial assembly. An equi-molar mixture of pNiv:RBS plasmids with six distinct RBS sequence was used in the assembly reaction. The target coding sequence was ligated to the plasmid mix to yield six distinct products all containing the same coding sequence but with a different RBS upstream located upstream to it.

Figure 9:
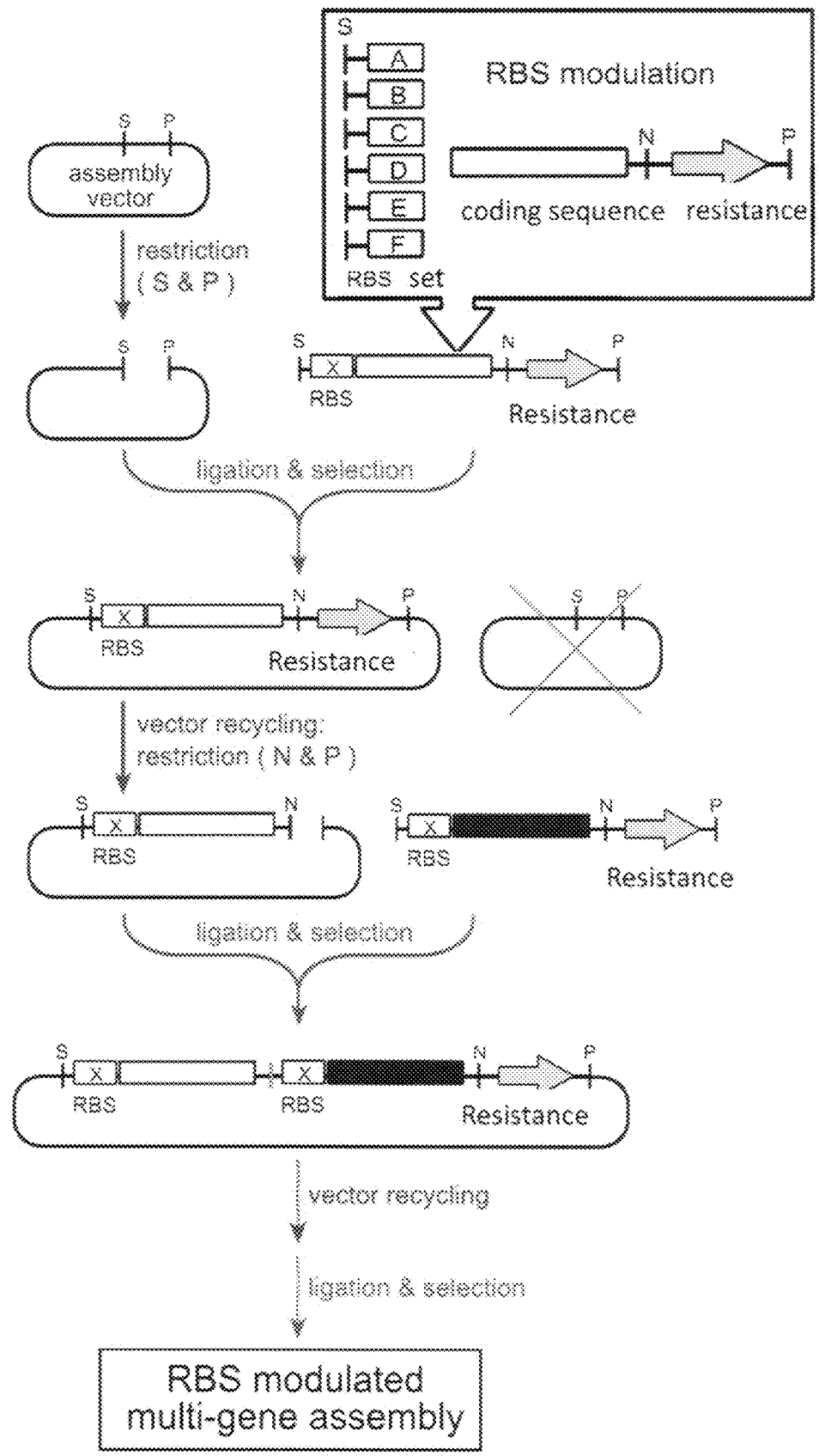

FIG. 9 illustrates the assembly of a synthetic operon of RBS modulated genes.

Figure 10:
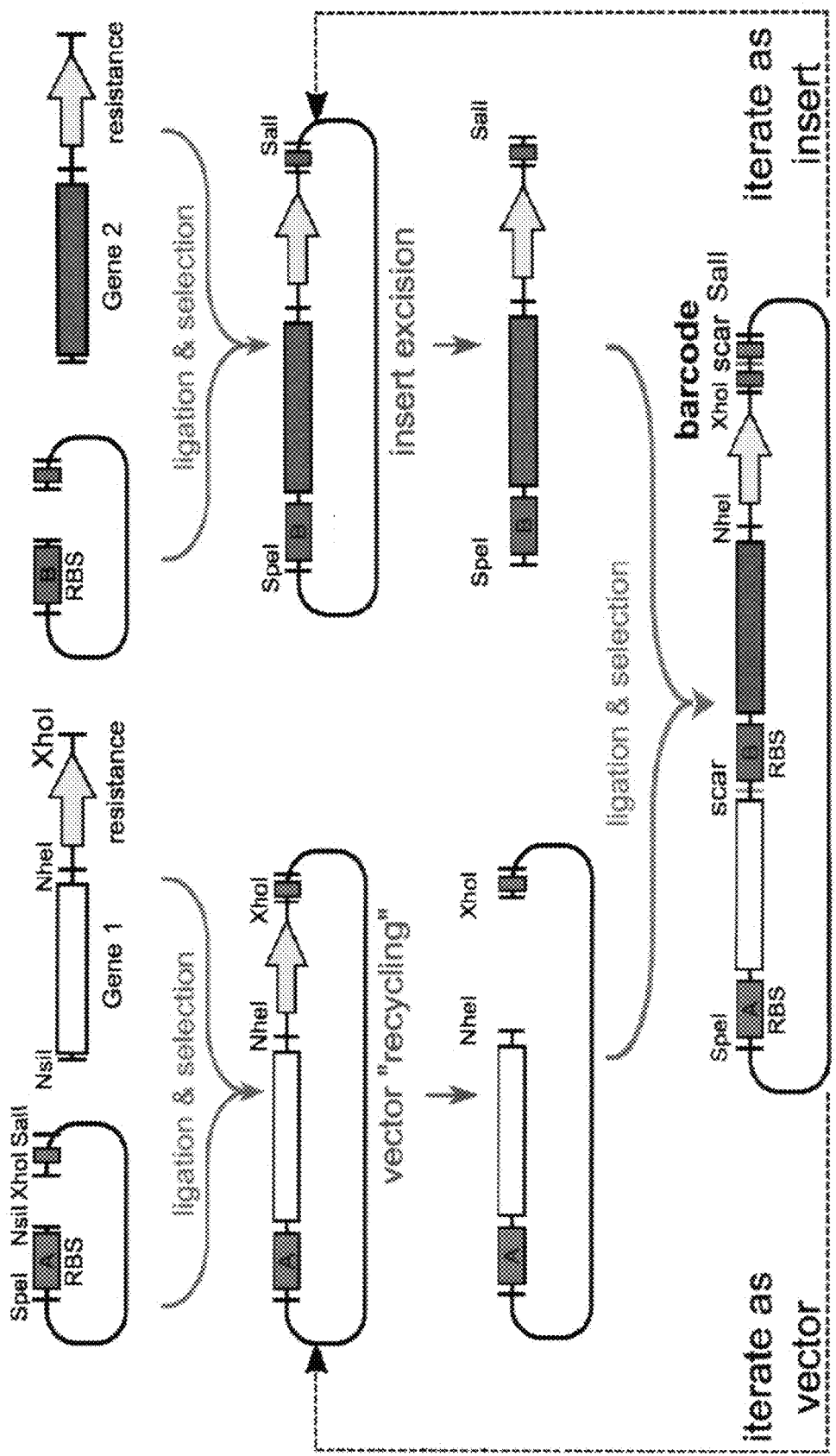

FIG. 10 illustrates assembly of a synthetic operon with barcoded RBS sites. At each assembly step the barcode corresponding to the newly assembled RBS modulated coding sequence is stacked at the 3' end of the operon.

Figure 11:
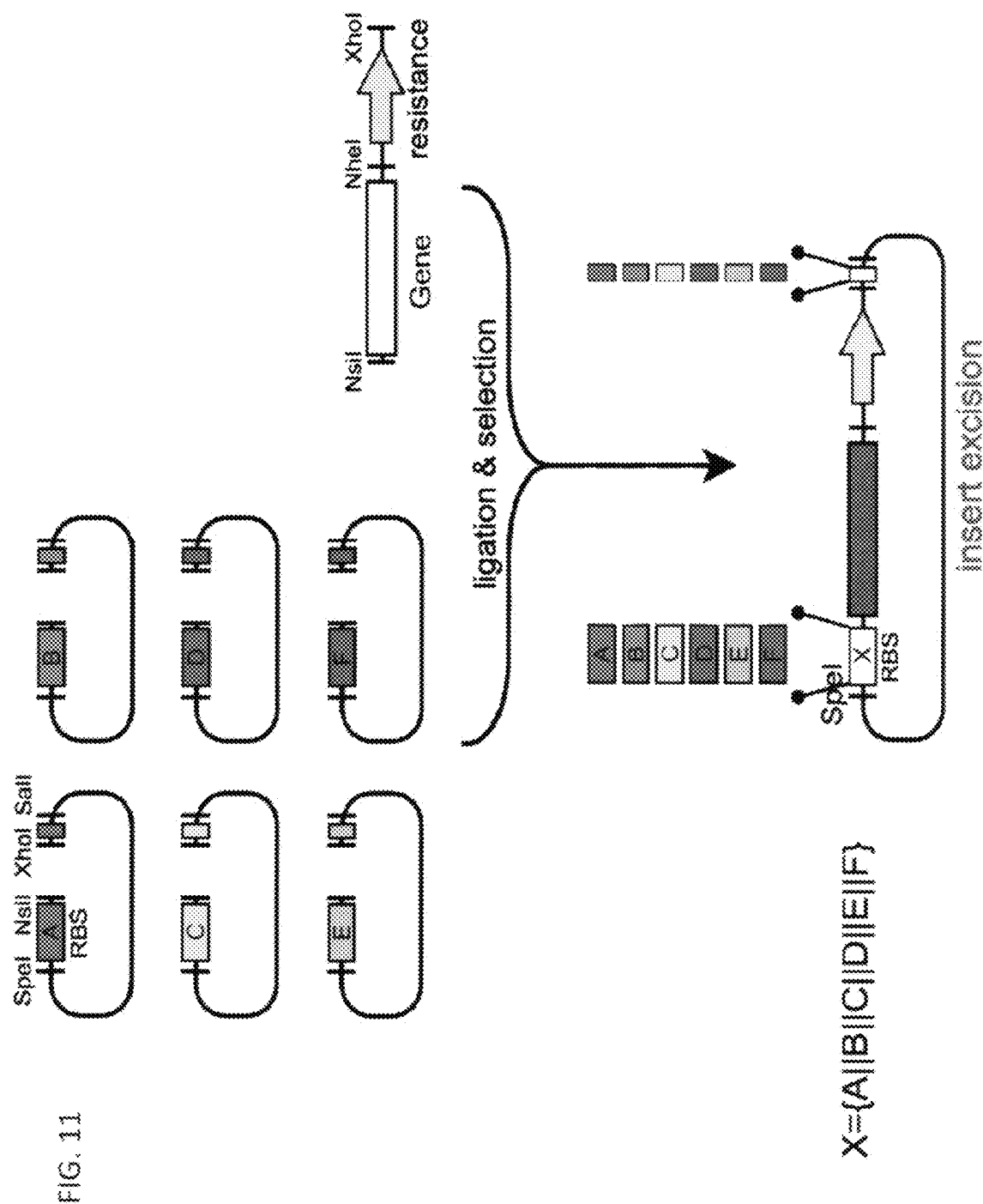

FIG. 11 illustrates single tube combinatorial assembly of barcoded RBS mixture. The target insert is ligated with pRBS-barcoded mixture, the resulting library contains the target coding sequence with different RBS sequence upstream to it.

Figure 12:
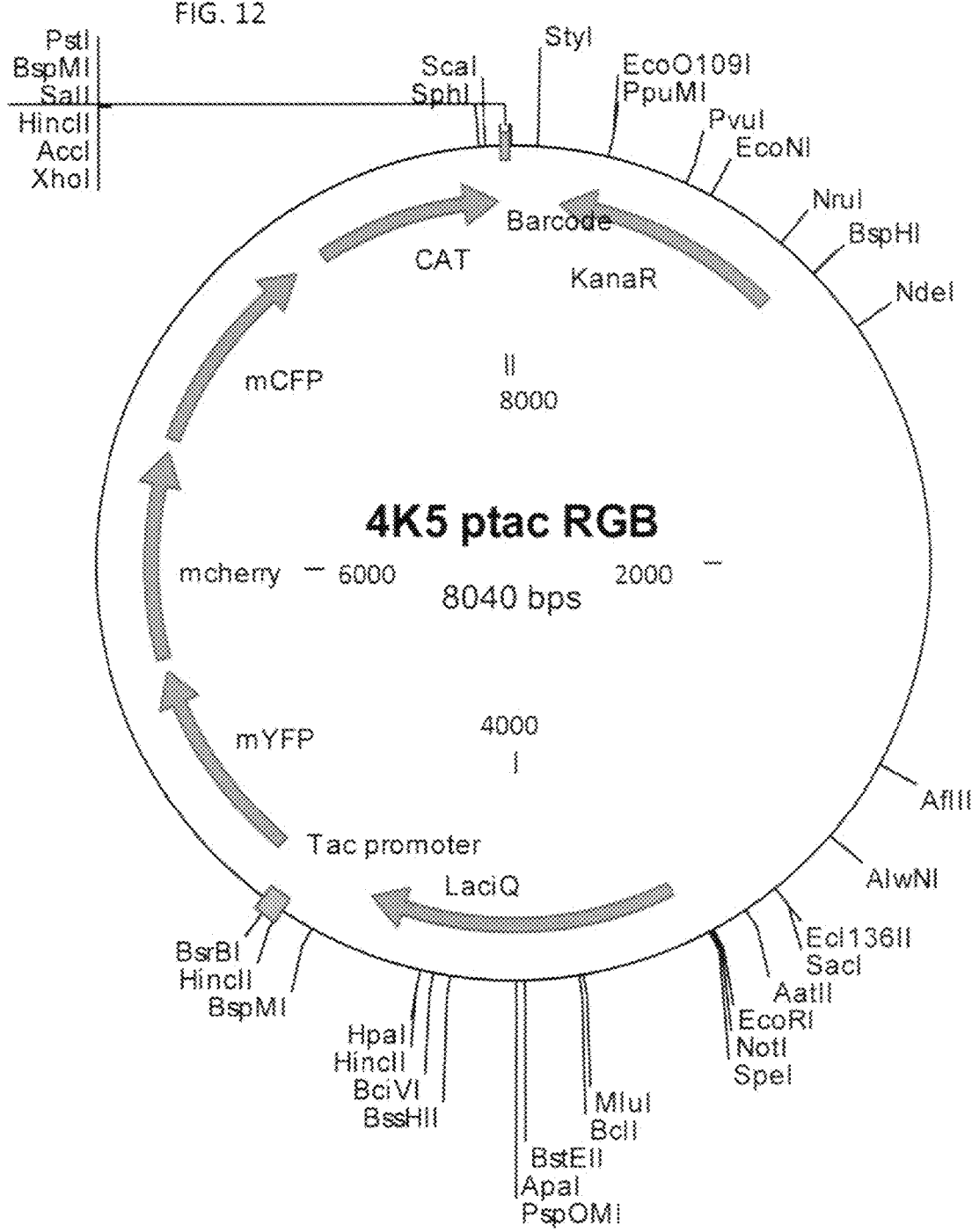

FIG. 12 is a tricolor reporter operon—plasmid map.

Figure 13:
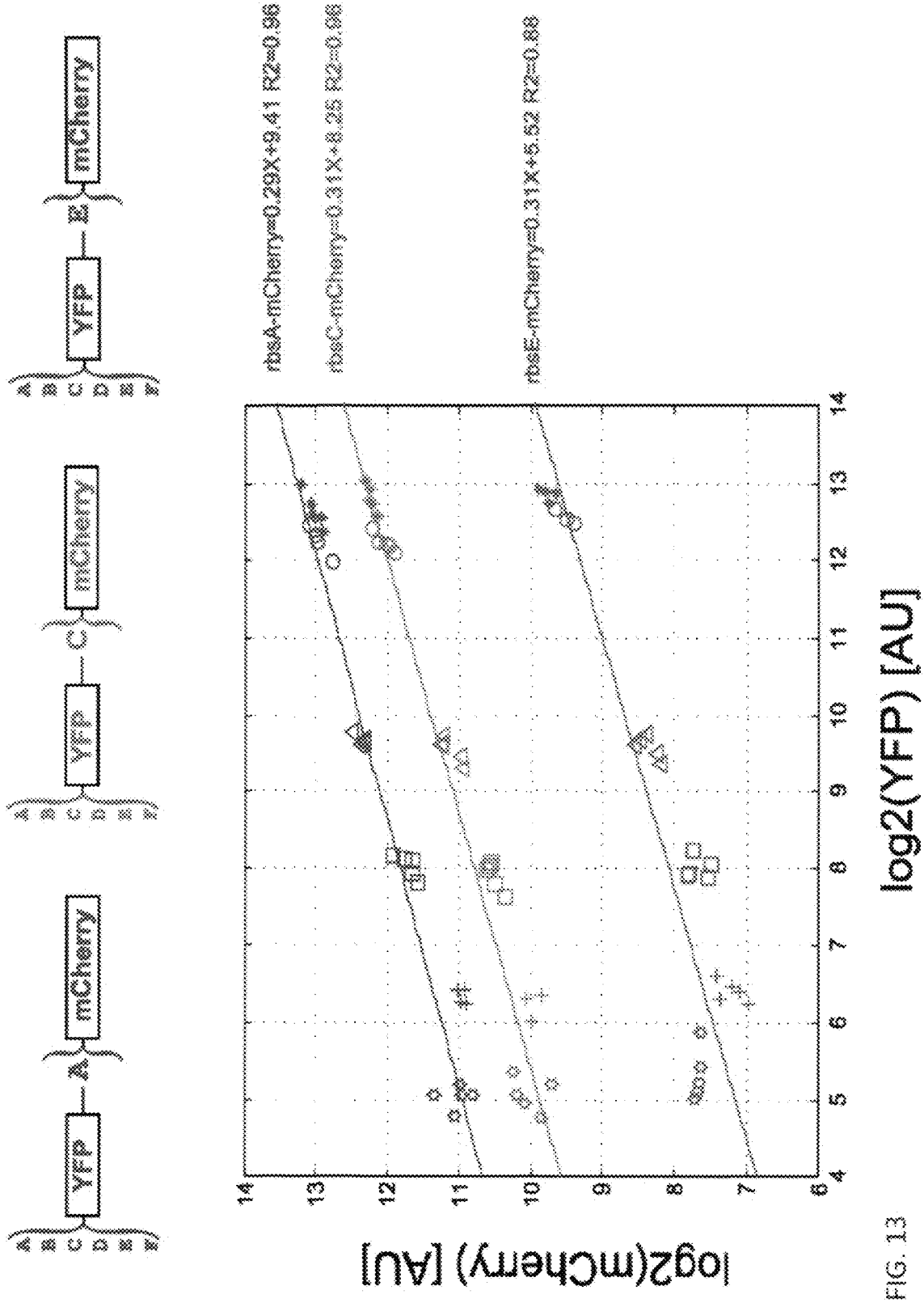

FIG. 13 is a graph illustrating the dependence of the second gene in the operon (mCherry) on first gene (YFP). The RBS sequence controlling mCherry is denoted using colors (blue for RBS A, red for RBS C, and green for RBS E), and RBS sequences controlling YFP corresponds to shapes (asterisk for RBS A, circle for RBS B, triangle for RBS C, square for RBS D, cross for RBS E, and stars for RBS F). The effect of translational coupling is evident, where the expression level of YFP modulates the expression of mCherry. The dependency between YFP and mCherry levels follows a linear trend in log space with a slope of ~⅓.

Figure 14:
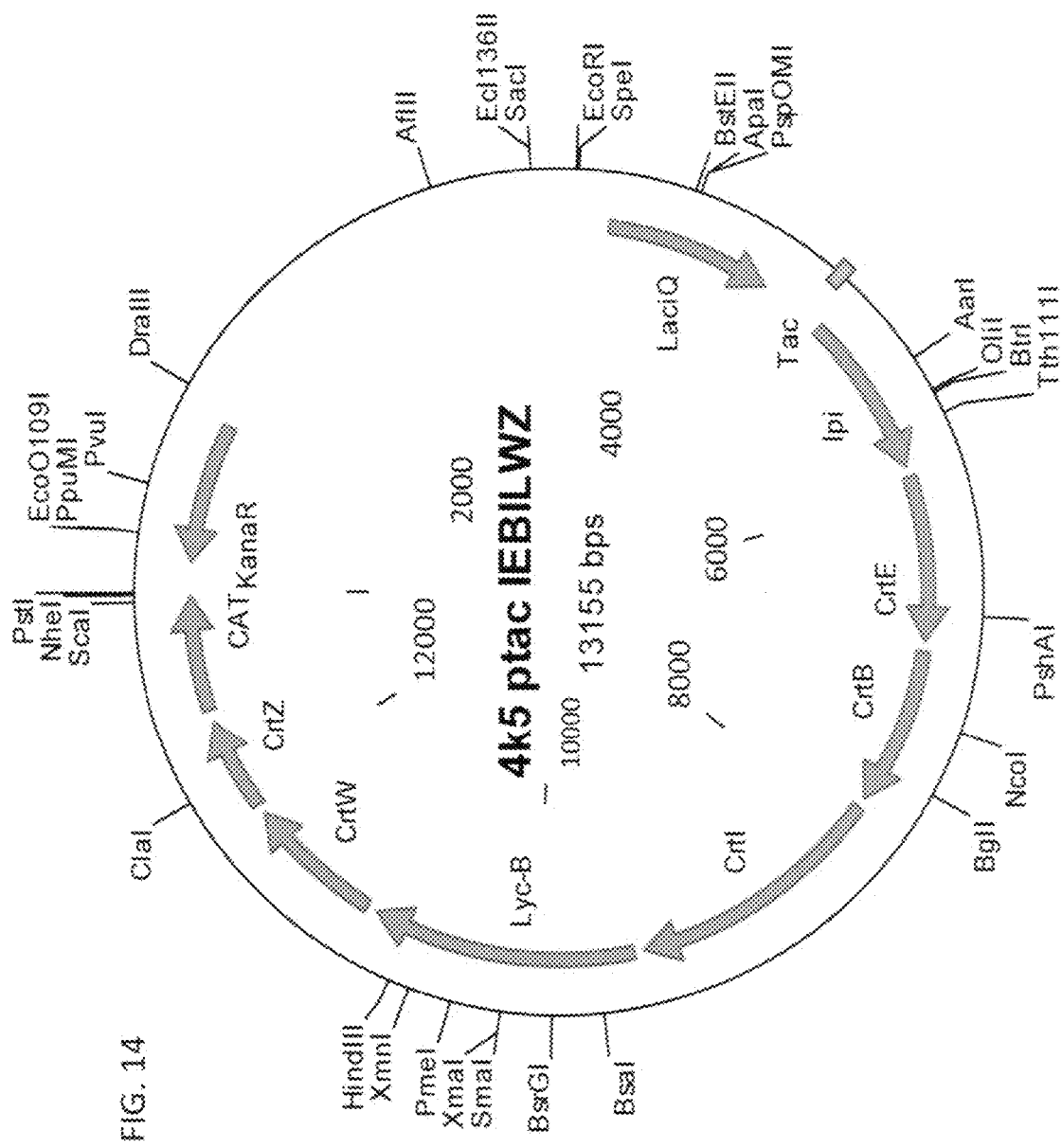

FIG. 14 is a carotenoids biosynthesis operon—plasmid map.

FIGS. 15A-D illustrates that modulation of enzyme expression levels is required for balanced pathway function. (A) A simple quantitative model based on a reversible Michaelis-Menten kinetics that consists of two enzymes was used to depict the outcomes of an unbalanced enzyme expression. Only a small region of the enzyme concentrations space, shown in white, sustains optimal production. (B) A small set of RBS sequences spans several orders of magnitudes of protein expression. Six pre-characterized RBS sequences were employed and paired to genes of interest downstream to an inducible promoter.

```
#8 (RBS-A):
                                        (SEQ ID NO: 2)
AGGAGGTTTGGA

1 (RBS-B):
                                        (SEQ ID NO: 3)
AACAAAATGAGGAGGTACTGAG

17 (RBS-C):
                                        (SEQ ID NO: 4)
AAGTTAAGAGGCAAGA

27 (RBS-D):
                                        (SEQ ID NO: 5)
TTCGCAGGGGGAAG

#20 (RBS-E):
                                        (SEQ ID NO: 6)
TAAGCAGGACCGGCGGCG

"Dead-RBS" (RBS-F):
                                        (SEQ ID NO: 7)
CACCATACACTG
```

(C) Flow cytometry fluorescence measurement of YFP paired with the set of RBS sequences (15). (D) A modular cloning strategy for combinatorial assembly of multi-gene constructs which enables the barcoding of assembled parts and direct selection for correctly assembled constructs. Each gene of interest is joined with a chloramphenicol (Cm) resistance cassette and paired with a library of RBS sequences. Once the first gene is assembled into the vector, properly assembled clones are selected for Cm resistance. To insert the next gene, the marker is discarded and the additional part is assembled into the vector. The newly formed construct contains the two RBS-modified genes and a resistance marker, enabling once more a direct selection for positive constructs. This sequence of steps can be repeated to easily assemble a combinatorial library of RBS-modulated multi-gene operons.

FIGS. 16A-D illustrate that RBS modulation of three fluorescent proteins spans a color space. (A) CFP, YFP and mCherry were combinatorially joined with three representatives of the present RBS set (sequences 'A', 'C' and 'E'), and the genes were assembled together. The resulting operon library differs only in the RBS sequences regulating gene expression. (B) A fluorescence microscopy imaging of *E. coli* colonies, transformed with an operon library. The observed colors represent additive combinations of the three primary colors, assigned to each of the fluorescent proteins. Irregular colony shapes are the result of touching boundaries of adjacent colonies. Some colonies harboring weak RBS appear black. Inset: a brightfield image. (C) Fluorescence imaging of *E. coli* colonies containing the tricolor RBS modulated operon. The images are arranged on a 3D grid where the position on each axis corresponds to the RBS strength of the fluorescent proteins. (D) YFP and mCherry fluorescence levels of clones sampled from a two-color operon library. RBS composition, as determined by barcode sequencing (see supporting online text) is shown. Identical genotypes (each labeled in a distinct color) cluster together in the fluorescence space. The effect of translational coupling is also evident, where the expression level of YFP modulates the expression of mCherry by up to half an order of magnitude.

Figure 17A:
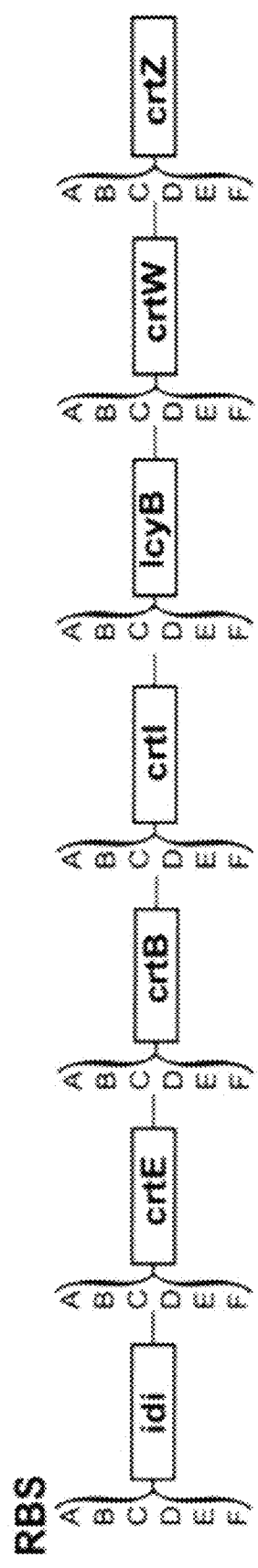
Figure 17B:
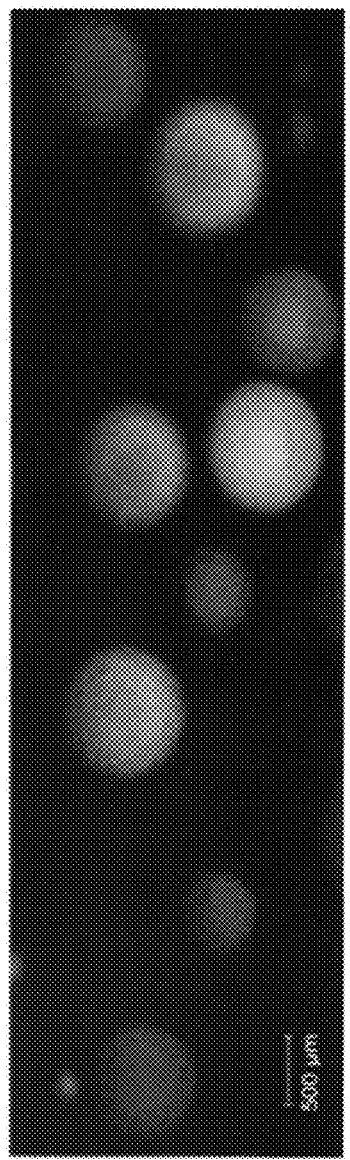
Figure 17C:
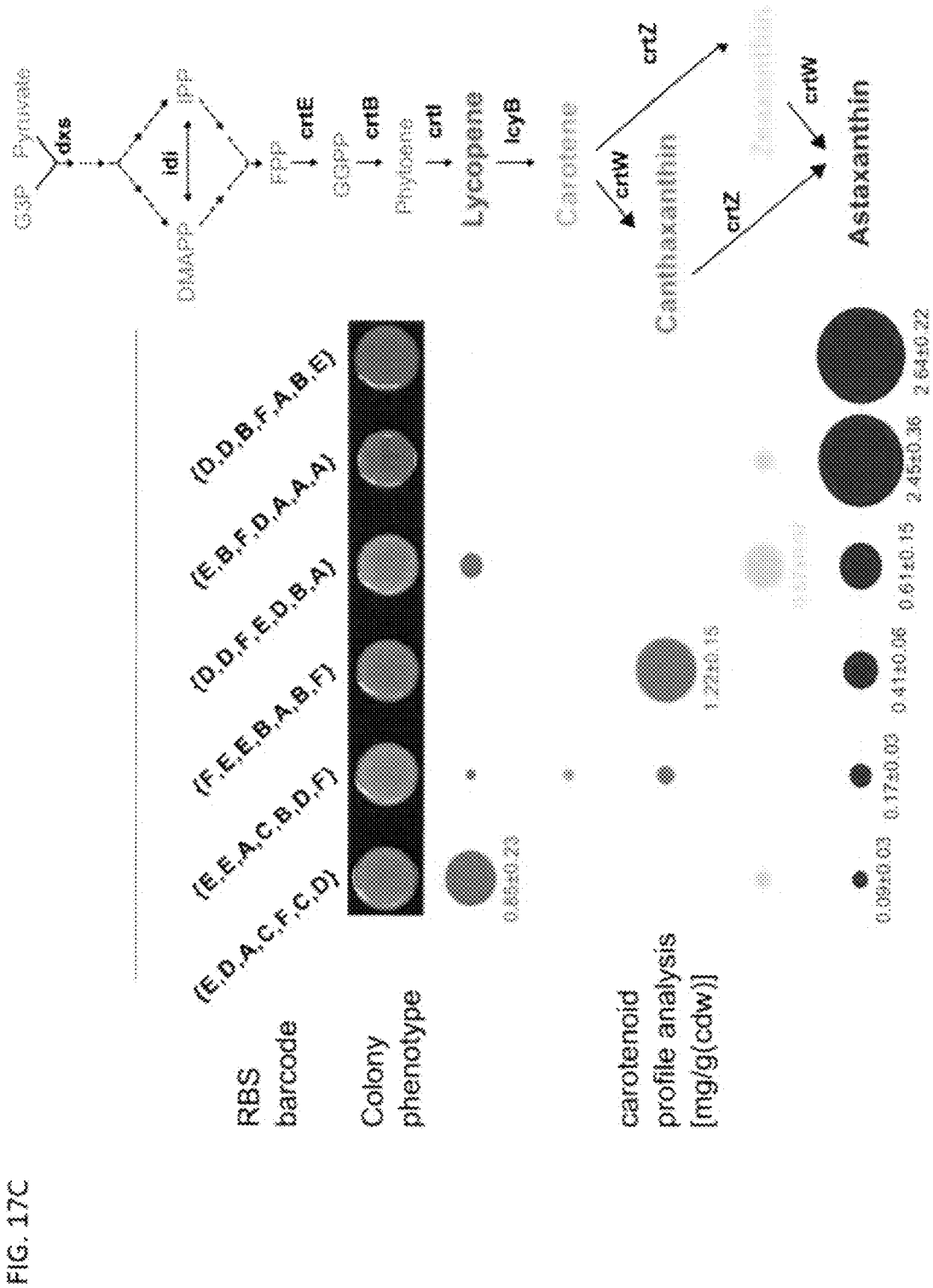

FIGS. 17A-C illustrate that carotenoid accumulation profile varies with the RBS sequences of biosynthetic genes. (A) A library of synthetic operons differing in the RBS sequences regulating each of the seven genes of the carotenoid biosynthesis pathway was generated. (B) A binocular microscopy imaging of *E. coli* colonies transformed with the operon library. The color of the colony corresponds to the composition of the accumulated carotenoids, each having a characteristic color. (C) The carotenoid accumulation profile and RBS composition of clones sampled from the transformed library. The RBS composition of each sampled clone was determined by sequencing (RBS encoding in barcode refers to the order of genes as illustrated in 3A) and the carotenoid profile of each clone was analyzed using HPLC. Different genotypes result in distinct phenotypes, i.e. distinct carotenoids accumulation profiles. Circle area indicates the production yield of a carotenoid intermediate, according to the metabolic pathway described on the right (15).

DESCRIPTION OF SPECIFIC EMBODIMENTS OF THE INVENTION

The present invention, in some embodiments thereof, relates to a biotechnological method for generation of products of metabolic pathways such as astaxanthin.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 15A:
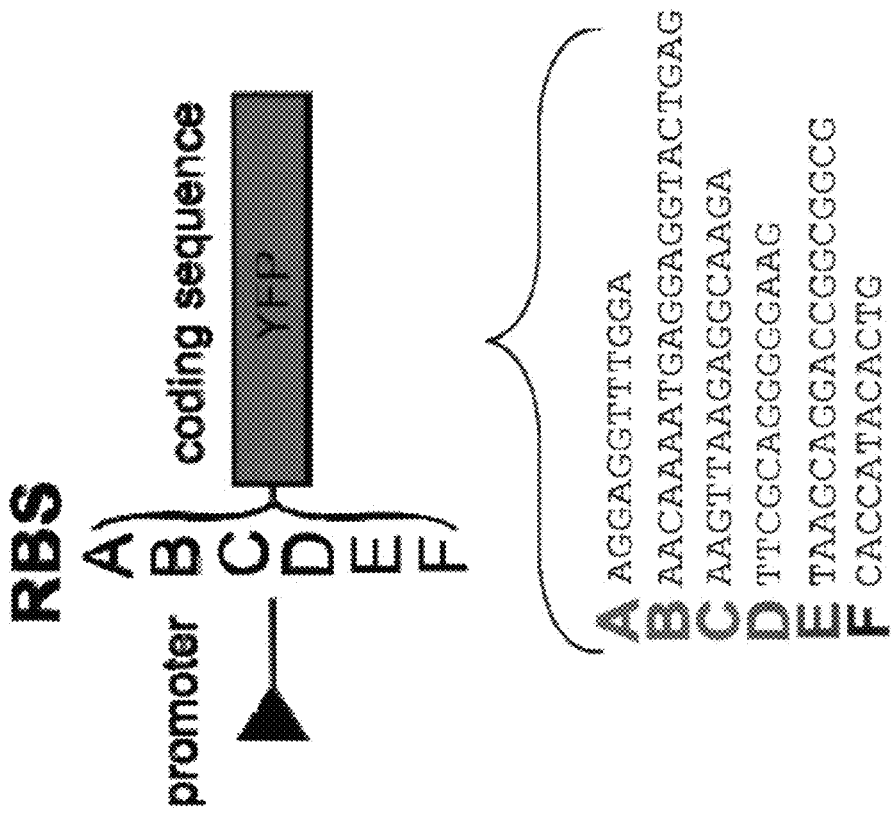

Tuning the expression of recombinant enzymes is essential for the optimization of a metabolic pathway (FIG. 15A). There are two main strategies to achieve balanced expression levels. Rational design involves the calculation or estimation of the relative and absolute amount of each of the pathway's component. However, such attempts are often limited by the lack of sufficient information regarding the kinetics, energetics, and regulation of pathway components. Alternatively, strategies based on random mutagenesis of regulatory elements can sample the expression space and screen or select for a desired phenotype. Yet, even a large pool of mutants does not ensure adequate coverage of the expression space: often, the vast majority of genotypes are clustered in a small portion of the phenotypic space. Moreover, random mutagenesis often yields large libraries in which screening for a desired phenotype can be challenging or even infeasible.

The present inventors introduced a strategy that facilitates the exploration of the phenotypic space using a compact set of regulatory elements. By employing a small set of well-characterized RBS sequences to regulate the expression of multiple genes in a synthetic operon, the present inventors were able to efficiently sample the multi-dimensional expression space across several orders of magnitude in each axis. Importantly, the small size of the RBS set limits the number of genetic variants in the library and enables a fast screening.

By modulating the ribosome binding sites of genes involved in carotenoid biosynthesis, the present inventors demonstrate that the accumulation of metabolic products of a pathway varies significantly according to the RBS sequences regulating its constituent enzymes. The present inventors found that the combinatorial assembly of the astaxanthin biosynthetic pathway resulted in a 4-fold yield increase over conventional assembly and selection methods, thereby exemplifying the strength of sampling of the expression space using a small set of characterized regulatory elements.

The strategy presented herein can be expanded in various ways. Specifically, other regulatory elements can further modulate gene expression. For example, by employing a small library of promoters to control the transcription of the operon, the span of the overall expression space can be further increased by several orders of magnitudes.

In order to determine the ratios of enzymes of the metabolic pathway required for optimal production of the product of the metabolic pathway, the present inventors have generated a polynucleotide construct which comprises at least three different RBS sequences, each RBS being of a different strength. Introduction of the sequences encoding the relevant enzymes of the metabolic pathway into this construct in various permutations allows for the screening of the optimal RBS-enzyme combinations.

Thus, according to one aspect of the present invention there is provided an isolated polynucleotide comprising:
  (i) a first RBS operatively linked to a first enzyme coding sequence;
  (ii) a second RBS operatively linked to a second enzyme coding sequence; and
  (iii) a third RBS operatively linked to a third enzyme coding sequence;
  wherein the second RBS is selected such that the level of expression of the second enzyme is greater than the level of expression of the first enzyme;
  wherein the third RBS is selected such that the level of expression of the third enzyme is greater than the level of expression of the second enzyme;
  wherein the first enzyme, the second enzyme and the third enzyme are non-identical enzymes and each part of a biosynthesis pathway of an identical product.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

A "ribosome binding site" (RBS) is a short nucleotide sequence usually comprising about 4-16 base pairs and functions by positioning the ribosome on the mRNA molecule for translation of an encoded protein.

A nucleic acid is "operably linked" when it is placed into a functional relationship with another nucleic acid sequence. For example, a promoter is operably linked to a coding sequence if it affects the transcription of the sequence; or a ribosome binding site is operably linked to a coding sequence if it is positioned so as to facilitate translation. Linking of nucleic acid sequences may be accomplished by ligation at convenient restriction sites. If such sites do not exist, synthetic oligonucleotide adaptors or linkers may be used in accordance with conventional practice, such as assembly PCR.

Sequences of exemplary RBS and their relative strength may be found in Salis et al., Nature Biology, Volume 27, No. 10, 2009, page 946-950, including the supplementary information thereof, incorporated herein by reference. Preferably, the RBS is selected to one whose strength is not affected by the downstream sequence. Methods of selecting the relative strength of an RBS are also disclosed therein. For example, the relative strength of an RBS may be determined by linking it to a polynucleotide sequence encoding a detectable marker and expressing the marker in a cell. The marker may be a fluorescent protein, a phosphorescent protein or any protein that may be detected using an antibody. The amount of the detectable protein correlates with the strength of the RBS.

Exemplary RBS sequences include for example:

```
(RBS-A):
                                    (SEQ ID NO: 2)
    AGGAGGTTTGGA (RBS-B):
                                    (SEQ ID NO: 3)
    AACAAAATGAGGAGGTACTGAG (RBS-C):
                                    (SEQ ID NO: 4)
    AAGTTAAGAGGCAAGA
```

```
-continued
(RBS-D):
                                    (SEQ ID NO: 5)
    TTCGCAGGGGAAG (RBS-E):
                                    (SEQ ID NO: 6)
    TAAGCAGGACCGGCGGCG (RBS-F):
                                    (SEQ ID NO: 7)
    CACCATACACTG
```

Additional RBS sequences are as follows:

```
                                    (SEQ ID NO. 70)
    AGGAAA,, (SEQ ID NO. 71)
    AGAAAA, (SEQ ID NO. 72)
    AGAAGA, (SEQ ID NO. 73)
    AGGAGA, (SEQ ID NO. 74)
    AAGAAGGAAA, (SEQ ID NO. 75)
    AAGGAAAA, (SEQ ID NO. 76)
    AAGGAAAG, (SEQ ID NO. 77)
    AAGGAAAU, (SEQ ID NO. 78)
    AAGGAAAAA, (SEQ ID NO. 79)
    AAGGAAAAG, (SEQ ID NO. 80)
    AAGGAAAAU, (SEQ ID NO. 81)
    AAGGAAAAAA, (SEQ ID NO. 82)
    AAGGAAAAAG, (SEQ ID NO. 83)
    AAGGAAAAAU, (SEQ ID NO. 84)
    AAGGAAAAAAA, (SEQ ID NO. 85)
    AAGGAAAAAAG, (SEQ ID NO. 86)
    AAGGAAAAAAU, (SEQ ID NO. 87)
    AAGGAAAAAAAA, (SEQ ID NO. 88)
    AAGGAAAAAAAG, (SEQ ID NO. 89)
    AAGGAAAAAAAU, (SEQ ID NO. 90)
    AAGGAAAAAAAAA, (SEQ ID NO. 91)
    AAGGAAAAAAAAG,
```

AAGGAAAAAAAAU, (SEQ ID NO. 92)

AAGGAAAAAAAAA, (SEQ ID NO. 93)

AAGGAAAAAAAAG, (SEQ ID NO. 94)

AAGGAGGAAA, (SEQ ID NO. 95)
and

AAGGAAAAAAAAU. (SEQ ID NO. 96)

According to one embodiment, the third RBS is at least 2 times, 3 times, 5 times or even 10 times as strong as the second RBS.

According to another embodiment, the second RBS is at least 2 times, 3 times, 5 times or even 10 times as strong as the first RBS.

It will be appreciated that depending on the number of enzymes of a particular metabolic pathway, and depending on the number of enzymes which are natively expressed in the particular cell system used, the polynucleotide may comprise additional RBSs and encode additional enzymes. Thus, the isolated polynucleotide may comprise a fourth, a fifth or a sixth RBS operatively linked to a different enzyme coding sequence which is present in the metabolic pathway.

Since the sequences flanking the transcriptional regulatory element (e.g. RBS) can affect expression levels, spacer sequences—a constant sequence of 10-50 bp, for example about 20 bp, located upstream and downstream thereof may be inserted into the expression construct.

As used herein, the term "spacer sequence" refers to any sequence that is either upstream or downstream of the sequence being discussed (e.g., for genes A B C, gene B is flanked by the A and C gene sequences). In some embodiments, a flanking sequence is present on only a single side (either 3' or 5') of a DNA fragment, but in preferred embodiments, it is on each side of the sequence being flanked.

An exemplary sequence that may be placed upstream of an RBS is a sequence at least 70% homologous, at least 80% homologous, at least 90% homologous or 100% homologous to (SEQ ID NO: 8). An exemplary sequence that may be placed downstream of an RBS is a sequence at least 70% homologous, at least 80% homologous, at least 90% homologous or 100% homologous to (SEQ ID NO: 9).

As mentioned herein above, the present invention further contemplates insertion of stabilizing mRNA sequences into the expression construct.

A "stabilizing mRNA" is a nucleic acid sequence insert used to influence gene expression. These inserts are generally located between the transcription and translational start sites of a gene or nucleic acid sequence.

Stabilizing mRNA sequences are well known in the art and reference is made to Carrier et al. (1999) Biotechnol. Prog. 15:58-64. Preferred mRNA stabilizing sequences include the sequences:

GGTCGAGTTATCTCGAGTGAGATATTGTTGACG,; (SEQ ID NO. 97)

GGTGGACTTATCTCGAGTGAGATATTGTTGACG,; (SEQ ID NO. 98)

CCTCGAGTTATCTCGAGTGAGATATTGTTGACG,; (SEQ ID NO. 99)

GCTCGAGTTATCTCGAGTGAGATATTGTTGACG,; (SEQ ID NO. 100)

CGTCGAGTTATCTCGAGTGAGATATTGTTGACG,; (SEQ ID NO. 101)

GGTGGAGTTATCTCGAGTGAGATATTGTTGACG, (SEQ ID NO. 102)
and

GCTGGACTTATCTCGAGTGAGATATTGTTGACG,. (SEQ ID NO. 103)

The polynucleotides of the present invention may include additional sequences (e.g. promoters) such that they may be used as expression constructs. In addition, the polynucleotides may include sequences which render this vector suitable for replication and integration in prokaryotes, eukaryotes, or preferably both (e.g., shuttle vectors). Typical cloning vectors contain transcription and translation initiation sequences (e.g., promoters, enhancers) and transcription and translation terminators (e.g., polyadenylation signals), as described herein below.

According to one embodiment, each of the enzyme coding sequences in the polynucleotide is operatively linked to a promoter. In one embodiment, the identical promoter controls expression of each of the enzymes encoded in the polynucleotide.

According to another embodiment, different promoters control expression of the enzymes encoded in the polynucleotide.

Examples of particular promoters are described herein below.

According to one embodiment, the expression construct encodes a selectable marker.

As used herein, the term "selectable marker" refers to a gene capable of expression in host cell which allows for ease of selection of those hosts containing an introduced nucleic acid or vector. Examples of such selectable markers include but are not limited to antimicrobials, (e.g., kanamycin, erythromycin, actinomycin, chloramphenicol and tetracycline). Thus, the term "selectable marker" refers to genes that provide an indication that a host cell has taken up an exogenous polynucleotide sequence or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

As mentioned the polynucleotides described herein encode enzymes which are part of a biosynthesis pathway of an identical product.

As used herein, the phrase "biosynthesis pathway" or "metabolic pathway" refers to a cellular or a cellular (cell-free) system for converting a substrate to a product of interest, where the system comprises a plurality of enzymes and may additionally comprise substrates acted upon by one or more of the enzymes, products of the enzyme-catalyzed reactions, co-factors utilized by the enzymes, and the like. The system may be present in an intact cell, or in a lysate of a cell.

Many metabolic pathways are known and have been described in microbial systems, and are accessible in public databases; see, e.g., Smolke, Ed., The Metabolic Pathway Engineering Handbook: Tools and Applications, CRC Press, New York (2009); Stephanopoulos, Nielsen, and Aristidou, Eds., Metabolic Engineering: Principles and Methodology, Academic Press, New York (1998); Greenberg, Metabolic Pathways: Energetics, Tricarboxylic Acid Cycle, and Carbohydrates, Academic Press, New York (1967); and D. M. Greenberg's multi-volume series entitled Metabolic pathways, Volumes 1-7, each of which is incorporated herein by reference.

In one embodiment, the pathways direct production of a food product, a pharmaceutical or a fuel.

Biosynthesis pathways may include, for example, pathways involved in carbohydrate, amino acid, nucleic acid, steroid, fatty acid, and natural product biosynthesis, and encompass the synthesis of various chemical compounds and materials, including, but not limited to:

a) antibiotics; e.g., actinomycin, bleomycin, rifamycin, chloramphenicol, carbapenems, tetracycline, lincomycin, erythromycin, streptomycin, cyclohexamide, puromycin, cycloserine, bacitracin, penicillin, cephalosporin, vancomycin, polymyxin, and gramicidin;

b) bio surfactants; e.g., rhamnolipids, sophorolipids, glycolipids, and lipopeptides;

c) biological fuels; e.g., bioethanol, biodiesel, and biobutanol;

d) amino acids; e.g., L-glutamate, L-lysine, L-phenylalanine, L-aspartic acid, L-isoleucine, L-valine, L-tryptophan, L-proline (hydroxyproline), L-threonine, L-methionine, L-tyrosine, and D-p-hydroxyphenylglycine;

e) organic acids; e.g., citric acid, lactic acid, gluconic acid, acetic acid, propionic acid, succinic acid, fumaric acid, and itaconic acid;

f) fatty acids; e.g., arachidonic acid, polyunsaturated fatty acid (PUBA), and .alpha.-linoleic acid;

g) alcohols and polyols; e.g., glycerol, mannitol, erythritol, xylitol, poly-3-hydroxybutyrate, isobutanol, and 1-butanol;

h) flavors and fragrances; e.g., vanillin, benzaldehyde, dihydroxyacetone, 4-(R)-decanolide, and 2-actyl-1-pyrroline;

i) nucleotides; e.g., 5'-guanylic acid and 5'-inosinic acid;

j) vitamins; e.g., vitamin C, vitamin F, vitamin B2, provitamin D2, vitamin B12, folic acid, nicotinamide, biotin, 2-keto-L-gulonic acid, and provitamin Q10;

k) pigments; e.g., astaxanthin, .beta.-carotene, leucopene, monascorubrin, and rubropunctatin;

l) sugars and polysaccharides; e.g., ribose, sorbose, xanthan, gellan, and dextran; and [0066] m) biopolymers and plastics; e.g., polyhydroxyalkanoates (PHA), poly-.gamma.-glutamic acid, and 1,3-propanediol.

Other examples of biosynthesis pathways of interest include the synthesis of various E. coli metabolites.

A "metabolite" is any substance used or produced during metabolism (e.g., an enzyme, substrate, or product). Herein, a metabolite is often, although not always, the product of an enzyme in the pathway of interest.

Exemplary E. coli metabolites include, but are not limited to, 2,3-dihydroxybenzoic acid, 2-ketoglutarate, 3-phosphoglycerate, 4-hydroxybenzoate, 6-phosphogluconate, acetoacetyl-CoA, acetyl-CoA, acetylphosphate, adenine, adenosine, adenosine phosphosulfate, ADP, ADP-glucose, Alanine, AMP, anthranilate, arginine, Asparagine, Aspartate, ATP, carbamylaspartate, cis-aconitate, citrate, citrulline, CMP, coenzyme A, CTP, cyclic AMP, cytidine, cytosine, dAMP, dATP, dCTP, deoxyadenosine, deoxyguanosine, deoxyribose-5-P, dGMP, dihydroorotate, dihydroxyacetone phosphate, dTDP, dTTP, erythrose-4-phosphate, FAD, flavin mononucleotide, fructose-1,6-bisphosphate, fructose-6-phosphate, fumarate, GDP, gluconate, gluconolactone, glucosamine-6-phosphate, glucose-6-phosphate, glucose-1-phosphate, glutamate, glutamine, glutathione, glutathione disulfide, glyceraldehyde-3-phosphate, glycerate, glycerol-3-phosphate, GMP, GTP, guanine, guanosine, histidine, histidinol, homocysteine, inosine diphosphate, inosine monophosphate, inosine triphosphate, isoleucine, lysine, malate, malonyl-CoA, methionine, myo-inositol, N-Acetyl-glucosamine-1P, N-acetyl-ornithine, NAD+, NADH, NADP+, NADPH, ornithine, oxaloacetate, phenylalanine, phenylpyruvate, phosphoenolpyruvate, proline, propionyl-CoA, PRPP, pyruvate, quinolinate, riboflavin, ribose-5-phosphate, ribulose-5-phosphate, S-adenosyl-L-methionine, serine, shikimic acid, shikimate, succinate, succinyl-CoA, threonine, tryptophan, tyrosine, UDP, UDP-glucose, UDP-glucuronate, UDP-N-acetylglucosamine, uridine, UTP, valine, and xylulose-5-phosphate.

In certain embodiments, the pathway of interest provides for the synthesis of shikimic acid and/or shikimate (shikimate is the anionic form of shikimic acid) and synthetic intermediates thereto, an isoprenoid or terpene (e.g., amorphadiene, farnesene, lycopene, astaxanthin, vitamin A, menthol, beta-carotene), poly-3-hydroxybutyrate, isobutanol, and 1-butanol.

A number of reactions may be catalyzed by enzymes in a biosynthesis pathway of interest. Broad classes of enzymes, which can be identified by enzyme classification number, provided in parentheses, include, but are not limited to:

(EC 1) oxidoreductases; e.g., dehydrogenases, oxidases, reductases, oxidoreductases, synthases, oxygenases, monooxygenases, dioxygenases, lipoxygenases, hydrogenases, transhydrogenases, peroxidases, catalases, epoxidases, hydroxylases, demethylases, desaturases, dismutases, hydroxyltransferases, dehalogenases, and deiodinases;

(EC2) transferases; e.g., transaminases, kinases, dikinases, methyltransferases, hydroxymethyltransferases, formyltransferases, formiminotransferases, carboxytransferases, carbamoyltransferases, amidinotransferases, transaldolases, transketolases, acetyltransferases, acyltransferases palmitoyltransferases, succinyltransferases, malonyltransferases, galloyltransferases, sinapoyltransferases, tigloyltransferases, tetradecanoyltransferases, hydroxycinnamoyltransferases, feruloyltransferases, mycolyltransferases, benzoyltransferases, piperoyltransferases, trimethyltridecanoyltransferase, myristoyltransferases, coumaroyltransferases, thiolases, aminoacyltransferases, phosphorylases, hexosyltransferases, pentosyltransferases, sialyltransferases, pyridinylases, diphosphorylases, cyclotransferases, sulfurylases, adenosyltransferases, carboxyvinyltransferases, isopentenyltransferases, aminocarboxypropyltransferases, dimethylallyltransferases, farnesyltranstransferases, hexaprenyltranstransferases, decaprenylcistransferases, pentaprenyltranstransferases, nonaprenyltransferases, geranylgeranyltransferases, aminocarboxypropyltransferases, oximinotransferases, purinetransferases, phosphodismutases, phosphotransferases, nucleotidyltransferases, polymerases, cholinepho sphotransferases, phosphorylmutases, sulfurtransferases, sulfotransferases, and CoA-transferases;

(EC3) hydrolases; e.g., lipases, esterases, amylases, peptidases, hydrolases, lactonases, deacylases, deacetylases, pheophorbidases, depolymerases, thiolesterases, phosphatases, diphosphatases, triphosphatases, nucleotidases, phytases, phosphodiesterases, phospholipases, sulfatases, cyclases, oligonucleotidases, ribonucleases, exonucleases, endonucleases, glycosidases, nucleosidases, glycosylases, aminopeptidases, dipeptidases, carboxypeptidases, metallocarboxypeptidases, omega-peptidases, serine endopeptidases, cystein endopeptidases, aspartic endopeptidases, metalloendopeptidases, threonine endopeptidases, aminases, amidases, desuccinylases, deformylases, acylases, deiminases, deaminases, dihydrolases, cyclohydrolases, nitrilases, ATPases, GTPases, halidases, dehalogenases, and sulfohydrolases;

(EC 4) lyases; e.g., decarboxylases, carboxylases, carboxykinases, aldolases, epoxylases, oxoacid-lyases, carbon-carbon lyases, dehydratases, hydratases, synthases, endolyases, exolyases, ammonia-lyases, amidine-lyases, amine-lyases, carbon-sulfur lyases, carbon-halide lyases, phosphorus-oxygen lyases, and dehydrochlorinases;

(EC 5) isomerases; e.g., isomerases, racemases, mutases, tautomerases, phosphomutases, phosphoglucomutases, aminomutases, cycloisomerase, cyclases, topoisomerases; and (EC 6) ligases; e.g., synthetases, tNRA-ligases, acid-thiol ligases, amide synthases, peptide synthases, cycloligases, carboxylases, DNA-ligases, RNA-ligases, and cyclases.

More specific classes of enzymes include, without limitation, sub-classes of oxidoreductases, transferases, lyases, isomerases, and ligases, as provided below.

Exemplary oxidoreductases include, but are not limited to:

(EC 1.1) oxidoreductases acting on the CH—OH group of donors, and an acceptor;

(EC 1.2) oxidoreductases acting on the aldehyde or oxo group of donors, and an acceptor;

(EC 1.3) oxidoreductases acting on the CH—CH group of donors, and an acceptor;

(EC 1.4) oxidoreductases acting on the CH—NH2 group of donors, and an acceptor;

(EC 1.5) oxidoreductases acting on the CH—NH group of donors, and an acceptor;

(EC 1.6) oxidoreductases acting on NADH or NADPH, and an acceptor;

(EC 1.7) oxidoreductases acting on other nitrogenous compounds as donors, and an acceptor;

(EC 1.8) oxidoreductases acting on a sulfur group of donors, and an acceptor;

(EC 1.9) oxidoreductases acting on a heme group of donors, and an acceptor;

(EC 1.1) oxidoreductases acting on diphenols and related substances as donors, and an acceptor;

(EC 1.11) oxidoreductases acting on a peroxide as acceptor;

(EC 1.12) oxidoreductases acting on hydrogen as donor, and an acceptor;

(EC 1.13) oxidoreductases acting on single donors with incorporation of molecular oxygen, incorporating one or two oxygen atoms;

(EC 1.14) oxidoreductases acting on paired donors, with incorporation or reduction of molecular oxygen, with the donor being 2-oxoglutarate, NADH, NADPH, reduced flavin, flavoprotein, pteridine, iron-sulfur protein, ascorbate;

(EC 1.15) oxidoreductases acting on superoxide radicals as acceptor;

(EC 1.16) oxidoreductases oxidizing metal ions, and an acceptor;

(EC 1.17) oxidoreductases acting on CH or CH2 groups, and an acceptor;

(EC 1.18) oxidoreductases acting on iron-sulfur proteins as donors, and an acceptor;

(EC 1.19) oxidoreductases acting on reduced flavodoxin as donor, and an acceptor;

(EC 1.2) oxidoreductases acting on phosphorus or arsenic in donors, and an acceptor; and (EC 1.21) oxidoreductases acting on X—H and Y—H to form an X—Y bond, and an acceptor; where acceptors for each donor category may include, without limitation: NAD, NADP, heme protein, oxygen, disulfide, quinone, an iron-sulfur protein, a flavin, a nitrogenous group, a cytochrome, dinitrogen, and H+.

Exemplary transferases include, but are not limited to:

(EC 2.1) transferases transferring one-carbon groups;

(EC 2.2) transferases transferring aldehyde or ketonic groups;

(EC 2.3) Acyltransferases;

(EC 2.4) Glycosyltransferases;

(EC 2.5) transferases transferring alkyl or aryl groups, other than methyl groups;

(EC 2.6) transferases transferring nitrogenous groups;

(EC 2.7) transferases transferring phosphorus-containing groups;

(EC 2.8) transferases transferring sulfur-containing groups; and (EC 2.9) transferases transferring selenium-containing groups.

Exemplary hydrolases include, but are not limited to:

(EC 3.1) hydrolases acting on ester bonds;

(EC 3.2) Glycosylases;

(EC 3.3) hydrolases acting on ether bonds;

(EC 3.4) hydrolases acting on peptide bonds (peptidases);

(EC 3.5) hydrolases acting on carbon-nitrogen bonds, other than peptide bonds;

(EC 3.6) hydrolases acting on acid anhydrides;

(EC 3.7) hydrolases acting on carbon-carbon bonds;

(EC 3.8) hydrolases acting on halide bonds;

(EC 3.9) hydrolases acting on phosphorus-nitrogen bonds;

(EC 3.1) hydrolases acting on sulfur-nitrogen bonds;

(EC 3.11) hydrolases acting on carbon-phosphorus bonds;

(EC 3.12) hydrolases acting on sulfur-sulfur bonds; and (EC 3.13) hydrolases acting on carbon-sulfur bonds.

Exemplary lyases include, but are not limited to:

(EC 4.1) Carbon-carbon lyases;

(EC 4.2) Carbon-oxygen lyases;

(EC 4.3) Carbon-nitrogen lyases;

(EC 4.4) Carbon-sulfur lyases;

(EC 4.5) Carbon-halide lyases; and (EC 4.6) Phosphorus-oxygen lyases.

Exemplary isomerases include, but are not limited to:

(EC 5.1) Racemases and epimerases;

(EC 5.2) cis-trans-Isomerases;

(EC 5.3) Intramolecular isomerases;

(EC 5.4) Intramolecular transferases (mutases); and (EC 5.5) Intramolecular lyases.

Exemplary ligases include, but are not limited to:

(EC 6.1) ligases forming carbon-oxygen bonds;

(EC 6.2) ligases forming carbon-sulfur bonds;

(EC 6.3) ligases forming carbon-nitrogen bonds;

(EC 6.4) ligases forming carbon-carbon bonds;

(EC 6.5) ligases forming phosphoric ester bonds; and (EC 6.6) ligases forming nitrogen-metal bonds.

Isozymes (also known as isoenzymes) are enzymes that differ in amino acid sequence but catalyze the same chemical reaction. At some points in a pathway of interest, two or more isozymes may be present. Isozymes may display different kinetic parameters, and/or different regulatory properties.

Enzymes involved in a pathway of interest or associated pathway may also be classified according to the role of the enzyme. Direct involvement enzymes (class 1) in a cell or cell lysate catalyze a reaction in the pathway. It is typical of pathways that such direct enzymes are one of a chain, where a product of a first enzyme is the substrate of a second enzyme, the product of the second enzyme is the substrate of a third enzyme, and so forth, which eventually results in the product of interest. Indirect involvement enzymes (class 2) in a cell or cell lysate react in an associated pathway, usually in the production of a substrate used in the pathway of interest.

Pathways of interest for use in the methods of the described herein will usually comprise at least one enzyme, at least two enzymes, at least three enzymes, at least four enzymes, or more, e.g., between 1 to 50 enzymes, between 1 to 40 enzymes, between 1 to 30 enzymes, between 1 to 20 enzymes, between 1 to 10 enzymes, between 1 to 5 enzymes, between 1 to 2 enzymes, between 2 to 50 enzymes, between 2 to 40 enzymes, between 2 to 30 enzymes, between 2 to 20 enzymes, between 2 to 10 enzymes, between 2 to 5 enzymes, between 2 to 4 enzymes, between 5 to 50 enzymes, between 5 to 40 enzymes, between 5 to 30 enzymes, between 5 to 20 enzymes, between 5 to 10 enzymes, between 5 to 8 enzymes, between 10 to 50 enzymes, between 10 to 40 enzymes, between 10 to 30 enzymes, or between 10 to 20 enzymes, inclusive.

Enzymes in a pathway may be naturally occurring, or modified to optimize a particular characteristic of interest, e.g., substrate specificity, reaction kinetics, solubility, and/or insensitivity to feedback inhibition. In addition, in some cases, the gene expressing the enzyme will be optimized for codon usage within the host cell. In some embodiments, the complete pathway comprises enzymes from a single organism, however such is not required, and combining enzymes from multiple organisms is also contemplated. For some purposes, a pathway may be endogenous to the host cell, but such is also not required, and a complete pathway or components of a pathway may be introduced into a host cell. Where the system is provided in an intact cell, the complete set of enzymes of the pathway of interest can be present in the cell.

It should be appreciated that the genes encoding the enzymes associated with the embodiments described herein can be obtained from a variety of sources. As one of ordinary skill in the art would be aware, homologous genes for these targeted enzymes exist in many species and can be identified by homology searches, for example through a protein BLAST search, available at the NCBI internet site (ncbi (dot)nlm(dot)nih(dot)gov). Genes encoding these enzymes can be PCR-amplified from DNA from any source which contains the given enzyme, for example using degenerate primers, as would be understood by one of ordinary skill in the art. In some embodiments, the gene encoding a given enzyme can be synthetic (artificial), for example, DNA synthesized from sugars, nitrogen-based compounds, phosphates, and other compound/reagents required for DNA synthesis. Any means of obtaining the genes encoding for the enzymes discussed here are compatible with aspects of the embodiments described herein.

Products of the pathway may be stable or relatively labile, but in some instances the final product is sufficiently stable that it can be isolated from the cell, cell lysate, or reaction mixture.

The amount of product produced in a reaction can be measured in various ways, for example, by enzymatic assays which produce a colored or fluorometric product or by high-performance liquid chromatography (HPLC) methods. In certain embodiments, the product is measured utilizing an assay which measures the activity or concentration of the particular product being produced. If the product is a protein, it may be quantified on the RNA or protein level.

One skilled in the art is well aware of methods for introducing polynucleotides into host cells and particularly into *E. coli, Bacillus* and *Pantoea* host cells. General transformation techniques are disclosed in CURRENT PROTOCOLS IN MOLECULAR BIOLOGY Vol. 1, eds. Ausubel et al. John Wiley & Sons Inc, (1987) Chap. 7. and Sambrook, J., et al., MOLECULAR CLONING: A LABORATORY MANUAL, Cold Spring Harbor Laboratory Press (1989). Reference is also made to Ferrari et al., Genetics pgs 57-72 in Hardwood et al. Ed. *BACILLUS*, Plenum Publishing Corp. 1989; Chang et al., (1979) Mol. Gen. Genet. 168:11-15; Smith et al., (1986) Appl. and Env. Microbiol. 51:634 and Potter, H. (1988) Anal Biochem 174:361-373 wherein methods of transformation, including electroporation, protoplast transformation and congression; transduction and protoplast fusion are disclosed. Methods of transformations are particularly preferred. Methods suitable for the maintenance and growth of bacterial cells is well known and reference is made to the Manual of Methods of General Bacteriology, Eds. P. Gerhardt et al., American Society for Microbiology, Washington, D.C. (1981) and T. D. Brock in Biotechnology: A Textbook of Industrial Microbiology 2 ed. (1989) Sinauer Associates, Sunderland Mass.

As used herein, the term "introduced" used in the context of inserting a nucleic acid sequence into a cell, means "transfection," "transformation," or "transduction," and includes reference to the incorporation of a nucleic acid sequence into a eukaryotic or prokaryotic cell where the nucleic acid sequence may be incorporated into the genome of the cell (e.g., chromosome, plasmid, plastid, or mitochondrial DNA), converted into an autonomous replicon, or transiently expressed (for example, transfected mRNA).

As used herein, the terms "transformed," "stably transformed," and "transgenic" used in reference to a cell means the cell has a non-native (heterologous) nucleic acid sequence integrated into its genome or as an episomal plasmid that is maintained through two or more generations.

The transformed host cells are selected based on the phenotype response to a selectable marker which was provided in an insertion DNA construct. In some embodiments the selectable marker may be excised out of the host cell. (Cherepanov et al. (1995) Gene 158:9-14).

Host cells for pathway engineering include a wide variety of heterotrophic and autotrophic microorganisms, including, but not limited to, bacteria, fungi and protozoans. In certain embodiments, host cells include those for which means by which a polypeptide can be directed to a cellular compartment or extracellular compartments are known. In some embodiments, the cell is any type of cell that recombinantly expresses any one or more of the nucleic acids described herein. Such cells include prokaryotic and eukaryotic cells. In some embodiments, the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobac-* terium spp. and *Pantoea* spp. The bacterial cell can be a Gram-negative cell such as an *Escherichia coli* (*E. coli*) cell, or a Gram-positive cell such as a species of *Bacillus*. In other embodiments the cell is a fungal cell such as yeast cells, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Other non-limiting examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, a plant cell, or a mammalian cell. It should be appreciated that some cells compatible with the embodiments described herein may express an endogenous copy of one or more of the genes described herein as well as a recombinant copy. Species of interest include, without limitation, *S. cerevisiae, E. coli, Pseudomonas* species, *Klebsiella* species, and *Synechocystis* species.

Following selection of the appropriate RBS enzyme combination in a particular pathway, the polynucleotides may be introduced into a cell system as separate expression vector or on a single expression vector so as to prepare commercial quantities of that product. The final product may then be isolated. A variety of methodologies well known to the skilled practitioner can be utilized to obtain isolated polypeptides associated with the embodiments described herein. The polypeptide may be purified from cells by immunochromatography, HPLC, size exclusion chromatography, ion exchange chromatography and immune affinity chromatography.

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced over time to prolong the period of time for active synthesis. A reactor may be run in any mode such as batch, extended batch, semi-batch, semi-continuous, fed-batch, and continuous, and which will be selected in accordance with the application purpose.

The reactions may be of any volume, either in a small scale (e.g., usually at least about 1 ml and not more than about 15 ml) or in a scaled up reaction (e.g., where the reaction volume is at least about 15 ml, usually at least about 50 ml, more usually at least about 100 ml, and may be 500 ml, 1000 ml, or greater up to many thousands of liters of volume). Reactions may be conducted at any scale.

Using the strategy described herein, the present inventors have uncovered the optimal RBS-enzyme combination for the synthesis of astaxanthin.

Thus, according to another aspect of the present invention there is provided a method of generating astaxanthin comprising expressing polynucleotides encoding enzymes of an astaxanthin pathway, the polynucleotides comprising:
  (i) a polynucleotide which encodes Phytoene dehydrogenase (crtI) and a first transcriptional regulatory sequence;
  (ii) a polynucleotide which encodes Beta-lycopene cyclase (lcy-B) and a second transcriptional regulatory sequence;
  (iii) a polynucleotide which encodes Beta-carotene ketolase (crtW) and a third transcriptional regulatory sequence;

wherein the first, second and third regulatory sequence are selected such that the expression of the lcy-B and the crtW is greater than a level of expression of the crtI.

The method of the present invention contemplates expression of at least one, at least two, at least three at least four additional polynucleotides encoding enzymes of the astaxanthin pathway.

Additional polynucleotides include:
  (iv) a polynucleotide which encodes Isopentenyl pyrophosphate (idi) and a fourth transcriptional regulatory sequence;
  (v) a polynucleotide which encodes Geranylgeranyl pyrophosphate synthase (crtE) and a fifth transcriptional regulatory sequence;
  (vi) a polynucleotide which encodes Prephytoene pyrophosphate synthase (crtB) and a sixth transcriptional regulatory sequence;
  and
  (vii) a polynucleotide which encodes Beta-carotene hydroxylase (crtZ) and a seventh transcriptional regulatory sequence.

As used herein, the term "astaxanthin" refers to any one of its three stereoisomers (3R,3'R), (3R,3'S) (meso) and (3S,3'S), also known as 3,3'-dihydroxy-β-carotene-4,4'-dione, having a molecular formula $C_{40}H_{52}O_4$.

In order to generate astaxanthin in biological cells, the cells preferably express enzymes of the astaxanthin pathway.

Exemplary enzymes are listed herein below.

Geranylgeranyl Pyrophosphate Synthase (crtE or GGPP Synthase):

The term "crtE" refers to an enzyme which is capable of converting farnesyl diphosphate (FPP) to geranylgeranyl diphosphate GGPP (EC 2.5.1.29). GenBank Accession Nos. of non-limiting examples of crtE are listed below and in Table 15 of U.S. Patent Application No. 20110039299, incorporated herein by reference. A crtE of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to crtE sequences listed herein below as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

Illustrative examples of nucleotide sequences for geranylgeranyl pyrophosphate synthase include but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP 00743052; *Bacillus thuringiensis* serovar *israelensis*, ATCC 35646 sq1563), (CRGGPPS; *Catharanthus roseus*), (NZ_AABF02000074, Locus ZP.sub.-00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MC1276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP.sub.-00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC 007759, Locus YP_461832; *Syntrophus aciditrophicus* SB), and (NC.sub.-006840, Locus YP.sub.-204095; *Vibrio fischeri* ES114). According to a specific embodiment, the GGPP synthase comprises a sequence derived from *Pantoea agglomerans*—GenBank: AAA21260.1 (SEQ ID NO: 62).

Prephytoene Pyrophosphate Synthase (crtB):

As used herein, the term "crtB" refers to the enzyme which converts GGPP to phytoene (EC=2.5.1.32), also known as phytoene synthase. GenBank Accession Nos. of non-limiting examples of crtB are listed in Table 18 of U.S. Patent Application No. 20110039299, incorporated herein by reference. A crtB of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to crtE sequences listed in Table 18 of U.S. Patent Application No. 20110039299 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

According to a specific embodiment, the crtB comprises a sequence derived from *Pantoea agglomerans*—GenBank: AAA21264.1 (SEQ ID NO: 63).

Phytoene Dehydrogenase (crtI):

As used herein, the term "crtI" refers to the enzyme which converts phytoene to lycopene (EC=1.14.99). GenBank Accession Nos. of non-limiting examples of crtI are listed in Tables 17A and 17B of U.S. Patent Application No. 20110039299, incorporated herein by reference. A crtE of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to crtI sequences listed in Tables 17A and 17B of U.S. Patent Application No. 20110039299 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

According to a specific embodiment, the crtI comprises a sequence derived from *Pantoea agglomerans*—GenBank: AAA21263.1 (SEQ ID NO: 64).

Isopentenyl Pyrophosphate Isomerase (idi):

As used herein, the term "idi" refers to the isomerase enzyme which catalyzes the conversion of the relatively un-reactive isopentenyl pyrophosphate (IPP) to the more-reactive electrophile dimethylallyl pyrophosphate (DMAPP). (EC=5.3.3.2). It is also known as Isopentenyl-diphosphate delta isomerase. GenBank Accession Nos. of non-limiting examples of idi are listed in Table 13 of U.S. Patent Application No. 20110039299, incorporated herein by reference. A idi of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to idi sequences listed in Table 13 of U.S. Patent Application No. 20110039299 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

According to a specific embodiment, the idi comprises a sequence derived from *Haematococcus pluvialis*—GenBank: AAC32208.1 (SEQ ID NO: 65).

Beta-Lycopene Cyclase (Lcy-B):

As used herein, the term "lcy-B" refers to the enzyme which catalyzes the conversion of lycopene to carotene. GenBank Accession Nos. of non-limiting examples of lcy-B are listed in Table 23 of U.S. Patent Application No. 20110039299, incorporated herein by reference. A lcy-B of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to lcy-B sequences listed in Table 23 of U.S. Patent Application No. 20110039299 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

According to a specific embodiment, the lcy-B comprises a sequence derived from *Solanum lycopersicum*—GenBank: ABR57232.1 (SEQ ID NO: 66).

Beta-Carotene Hydroxylase (crtZ):

As used herein, the term "crtZ" refers to the enzyme which catalyzes the conversion of carotene to Zeaxanthin and/or the enzyme which catalyzes the conversion of canthaxanthin to astaxanthin (EC 1.14.13). GenBank Accession Nos. of non-limiting examples of crtZ are listed in Table 20 of U.S. Patent Application No. 20110039299, incorporated herein by reference. A crtZ of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to crtZ sequences listed in Table 20 of U.S. Patent Application No. 20110039299 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof.

According to a specific embodiment, the crtZ comprises a sequence derived from *Pantoea ananatis*—Swiss-Prot: P21688.1 (SEQ ID NO: 67).

Beta-Carotene Ketolase (crtW):

As used herein, the term "crtW" refers to the enzyme which catalyzes the conversion of carotene to canthaxantin and/or the enzyme which catalyzes the conversion of zeaxanthin to astaxanthin. GenBank Accession Nos. of non-limiting examples of crtW are listed in Table 19 of U.S. Patent Application No. 20110039299, incorporated herein by reference. A crtW of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to crtW sequences listed in Table 19 of U.S. Patent Application No. 20110039299 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof. According to a specific embodiment, the crtW comprises a sequence derived from *Nostoc sphaeroides*—GenBank: BAB74888.1 (SEQ ID NO: 68).

Preferably, the cells also express 1-deoxyxylulose-5-phosphate synthase (dxs).

As used herein the term "1-deoxyxylulose-5-phosphate synthase (dxs)" refers to the enzyme which catalyzes the condensation of pyruvate and D-glyceraldehyde 3-phosphate to D-1-deoxyxylulose 5-phosphate (DOXP). (EC 2.2.1.7). Exemplary accession numbers include those provided in Table 3 of U.S. Patent Application No. 20040268436, incorporated herein by reference. A dxs of the present invention also refers to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to dxs sequences listed in Table 3 of U.S. Patent Application No. 20040268436 as determined using BlastP software of the National Center of Biotechnology Information (NCBI) using default parameters). The homolog may also refer to a deletion, insertion, or substitution variant, including an amino acid substitution, thereof and biologically active polypeptide fragments thereof. According to a specific embodiment, the dxs comprises a sequence derived from *Escherichia coli*—SwissProt: A7ZX72.1 (SEQ ID NO: 69).

Additional enzymes of the astaxanthin pathway which may also be expressed in the host system are described in U.S. Patent Application No. 20110039299, incorporated herein by reference.

A variety of prokaryotic or eukaryotic cells or eukaryotic cells can be used as host-expression systems to express the polypeptides of the present invention. These include, but are not limited to, microorganisms, such as bacteria transformed with a recombinant bacteriophage DNA, plasmid DNA or cosmid DNA expression vector containing the polypeptide coding sequence; mammalian expression systems such as CHO cells, fungi such as yeast transformed with recombinant yeast expression vectors containing the polypeptide coding sequence; algae and plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequences. Additional host expression systems are further described herein above.

According to a preferred embodiment, the enzymes of the astaxanthin pathway are expressed in bacterial cells.

In one embodiment, the host cell is a bacterial cell such as a gram positive bacteria. In another embodiment the host cell is a gram-negative bacteria. In some preferred embodiments, the term refers to cells in the genus *Pantoea*, the genus *Bacillus* and *E. coli* cells.

As used herein, "the genus *Bacillus*" includes all members known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

As used herein, "the genus *Pantoea*" includes all members known to those of skill in the art, including but not limited to *P. agglomerans, P. dispersa, P. punctata, P. citrea, P. terrea, P. ananas* and *P. sterartii*. It is recognized that the genus *Pantoea* continues to undergo taxonomical reorganization. Thus, it is intended that the genus include species that have been reclassified, including but not limited to such organisms as *Erwinia herbicola*.

The polynucleotide sequences of the present invention are inserted into expression vectors (i.e., a nucleic acid construct) to enable expression of the polypeptides of the astaxanthin pathway in the cells.

The number of enzymes that need to be expressed using expression vectors in a particular cell system will depend on the number of those enzymes which are endogenously expressed in that particular cell system. Thus, for example if a particular cell system endogenously expresses crtW to a sufficient extent, that enzyme may not need to be exogenously expressed using recombinant methods.

The present invention contemplates inserting a polynucleotide sequence encoding one, two, three, four, five, six, seven or eight of the polypeptides of the astaxanthin pathway on a single expression vector. Thus, the expressing of the polypeptides may be effected by introducing a single expression vector encoding all the necessary enzymes or a plurality of vectors encoding various combinations of the polypeptides of the astaxanthin pathway.

The present inventors have found that for optimum expression of astaxanthin, the transcriptional regulatory elements operatively linked to the polynucleotides encoding the components of the astaxanthin pathway should be selected to ensure a particular ratio of expression.

According to a particular embodiment, the expression of both Icy-B and crtW should be manipulated such that their expression level is higher than the level of expression of crtI. Preferably the level of expression of both Icy-B and crtW is at least two times the level of expression of crtI. According to another embodiment, the level of expression of both Icy-B and crtW is at least five times the level of expression of crtI.

According to another embodiment, the level of expression of both Icy-B and crtW is at least ten times the level of expression of crtI. According to another embodiment, the level of expression of both Icy-B and crtW is at least 20 times the level of expression of crtI. According to another embodiment, the level of expression of both Icy-B and crtW is at least 50 times the level of expression of crtI. According to another embodiment, the level of expression of both Icy-B and crtW is at least 100 times the level of expression of crtI.

As used herein, the phrase "transcriptional regulatory element" refers to a sequence of bases operatively linked to the protein coding region of the polynucleotide which controls transcription thereof.

Examples of transcriptional regulatory elements include, but are not limited to a promoter, an enhancer, an mRNA stability effecting sequence and a ribosomal binding site (RBS).

For the purposes of this application, a "promoter" or "promoter region" is a nucleic acid sequence that is recognized and bound by a DNA dependent RNA polymerase during initiation of transcription. The promoter, together with other transcriptional and translational regulatory elements is necessary to express a given gene or group of genes (an operon). The promoter may be a regulatable promoter, such as Ptrc, which is induced by IPTG or a constitutive promoter.

Promoter sequences useful for creating artificial promoters according to the invention include the precursor promoters listed in Table 1 below. All promoters in the table are characterized with respect to the beta-lactamase promoter Pbla and promoter strengths are given in "Pbla-units". (Deuschle et al., EMBO Journal 5(11):2987-2994 (1986)). Further examples of promoters and nucleic acid sequences thereof are provided in U.S. Patent Application No. 20120015849, incorporated herein by reference. In general, promoters useful in the invention include promoter sequences of between 200 to 20 base pairs (bp), preferably 150 to 25 bp, more preferably between 100 to 30 bp and most preferably between 50 to 30 bp upstream from the transcription start site (+1).

Additional promoters useful in the invention are disclosed in Sommer et al., (2000) Microbiol. 146:2643-2653, wherein the sequence of Ptac and variants containing 1 or 2 base pair changes are taught.

TABLE 1

| Promoter | Source | Relative activity |
|---|---|---|
| B-lactamase (bla) | *E. coli* | 1 |
| P-Consensus (con) | Synthetic DNA | 4 |
| PTac1 (Trc) | Hybrid of 2 promoters | 17 |
| PLacUV5 | Mutant of Lac | 3.3 |
| Plac | *E. coli* LacZ gene | 5.7 |
| PL | Phage λ | 37 |
| PA1 | Phage T7 | 22 |
| PA2 | Phage T7 | 20 |
| PA3 | Phage T7 | 76 |
| PJ5 | Phage T3 | 9 |
| PG25 | Phage T3 | 19 |
| PN25 | Phage T3 | 30 |
| PD/E20 | Phage T3 | 56 |
| PH207 | Phage T3 | 55 |

Promoter strength can be quantified using in vitro methods that measure the kinetics of binding of the RNA polymerase to a particular piece of DNA, and also allows the measurement of transcription initiation (Hawley D. K et al., Chapter 3: in: PROMOTERS: STRUCTURE AND FUNCTION. R. L/Rodriguez and M. J. Chamberlin eds. Praeger Scientific. New York). Further, promoter strength can be quantified by linking the promoter to a polynucleotide sequence encoding a detectable protein (e.g. a fluorescent marker), as further described herein below. In vivo methods have been used also to quantify promoter strength. In this case, the approach has been to fuse the promoter to a reporter gene and the efficiency of RNA synthesis measured.

As mentioned, the transcriptional regulatory element may comprise a ribosome binding site (RBS), which are further described herein above.

According to a particular embodiment, the RBS linked to crtI is one which brings about expression of a nucleic acid sequence to at least 60%, at least 70%, at least 80%, at least 90% of the extent as the RBS having a sequence as set forth in SEQ ID NO: 4, 5, 6 or 7 for the same nucleic acid sequence under identical experimental and transcriptional conditions (i.e. in the same cell, for the same time, at the same temperature, with the same promoter etc.).

According to a particular embodiment, the RBS linked to lcyB is one which brings about expression of a nucleic acid sequence to at least 60%, at least 70%, at least 80%, at least 90% of the extent as the RBS having a sequence as set forth in SEQ ID NO: 2 or 3 for the same nucleic acid sequence under identical experimental and transcriptional conditions (i.e. in the same cell, with the same promoter etc.).

According to a particular embodiment, the RBS linked to crtW is one which brings about expression of a nucleic acid sequence to at least 60%, at least 70%, at least 80%, at least 90% of the extent as the RBS having a sequence as set forth in SEQ ID NO: 2 or 3 for the same nucleic acid sequence under identical experimental and transcriptional conditions (i.e. in the same cell, with the same promoter etc.).

One particular combination of sequences contemplated by the present inventors is as follows:

The RBS linked to the polynucleotide sequence encoding idi is one which brings about expression of a nucleic acid sequence to at least 60%, at least 70%, at least 80%, at least 90% of the extent as the RBS having a sequence as set forth in SEQ ID NO: 5 for the same nucleic acid sequence under identical experimental and transcriptional conditions (i.e. in the same cell, with the same promoter etc.).

The RBS linked to the polynucleotide sequence encoding crtE is one which brings about expression of a nucleic acid sequence to at least 60%, at least 70%, at least 80%, at least 90% of the extent as the RBS having a sequence as set forth in SEQ ID NO: 5 for the same nucleic acid sequence under identical experimental and transcriptional conditions (i.e. in the same cell, with the same promoter etc.).

The RBS linked to the polynucleotide sequence encoding crtB is one which brings about expression of a nucleic acid sequence to at least 60%, at least 70%, at least 80%, at least 90% of the extent as the RBS having a sequence as set forth in SEQ ID NO: 3 for the same nucleic acid sequence under identical experimental and transcriptional conditions (i.e. in the same cell, with the same promoter etc.).

The RBS linked to the polynucleotide sequence encoding crtI is one which brings about expression of a nucleic acid sequence to at least 60%, at least 70%, at least 80%, at least 90% of the extent as the RBS having a sequence as set forth in SEQ ID NO: 7 for the same nucleic acid sequence under identical experimental and transcriptional conditions (i.e. in the same cell, with the same promoter etc.).

The RBS linked to the polynucleotide sequence encoding lcy-B is one which brings about expression of a nucleic acid sequence to at least 60%, at least 70%, at least 80%, at least 90% of the extent as the RBS having a sequence as set forth in SEQ ID NO: 2 for the same nucleic acid sequence under identical experimental and transcriptional conditions (i.e. in the same cell, with the same promoter etc.).

The RBS linked to the polynucleotide sequence encoding crtW is one which brings about expression of a nucleic acid sequence to at least 60%, at least 70%, at least 80%, at least 90% of the extent as the RBS having a sequence as set forth in SEQ ID NO: 3 for the same nucleic acid sequence under identical experimental and transcriptional conditions (i.e. in the same cell, with the same promoter etc.).

The RBS linked to the polynucleotide sequence encoding crtZ is one which brings about expression of a nucleic acid sequence to at least 60%, at least 70%, at least 80%, at least 90% of the extent as the RBS having a sequence as set forth in SEQ ID NO: 6 for the same nucleic acid sequence under identical experimental and transcriptional conditions (i.e. in the same cell, with the same promoter etc.).

Another exemplary combination of sequences is as follows:

The RBS linked to the polynucleotide sequence encoding idi is one which brings about expression of a nucleic acid sequence to at least 60%, at least 70%, at least 80%, at least 90% of the extent as the RBS having a sequence as set forth in SEQ ID NO: 6 for the same nucleic acid sequence under identical transcriptional conditions (i.e. in the same cell, with the same promoter etc.).

The RBS linked to the polynucleotide sequence encoding crtE is one which brings about expression of a nucleic acid sequence to at least 60%, at least 70%, at least 80%, at least 90% of the extent as the RBS having a sequence as set forth in SEQ ID NO: 3 for the same nucleic acid sequence under identical experimental and transcriptional conditions (i.e. in the same cell, with the same promoter etc.).

The RBS linked to the polynucleotide sequence encoding crtB is one which brings about expression of a nucleic acid sequence to at least 60%, at least 70%, at least 80%, at least 90% of the extent as the RBS having a sequence as set forth in SEQ ID NO: 7 for the same nucleic acid sequence under identical experimental and transcriptional conditions (i.e. in the same cell, with the same promoter etc.).

The RBS linked to the polynucleotide sequence encoding crtI is one which brings about expression of a nucleic acid sequence to at least 60%, at least 70%, at least 80%, at least 90% of the extent as the RBS having a sequence as set forth in SEQ ID NO: 5 for the same nucleic acid sequence under identical experimental and transcriptional conditions (i.e. in the same cell, with the same promoter etc.).

The RBS linked to the polynucleotide sequence encoding lcy-B is one which brings about expression of a nucleic acid sequence to at least 60%, at least 70%, at least 80%, at least 90% of the extent as the RBS having a sequence as set forth in SEQ ID NO: 2 for the same nucleic acid sequence under identical experimental and transcriptional conditions (i.e. in the same cell, with the same promoter etc.).

The RBS linked to the polynucleotide sequence encoding crtW is one which brings about expression of a nucleic acid sequence to at least 60%, at least 70%, at least 80%, at least 90% of the extent as the RBS having a sequence as set forth in SEQ ID NO: 2 for the same nucleic acid sequence under identical experimental and transcriptional conditions (i.e. in the same cell, with the same promoter etc.).

The RBS linked to the polynucleotide sequence encoding crtZ is one which brings about expression of a nucleic acid sequence to at least 60%, at least 70%, at least 80%, at least 90% of the extent as the RBS having a sequence as set forth in SEQ ID NO: 2 for the same nucleic acid sequence under identical experimental and transcriptional conditions (i.e. in the same cell, with the same promoter etc.).

As mentioned herein above, the present inventors further contemplate expressing DXS. Preferably, the RBS linked to the polynucleotide sequence encoding DXS is one which brings about expression of a nucleic acid sequence to at least 60%, at least 70%, at least 80%, at least 90% of the extent as the RBS having a sequence as set forth in SEQ ID NO: 6 for the same nucleic acid sequence under identical experimental and transcriptional conditions (i.e. in the same cell, with the same promoter etc.).

Using the methods described herein to express astaxanthin, the present inventors obtained bacterial cells (E. coli cells) comprising more than 2 mg/g cell dry weight of astaxanthin, comprising more than 3 mg/g cell dry weight of astaxanthin, comprising more than 4 mg/g cell dry weight of astaxanthin, comprising more than 5 mg/g cell dry weight of astaxanthin, comprising more than 10 mg/g cell dry weight of astaxanthin.

Transformed cells are cultured under effective conditions, which allow for the expression of high amounts of the recombinant polypeptides. Effective culture conditions include, but are not limited to, effective media, bioreactor, temperature, pH and oxygen conditions that permit protein production. An effective medium refers to any medium in which a cell is cultured to produce the recombinant polypeptides of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Following a predetermined time in culture, recovery of the astaxanthin is effected and spectrophotometric analysis or analysis by HPLC can be performed.

The phrase "recovering astaxanthin" used herein refers to collecting the whole fermentation medium containing the astaxanthin and need not imply additional steps of separation or purification.

For collecting carotenoids and/or astaxanthin from bacterial cells or a culture solution following culturing, for example, bacterial cells may be separated from a culture solution by a centrifugation or the like and extracted therefrom by an appropriate organic solvent. Examples of such an organic solvent include methanol, ethanol, isopropyl alcohol, acetone, methyl ethyl ketone, methyl isobutyl ketone, dichloromethane, chloroform, dimethyl formamide and dimethyl sulfoxide. Among them acetone is preferred. Further, separation and purification into higher purity may be achieved by utilizing a liquid chromatography or the like. Liquid chromatography may be based on a separation principle of ion exchange, hydrophobic interaction, and molecular sieve, for example. Reverse-phase chromatography and normal-phase chromatography are preferred. Alternatively, extraction from cells may be conducted by supercritical fluid extraction.

Alternatively, after completion of culturing, bacterial cells may be separated from the culture solution by way of centrifugal separation, decantation, or filtration, for example. The obtained bacterial cells are added with water to be rendered a slurry having a convenient viscosity. In order to prevent decomposition of carotenoids such as astaxanthin, an appropriate additive may be added to the slurry. Examples of such an additive include, but are not limited to, antioxidants such as ascorbic acid. Thereafter, the prepared slurry is homogenized with the use of a grinder using glass beads or zirconia beads or high-pressure homogenizer, and dried for use later. A preferred drying method is spry drying.

The bacterial cells may directly be added to feeds for farm-raised fish or the like.

Alternatively, they may be extracted from a polar solvent or the like as describe above before use. Cell bodies remaining after extraction of carotenoids such as astaxanthin and containing little pigments can be used as ideal supply sources of proteins and vitamins in poultry raising.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND METHODS

Strains, Media and Reagents:

The bacterial strain used for cloning and construct assembly was *E. coli* DH5α unless stated otherwise. For the purification of plasmid DNA, cells were cultured in LB media supplemented with suitable antibiotics at 37° and DNA was purified form culture using standard kits (Qiagen, Germany). All primers were synthesized by Sigma Aldrich, Israel. Detailed description of primers can be found in Table 2, herein below.

TABLE 2

| | |
|---|---|
| RBS construction | |
| RBSX 1$^{st}$ forward | GAATTCGCGGCCGCACTAGTTAATAGAA ATAATTTTGTTTAACTTTA - SEQ ID NO: 10 |
| RBS A | GATGGTGATGATGCATTCCAAACCTCCT TAAAGTTAAACAAAAT - SEQ ID NO: 11 |
| RBS B | GATGGTGATGATGCATCTCAGTACCTCC TCATTTTGTTTAAAGTTAAACAAAAT - SEQ ID NO: 12 |
| RBS C | GATGGTGATGATGCATTCTTGCCTCTTA ACTTTAAAGTTAAACAAAAT - SEQ ID NO: 13 |
| RBS D | GATGGTGATGATGCATCGCCGCCGGTCC TGCTTATAAAGTTAAACAAAAT - SEQ ID NO: 14 |
| RBS E | GATGGTGATGATGCATCTTCCCCCTGCG AATAAAGTTAAACAAAAT - SEQ ID NO: 15 |
| RBS Z | GATGGTGATGATGCATCAGTGTATGGTG TAAAGTTAAACAAAAT - SEQ ID NO: 16 |
| Cap Cassette construction | |
| F-primer + NheI (linker site) | GCTAGCGTTGATCGGGCACGTAAGAG - SEQ ID NO: 17 |
| V1.0-R primer | GGCCACATGTCTGCAGCGGCCGCGCTA GC - SEQ ID NO: 18 |
| V1.1-R primer | GCGCTCGAGCGGCCGCGCTAGCTTATTA CG -- SEQ ID NO: 19 |
| Cap Overhang addition | GCTAGCGTTGATCGGGCACGTAAG AG - SEQ ID NO: 20 |
| Pviv primers | |
| KS f NotI + PstI | gcggccgcctgcagGGCGGTAATACGGT TATCCA - SEQ ID NO: 21 |
| Ks T1-T2 R | CTCTCGCTTAGTAGTTAGACGTCCGACG TTGGAGTCCACGTTCT - SEQ ID NO: 22 |
| KS T1-T2 pENTR11 F | AGAACGTGGACTCCAACGTCGGACGTCT AACTACTAAGCGAGAG - SEQ ID NO: 23 |
| T1-T2 pENTER R | actagtgaattcGCAACGAACAGGTCAC TATC - SEQ ID NO: 24 |
| Barcode | |
| Bar RBS A F | CTCGAG AAA GTCGAC CTGCAG GCA GGGCGGTAATACGGTTA - SEQ ID NO: 25 |
| Bar RBS b F | CTCGAGGAG GTCGAC CTGCAG GCAG GGCGGTAATACGGTTA - SEQ ID NO: 26 |
| Bar RBS C F | CTCGAG TAT GTCGAC CTGCAG GCA GGGCGGTAATACGGTTA - SEQ ID NO: 27 |

TABLE 2-continued

| Name | Sequence |
|---|---|
| Bar RBS D F | CTCGAG CAC GTCGAC CTGCAG GCA GGGCGGTAATACGGTTA - SEQ ID NO: 28 |
| Bar RBS E F | CTCGAG AGG GTCGAC CTGCAG GCA GGGCGGTAATACGGTTA - SEQ ID NO: 29 |
| Bar RBS Z F | CTCGAG GGT GTCGAC CTGCAG GCA GGGCGGTAATACGGTTA- SEQ ID NO: 30 |
| pRBS R | TTACTTGTACAGCTCGTCCATGC - SEQ ID NO: 31 |

Primers for amplification of fluorescence protein from Tsien collection

| Name | Sequence |
|---|---|
| His-Dye Forward | ATGCATCATCACCATCACCACGTGAGCA AGGGCGAGGAG - SEQ ID NO: 32 |
| Dye-Cap-Reverse | CTCTTACGTGCCCGATCAACGCTAGCTT ACTTGTACAGCTCGTCCATGC - SEQ ID NO: 33 | primers for eliminating PstI site in mcherry (352)

| Name | Sequence |
|---|---|
| G353A Forward | CCAGGACTCCTCCCTGCAAGACGGCGAG TT -SEQ ID NO: 34 |
| G353A Reverse | AACTCGCCGTCTTGCAGGGAGGAGTCCT GG - SEQ ID NO: 35 |

Haematococcus pluvialis isopentenyl pyrophosphate (ipiHp1)

| Name | Sequence |
|---|---|
| His-ipiHp1 Forward | ATGCATCATCACCATCACCACCTTCGTT CG TTGCTCAGAGG - SEQ ID NO: 36 |
| ipiHp1 Reverse | ATCACATCAACGAAGCGTGA GCTAGCG TTGATCGGGCACGTAAGAG - SEQ ID NO: 37 | eliminating 314 PstI site

| Name | Sequence |
|---|---|
| ipiHp1 T315C Forward | CACAAGTTCCTACCACATCAGCCCGCAG GCC - SEQ ID NO: 38 |
| ipiHp1 T315C Reverse | GGCCTGCGGGCTGATGTGGTAGGAACTT GTG - SEQ ID NO: 39 |
| ipiHp1 C435T Forward | GTGGACGAACACCTGCTGTAGCCACCCT TT SEQ ID NO: 40 |
| ipiHp1 C435T Reverse | AAAGGGTGGCTACAGCAGGTGTTCGTCC AC SEQ ID NO: 41 |

Pantoea agglomerans geranylgeranyl pyrophosphate synthase (CrtE)

| Name | Sequence |
|---|---|
| His-CrtE | ATGCATCATCACCATCACCACTATCCGT TTATAAGGACAGCC SEQ ID NO: 42 |
| CrtE Reverse | CTCTTACGTGCCCGATCAACGCTAGCTT AACTGACGGCAGCGAGT SEQ ID NO: 43 |

Pantoea agglomerans prephytoene pyrophosphate synthase (crtB)

| Name | Sequence |
|---|---|
| His-CrtB Forward | ATGCATCATCACCATCACCACAAT AATCCGTCGTTACTCAA SEQ ID NO: 44 |
| CrtB Reverse | CTCTTACGTGCCCGATCAACGCTAG CTTATGCCGGTACTGCCGGGC SEQ ID NO: 45 |

Pantoea agglomerans phytoene dehydrogenase (crtl)

| Name | Sequence |
|---|---|
| His-CrtI Forward | ATGCATCATCACCATCACCACAAAC CAACTACGGTAATTGGT SEQ ID NO: 46 |
| CrtI Reverse | CTCTTACGTGCCCGATCAACGCTAGC TCATATCAGATCCTCCAGCA SEQ ID NO: 47 | primers for eliminating PstI site in CrtI (478, 889)

| Name | Sequence |
|---|---|
| CrtI(G480T) Forward | GCACCTCAACTGGCGAAACTTCAGGCAT GGA SEQ ID NO: 48 |
| CrtI(G480T) Reverse | TCCATGCCTGAAGTTTCGCCAGTTGAGG TGC - SEQ ID NO: 49 |
| CrtI (G891T) Forward | CGGTTAAGCAGTCCAACAAACTTCAGAC TAA - SEQ ID NO: 50 |
| CrtI (G891T )Reverse | TTAGTCTGAAGTTTGTTGGACTGCTTAA CCG - SEQ ID NO: 51 |

Solanum lycopersicum beta-lycopene cyclase (LCY-B)

| Name | Sequence |
|---|---|
| His-LcY-B Forward | ATGCATCATCACCATCACCACGATACTT TGTTGAAAACCCC - SEQ ID NO: 52 |
| LcY-B Reverse | CTCTTACGTGCCCGATCAACGCTAGCTC ATTCTTTATCCTGTAACAAATTG - SEQ ID NO: 53 | primers for eliminating PstI site in Lyc-B (278)

| Name | Sequence |
|---|---|
| Lyc-B (A282G) Forward | GCTGTGGTTGGTGGTGGCCCTGCGGGAC TT - SEQ ID NO: 54 |
| Lyc-B (A282G) Reverse | AAGTCCCGCAGGGCCACCACCAACCACA GC - SEQ ID NO: 55 | primers for eliminating NsiI site in Lyc-B (1313)

| Name | Sequence |
|---|---|
| LycB (A1317G) Forward | CAAGAAGGTTCTTTGATGCGTTCTTTGA CT - SEQ ID NO: 56 |
| LycB (A1317G) Reverse | AGTCAAAGAACGCATCAAAGAACCTTCT TG - SEQ ID NO: 57 |

Nostoc sp beta-carotene ketolase (CrtW)

| Name | Sequence |
|---|---|
| His-crtW | ATGCATCATCACCATCACCACGTTCAGT GTCAACCATCATC - SEQ ID NO: 58 |
| CrtW Reverse | CTCTTACGTGCCCGATCAACGCTAGCTT ATAAAGATATTTTGTGAGCTTCAGG - SEQ ID NO: 59 |

Erwinia uredovora beta-carotene hydroxylase (crtZ)

| Name | Sequence |
|---|---|
| His CrtZ forward | ATGCATCATCACCATCACCACTTGT GGATTTGGAATGCCC - SEQ ID NO: 60 |
| CrtZ Reverse | CTCTTACGTGCCCGATCAACGCTAG CTTATTACTTCCCGGATGCGGG - SEQ ID NO: 61 |

PCR reactions were performed using Phusion polymerase (Finnzymes, Finland). Cloning procedures were designed using Clone manager professional suite (Scientific & Educational Software, State Line, US-PA). Restriction enzymes were purchased from New England BioLabs (Beverly, US-MA) unless stated otherwise. Ligation reactions were performed using T4 DNA ligase (Fermentas, Lithuania). Detailed description of all of the equipment, reagents, suppliers and relevant catalogue numbers can be found in Table 3, herein below.

TABLE 3

| LB BROTH | Conda 1231 | Standard culture |
|---|---|---|
| M9 | | |
| Kanamycin | Sigma Aldrich Israel K4378-5G | Standard culture |
| Chloramphenicol | Sigma Aldrich Israel C0378-5G | Standard culture |
| Ampicillin | Sigma Aldrich Israel A0166-5G | Standard culture |
| Oligonucleotides | Sigma Aldrich Israel | PCR |
| Phusion | Finnzymes F-530S | PCR |
| dNTP Set | Fermentase R0181 | PCR |
| Zymoclean Gel DNA Recovery Kit | Zymo Research D4001 | PCR cleanup |
| ATP | Sigma Aldrich Israel A2383-5G | PNK phosphorilation cloning |
| T4 DNA Ligase | Fermentase EL0014 | Ligation Cloning |
| T4 Polynu-cleotide Kinase | NEB M0201L | Self ligation cloning |
| Alkaline Phosphatase, Calf Intestinal (CIP) | NEB M0290L | Cloning |
| EcoRI-HF | NEB R3101L | Cloning |
| SpeI | NEB R0133L | Cloning |
| NsiI | NEB R0127L | Cloning |
| NheI-HF | NEB R3131L | Cloning |
| XhoI | NEB R0146L | Cloning |
| SalI-HF | NEB R3138L | Cloning |
| PstI-HF | NEB R3140L | Cloning |
| PciI | NEB R0655L | Cloning |
| QIAprep Spin Mini-prep Kit (50) | 27104 | Miniprep |

"No-Background" Assembly: General Cloning Scheme:

A "No-Background" assembly strategy was developed with the aim to facilitate the serial assembly of multiple DNA sequences into a single construct. All DNA constructs were generated according to the methodology described below. "No-Background" assembly adheres to the principles described in "Idempotent Vector Design for Standard Assembly of Biobrick" (worldwide webdspacedotmitdotedu/handle/1721.1/21168), also known as the BioBrick standard. In addition to preserving the main features described in the BioBrick system, an additional feature was added which eliminates the need to screen and validate that intermediate constructs were correctly assembled throughout a multi-step assembly process.

The key feature of the method is the concatenation of a chloramphenicol resistance marker ($Cm^R$): a constitutive promoter followed by a Chloramphenicol Acetyltransferase coding sequence, to each of the DNA sequences designated for assembly. The $Cm^R$ cassette is paired to the DNA sequence using PCR overlap extension prior to the assembly process. When the target DNA sequence (now paired with the $Cm^R$) is assembled into a vector using a standard restriction-ligation process, only clones that were properly assembled are able to form colonies on agar plates supplemented with Cm.

Since the resistance cassette is flanked by restriction sites (FIG. 1), it can be easily removed when preparing the vector for the next assembly cycle. In this manner, it is possible to perform multiple assembly rounds while using a single resistance marker. A general scheme of the "No-Background" Assembly strategy is described in FIG. 1.

Construction of Chloramphenicol Resistance Cassette:

The resistance cassette contains a constitutive promoter and a chloramphenicol acetyltransferase gene as the resistance marker. The cassette was amplified via PCR using the pSB3C5 plasmid as a template (BioPart: BBa_P1004). Restriction sites were added so the resistance cassette is flanked by NheI site at the 5' and XhoI and PciI sites in its 3' (Table 1, herein above).

Pairing Resistance Cassette with a Target Sequence:

Each of the DNA sequences designated for assembly were joined with the Cm resistance cassette using a standard assembly PCR reaction. An insulator sequence containing an NsiI site was added upstream to the target sequence while the sequence <u>GCTAGC</u>GTTGATCGGGCACGTAAGAG (SEQ ID NO: 1) was added downstream. The latter sequence contains a NheI (underlined) site and a homology region of 20 bp to the beginning of the Cm resistance cassette (bold). The homology sequence enables overlap extension PCR between the target sequence and the cassette, effectively enabling to pair the sequence of interest with the resistance marker. The PCR reaction was conducted using a sequence specific forward primer and a generic reverse primer (Cm-R, Table 1). The resulting PCR product (i.e. the target sequence concatenated to the resistance cassette) was gel purified and may be sub-cloned into a vector or digested directly with suitable restriction enzymes.

Choosing a Compact Set of RBS Sequences to Span Expression Space:

To find a small set of RBS sequences that span a large fraction of the expression space, the forward engineered RBS series experimentally analyzed in the work of Salis et al., Nature Biotechnology 27, 946-950 (2009) was used. First, the expected translation rate of each of the RBS sequences attached to various genes was computationally calculated [Sans Lab: The Ribosome Binding Site Calculator. at salisdotpsudotedu/software/]. RBS sequences were chosen whose strength seems to be the least affected by the downstream sequence. From this limited set 5 RBS sequences were picked which spanned the largest expression space experimentally [Sans et al., Nature Biotechnology 27, 946-950 (2009)]. These RBS sequences were:

8 (RBS-A):
(SEQ ID NO: 2)
AGGAGGTTTGGA

1 (RBS-B):
(SEQ ID NO: 3)
AACAAAATGAGGAGGTACTGAG

17 (RBS-C):
(SEQ ID NO: 4)
AAGTTAAGAGGCAAGA

27 (RBS-D):
(SEQ ID NO: 5)
TTCGCAGGGGAAG

20 (RBS-E):
(SEQ ID NO: 6)
TAAGCAGGACCGGCGGCG

"Dead-RBS" (RBS-F):
(SEQ ID NO: 7)
CACCATACACTG

Flanking "Insulator" Sequences:

Since the sequences flanking the RBS can affect expression levels, insulator sequences—a constant sequence of ~20 bp located upstream and downstream of each of the RBS were used. Such isolation sequences have been previously reported to be effective in reducing the effect of flanking sequences in the case of promoters. The upstream insulator sequence was taken to be 19 base pairs, not natively found in *E. coli*: TAATAGAAATAATTTTGTT-TAACTTTA (SEQ ID NO: 8) while the downstream insulator sequence was taken to be ATGCATCATCACCAT-CACCAC (SEQ ID NO: 9), a sequence coding for a 6His-tag.

RBS Modulation of a Target ORF:

In order to clone a target coding sequence for RBS modulation, it was first amplified via PCR and paired to Cm resistance marker as described above. Once the target gene was paired to the resistance cassette, the product was ligated into a linearized BlueScript KS+ plasmid. The target ORF was then excised from the plasmid using either NsiI and PciI (non-barcoded assembly), or NsiI and XhoI. The resulting fragment, containing the target sequence and the resistance marker was then assembled upon a RBS backbone vector (RBS backbone) containing a RBS sequence upstream to the insertion site. The resulting construct contains the desired RBS followed by the target ORF and the resistance marker, as described in FIG. 2.

pNiv—the Backbone Plasmid:

The backbone plasmid was constructed using Bluescript Ks+ as a base. The LacZ gene was eliminated and the original multiple cloning site was swapped with a new site that contains EcoRI, SpeI and PciI restriction sites (FIG. 3). In order to minimize leaky gene expression throughout the assembly the process, the strong RRNB terminator (amplified by PCR using pENTER11-Gateway as a template) was inserted upstream of the new cloning site. All DNA sequence modifications were accomplished by using the PCR overhang extension method.

pNiv:RBS-A-YFP to pNiv:RBS-F-YFP—Plasmid Set:

Each of the six core RBS sequences and the flanking insulator sequences were purchased as synthesized oligodeoxynucleotides. Each of the core RBS sequences was flanked with the up- and downstream insulation sequences and fused to a YFP reporter gene in an assembly PCR reaction (see Table 1). The resulting six RBS-YFP reaction products (namely, RBS-A to RBS-F), were restricted and ligated into the backbone plasmid pNiv to yield the six designated plasmids—pNiv:[RBS-A to RBS-F]-YFP—see FIG. 4.

Expression Plasmids:

The DNA assembly process was conducted on the pNiv backbone plasmids which contain no designated promoter. Once the assembly process was completed, the resulting product was sub-cloned into an expression plasmid—pSB4K5:Ptac. This plasmid was derived from pSB4K5, a BioBrick standard vector with low copy pSC101 replication origin (BioPart: BBa_I50042) and kanamycin antibiotic resistance marker (BioPart: BBa_P1003). LacIq Brick (BioPart: BBa_C0012) and a Tac promoter (BioPart: BBa_K301000) were assembled on pSB4K5 upstream to the multiple cloning site using standard assembly methods to yield pSB4K5:Ptac (FIG. 5).

Experimental Measurements of RBS Expression Modulation Using Flow Cytometry:

In order to quantify the effect of the RBS sequence on the expression level in-vivo, a YFP reporter gene was placed upstream to each of the RBS sequence on a pSB4K5:Ptac plasmid using the cloning strategies described previously. *E. coli* MG1655 cells were transformed with the pSB4K5:Ptac-[RBS-A to RBS-F]-YFP plasmids and incubated at 37° C. in minimal media supplemented with 0.2% glucose until mid exponential phase (OD=~0.3). Fluorescence was quantified using BD LSR II Flow Cytometer. A blue laser (488 nm) and a 530±30 nm emission filter were used to measure YFP fluorescence and a yellow laser (560 nm) and a 610±20 nm emission filter were used to measure mCherry fluorescence. ~100,000 cells were recorded in each experiment (FIGS. 6A-D). Correlations between predicted RBS strength to experimental measurements are illustrated in FIG. 7.

pNiv-RBS Mixture Preparation:

Each of the six pNiv-RBS-YFP plasmids was separately digested with NsiI and PciI, removing YFP from the backbone vector. Digestion products were treated with Calf Intestinal Alkaline Phosphatase (CIP) and gel purified. An equimolar mix of the six resulting linearized vectors, each differing only in the RBS sequence upstream to the cloning site was prepared. This vector mixture (pRBS mix) was used to perform one-tube combinatorial assembly with any target (FIG. 8).

Combinatorial Assembly of RBS Mixture:

For any coding sequence of interest, the coding sequence was cloned as described above. In order to combinatorially pair the coding sequence with the RBS set, the coding sequence was sub-cloned into the linearized pRBS vector mixture. This resulted in a mixture of ligation products: all containing the same coding sequence but with a variety of RBS (RBS-A to RBS-F) sequences upstream (FIG. 8).

Assembling a RBS-modulated synthetic operon: The resulting library, containing a mixture of constructs, all with an identical coding sequence but with a variety of RBS sequences upstream (RBS-A to RBS-F) can be used either as a vector or as an insert. First, by restricting the mixture using NheI and PciI, the resistance cassette is removed and the plasmid library can be used as a vector into which more RBS modulated coding sequences are assembled. Alternatively, by digesting the mixture with SpeI and PciI, it is possible to excise the coding sequence (along with the upstream RBS) and use it as an insert for further assembly rounds.

In order to assemble a library of operons—where each variant contains the same combination of genes but with a different combination of RBS, the RBS modulated mixture for each of the desired genes was constructed as described above. Iterative assembly steps were then performed, where at each step an additional RBS modulated coding sequence was added along the operon. At every step, the product of the previous round was digested with NheI and PciI as shown in FIG. 9, removing the Cm resistance cassette. The reaction product was treated with CIP and gel purified. The purified product, a linearized vector without Cm resistance, serves as a vector in the next assembly step.

To assemble an additional RBS modulated coding sequence to the operon, the RBS modulated mixture of the designated insert was digested using SpeI and PciI, resulting in a DNA fragment which contains a mixture of RBS sequences upstream to the coding sequence and the resistance cassette. This fragment was ligated into the operons library (already harboring the first RBS modulated coding sequences). This assembly process results in a combinatorial mixture RBS modulated coding sequences, where each variant has a distinct RBS composition upstream to the coding sequences. The library was transformed into *E. coli* DH5α and plated on LB agar plates supplemented with Cm. The resistance cassette which was paired to the last incorporated gene ensured that only constructs which contain the newly added RBS modulated sequence will continue for further assembly rounds.

Plasmid DNA from the newly constructed operon library was recovered from the plate by scraping the colonies directly from the plate and extracting the plasmids encoding for the operons library. Therefore, by repeating this process for N rounds, where in each round an additional RBS modulated coding sequence was added to the combinatorial operon library, the present inventors sequentially assembled a combinatorial mixture of plasmids containing the same N coding sequences in a pre-defined order and driven by a varying combination of the six RBS.

Barcoded RBS Mixture—Approach:

Since the operons library of RBS modulated coding sequences is built in a combinatorial manner, it is required to sequence all of the RBS sequences across the entire operon in order of determine the RBS composition of a specific clone. To facilitate this process, and eliminate the need to sequence all of RBS spread across an operon, the present inventors assigned a 3 base pair barcode sequence to each RBS. These barcodes enable them to easily determine the complete RBS composition of each clone using a single sequencing reaction at the 3' end of stacked barcodes as described in FIG. 10.

The barcodes are computed as follows: each RBS (A-F) was assigned a number (1-6) which was then encoded in a 2-letter DNA code. A given 2-letter code word ($b_1 b_2$=AT, for example) maps to a particular number by the formula $b_1+4*b_2$, where $b_1$ and $b_2$ are numeric values assigned to the bases of the code word (see table below). For the present example, AT becomes 0+4*2=8.

TABLE 4

| Base | Numeric Value |
|---|---|
| A | 0 |
| G | 1 |
| T | 2 |
| C | 3 |

A third base was added as a check-base. This base was computed from the previous two bases as follows: b3=(b1+5*b2) % 4, where '%' represents the modulus operator. This check-base allows detection of any single base mutation or sequencing error. Table 5 below provides the barcode values for each RBS. Note that, though only 6 RBS were used here, one can potentially encode up to 16 RBS total using a 3 bp scheme. The approach is also scalable to much higher library sizes with a logarithmically scaled increase in code length.

TABLE 5

| | Code [with Check-Base] | Numeric Value |
|---|---|---|
| RBS-A | AAA | 0 |
| RBS-B | GAG | 1 |
| RBS-C | TAT | 2 |
| RBS-D | CAC | 3 |
| RBS-E | AGG | 4 |
| RBS-F | GGT | 5 |

Addition of Barcodes to the pNiv-RBS Set:

Each of the six pNiv plasmid containing an RBS-YFP insert (RBS-A to RBS-F) served as template for a PCR reaction in which barcode bases and restriction sites were added using designated primers (Table 2). XhoI restriction site was added upstream of the barcode area while SalI and PstI sites were added downstream. Each of the six pNiv-RBS-YFP-barcoded plasmids was separately digested with NsiI and XhoI, removing the YFP coding sequence. An equimolar mixture of the six resulting linearized vectors (namely, pRBS-Barcode mixture) was prepared as described herein above.

Single Tube Combinatorial Assembly Using Barcoded RBS Mixture:

The use of the barcoded RBS plasmid set relies on the same logic as described above except a few technical changes resulting from the different use of restriction enzymes. The target coding sequence is first cloned as described above and digested using NsiI and XhoI. The insert is ligated with the pRBS-Barcode mixture and transformed in DH5α cells. A schematic description of the process is described below in FIG. 11.

For simplicity the assembly process shown in FIG. 11 contains only two coding sequences assembled into an operon, each with a specific RBS. The process can be iteratively extended by additional assembly cycles. Moreover, a combinatorial RBS mixture can be used instead of specific ones.

Subcloning into an Expression Plasmid:

After the assembly process was completed, the resulting operon was sub-cloned into an expression vector containing a designated promoter. This was obtained by using the designated restriction sites flanking the final operon. Moreover, since the expression plasmid had a resistance marker differing from the Cm marker paired to the operon, while selecting with both antibiotics, only positive colonies can grown while clones transformed with either the self ligated expression plasmid or the library donor plasmid could not.

RGB—Tricolor Reporter System

Bacterial Strains and Growth Conditions:

The bacterial strain used for the cloning and construct assembly process was E. coli DH5α. For fluorescence measurements plasmids were transformed into E. coli K12 MG1655 which were grown in minimal media supplemented with 0.2% glucose and chloramphenicol (34 ug/ml) at 37 degrees.

Genes:

mYFP, mCFP and mCherry were amplified by PCR from the following plasmids pRSETB-YFP, pRSETB-CFP and pRSETB-mcherry. PstI restriction site on mCherry gene was eliminated by introducing a single silent mutation (see Table 1).

Assembly Process:

mYFP, mCherry and CFP were first paired with resistance cassette as explained above. The operon was assembled using the barcoded RBS set as described in section above. pRBS-mYFP-barcode1 was digested with NheI & XhoI restriction enzymes in order to use it as a vector, while pRBS-mCherry-barcode2 was digested with SpeI & SalI in order to use it as an insert. These two restriction products were ligated resulting in new product pRBS-mYFP-RBS-mCherry-barcode2-barcode1. This product was digested as a vector with NheI & XhoI, while pRBS-mCFP-barcode3 was digested as insert with SpeI and SalI, the resulting products were ligated to assemble the following operon in pNiv plasmid: pRBS-mYFP-mcherry-mCFP-barcode3-barcode2-barcode1. Next, the operon was digested sub-cloned into an expression plasmid as described above.

Measurements of RGB Fluorescence Library

Automated Fluorescence Measurements:

Cells were grown in a 96 well plate containing M9+0.2% Glucose in an automated robotic platform (Evoware II, Tecan). Every 15 minutes the plate was transferred by a robotic arm into a multi-well fluorimeter (Infinite M200-pro, Tecan). In each measurement OD was sampled at 600 nm, mCherry was sampled by excitation at 587 nm and emission measurement at 620 nm and YFP was sampled by excitation at 520 nm and emission measurement at 555 nm.

Data Analysis:

Raw data of OD and fluorescence was background corrected by subtracting wells containing medium with no cells.

Because of the large required dynamic range, it was not possible to analyze wells with weak RBS at low bacteria concentrations. Therefore, the present inventors chose to work at mid to late exponential phase. Cells were analyzed around an OD600 value of 0.1 as measured by the plate reader after media subtraction, equivalent to OD600 of ~0.2 with standard 1 cm path length. For each measurement point, the activity was defined as the increase of fluorescence during a time window of one hour centered at the measurement's time divided by the average OD measured during that time:

$$A(T) = \frac{F(T+\tau) - F(T-\tau)}{\int_{T-\tau}^{T+\tau} OD(t)\,dt}$$

where A is the RBS activity, F is the fluorescence measurement and τ=30 minutes. The result reflects the increase in fluorescence during one hour divided by the number of cells. Mean activity was calculated by averaging over 5 measurements around OD 0.1 for each sample:

$$\tilde{A} = \frac{\sum_{i=1}^{t=5} A(t_i)}{5}$$

All analysis steps were performed using custom Haskell software.

Fluorescence Microscopy of Bacterial Colonies:

Fluorescence images were taken using a Nikon ECLIPSE E800 microscope equipped with a Nikon Intensilight (C-HGFIE) for illumination. Chroma filter cubes set was used to image fluorescence proteins: mCherry (excitation filter 530-560 nm, emission filter 590-650, 30 ms exposure), cyan fluorescent protein (mCFP) (excitation filter 426-446 nm, emission filter 460-500 nm. 60 ms exposure) and yellow fluorescent protein (mYFP) (excitation filter 490-510 nm, emission filter 520-550 nm, 800 ms exposure). Images were captured with a camera and N1S-Elements BR3.22 software. Different channels were overlaid to give the figures shown.

Translational Coupling:

The translation of sequential genes within a single operon was previously shown to be dependent on upstream genes, a phenomenon termed translational coupling. Specifically, the expression level of a gene is modulated by the expression level of the gene preceding it. Translational coupling was observed for various operons in E. coli as well as other prokaryotes. While translational coupling has been known for many years, it is only crudely quantified and its underlying mechanism is under debate.

Figure 16A:
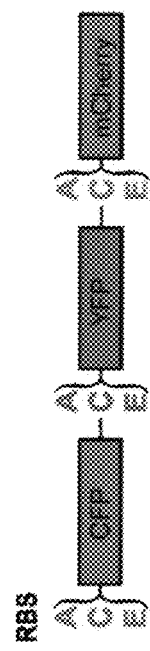
Figure 16B:
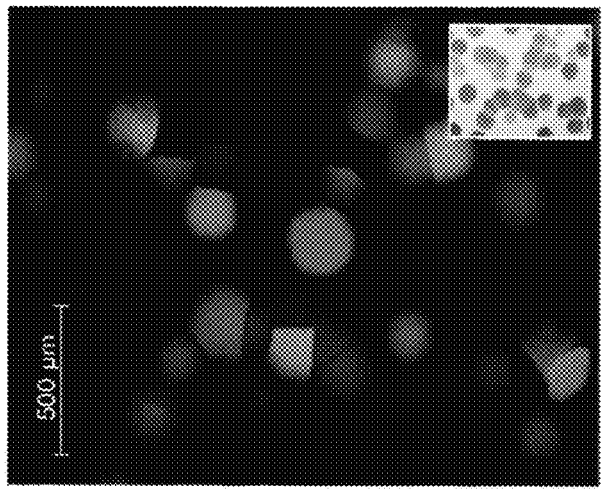
Figure 16C:
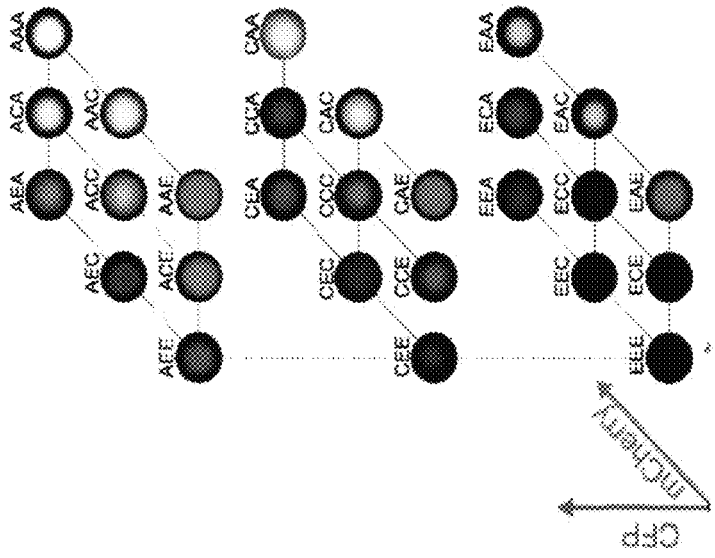
Figure 16D:
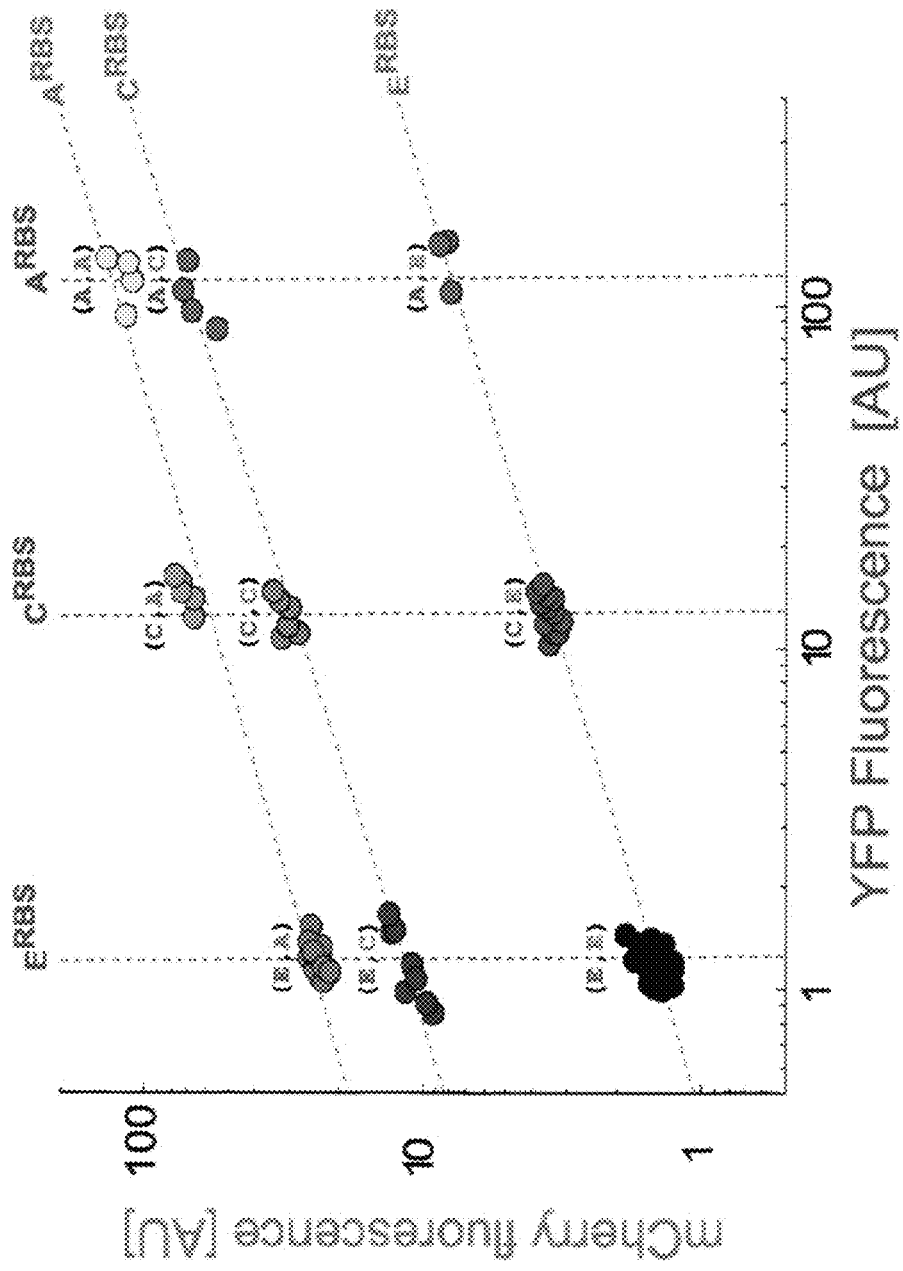

The RGB grid shown in FIG. 16D demonstrates translational coupling. YFP's fluorescence depends only on the strength of the RBS controlling it, while mCherry's fluorescence depends both on the RBS controlling it and on YFP's fluorescence. To further analyze this effect the present inventors utilized clones where YFP was controlled by one of the six RBS (A-F) while mCherry was controlled by either a weak RBS (E), a moderate strength RBS (C), or a strong RBS (A). The fluorescence of YFP and mCherry for each library variant was then measured, and plotted against each other. The grid obtained (FIG. 13) clearly demonstrates translational coupling: The first gene (i.e. YFP) expression level depends only on the strength of the RBS controlling it; the stronger the RBS used, the greater is the YFP fluorescence measured. In contrast, the second gene (mCherry) expression level depends both on the RBS controlling it, and on the RBS controlling the first gene. That is, clones that share the same RBS for mCherry show different mCherry fluorescence level depending on the upstream YFP expression level. Cross fluorescence was ruled out as the cause for such an effect: clones containing a single fluorescence protein (either YFP or mCherry) do not give a signal at the reciprocal fluorescence channel even for high levels of expression. The maximal translation enhancement of mCherry by YFP expression level in the present system was found to be ~6 fold. The dependency between YFP and mCherry levels shows a linear dependence in log space (FIG. 13). Linear regression gives a slope of ~⅓ (95% confidence intervals 0.26-0.36).

RBS Modulation of the Carotenoid Biosynthesis Pathway
Bacterial Strains and Growth Conditions:

The bacterial strain used for the cloning and construct assembly process was E. coli DH5α. For carotenoids expression, transformed cells were grown in LB media supplemented with chloramphenicol (34 ug/ml) at 37 degrees.

Genes for the Astaxanthin Biosynthetic Pathway

For the astaxanthin synthesis the following genes were used:

Geranylgeranyl pyrophosphate synthase (crtE) from *Pantoea agglomerans*—GenBank: AAA21260.1 (SEQ ID NO: 62).

Prephytoene pyrophosphate synthase (crtB) from *Pantoea agglomerans*—GenBank: AAA21264.1 (SEQ ID NO: 63).

Phytoene dehydrogenase (crtI) from *Pantoea agglomerans*—GenBank: AAA21263.1 (SEQ ID NO: 64).

Isopentenyl pyrophosphate (idi) from *Haematococcus pluvialis*—GenBank: AAC32208.1 (SEQ ID NO: 65).

Beta-lycopene cyclase (lcy-B) from *Solanum lycopersicum*—GenBank: ABR57232.1 (SEQ ID NO: 66).

Beta-carotene hydroxylase (crtZ) from *Pantoea ananatis*—Swiss-Prot: P21688.1 (SEQ ID NO: 67).

Beta-carotene ketolase (crtW) from *Nostoc sphaeroides*—GenBank: BAB74888.1 (SEQ ID NO: 68).

1-deoxyxylulose-5-phosphate synthase (dxs) from *Escherichia coli*—Swiss-Prot: A7ZX72.1 (SEQ ID NO: 69).

CtrZ was synthesized by using assembly PCR, the primers for the assembly PCR were calculated using Johnson Lab Oligo maker (34). The restriction sites EcoRI, SpeI, NsiI, NheI, PstI and PciI were eliminated from the listed genes by introducing silent mutations.

Assembly Process:

idi,crtE,crtB,crtI,lcy-B,crtW,crtZ and dxs were amplified by PCR and then paired with resistance cassette as explained above. RBS was added to each gene as described above. The library was assembled in an iterative process according to the order of the genes along the biosynthetic pathway. The complete operon was subcloned into an expression plasmid as described.

Carotenoid Analysis
Carotenoid Extraction:

E. coli cells carrying a plasmid with the biosynthetic genes of the carotenoid pathway were grown in suspension cultures in shake flasks containing 100 ml of LB medium. Cultivation was carried out in 37° C. 20 ml samples were withdrawn from the culture after 48 hours and cells were harvested by centrifugation. Cell pellet was washed with cold water and carotenoids were extracted by vigorous shaking with acetone (20 ml). Insoluble components of the extract were removed by centrifugation (15,000 g) and supernatant was transferred into a glass round-bottom flask and was evaporated using a rotary evaporator. Dried extract was re-solvated in 1.5 ml acetone and 50-ul samples were taken for HPLC analysis.

Carotenoid Analysis by HPLC:

HPLC analysis was performed on Jasco platform with high pressure mixing installed with a Borwin software, P4987 pumps and a MD-915 photodiode array detector. Samples were analyzed by injecting 50 ul on a YMC pack ODS-A column (250×4.6 mm, 5 um, 12 nm). Solvent A: 75% aqueous methanol, Solvent B: ethylacetate. Solvent flow rate of 0.6 ml/min was used with the following gradient: 15-85% of B (0-24 min), 85% (24-30 min), 85-15% (30-34 min), 15% (34-745 40 min). The spectra of the eluted carotenoids were recorded online with the photodiode array detector (300-900 nm). Carotenoid compounds were identified by co-chromatography with authentic standard compounds and by analysis of their UV-Vis spectra. For the quantification of the carotenoid compounds the integrated peak areas were compared to those of authentic standards. The concentration of the standard solutions was determined spectrophotometrically (Jasco V-570 instrument)(35). For additional identification, the peaks isolated by HPLC were collected and directly injected into a mass-spectrometer (Micromass Quattro Ultima tandem quadruple instrument equipped with a Z-spray ESI interface and Waters Masslynx v4.1 software). The corresponding masses were analyzed from obtained full-scan (ESI(+), m/z 100-1000) mass spectra(36).

Photos:

Pictures of colonies appearing in FIGS. 16A-D were taken using a binocular microscope (WILD M8; Heerbrugg, Switzerland) under visible light.

Results

Figure 15B:
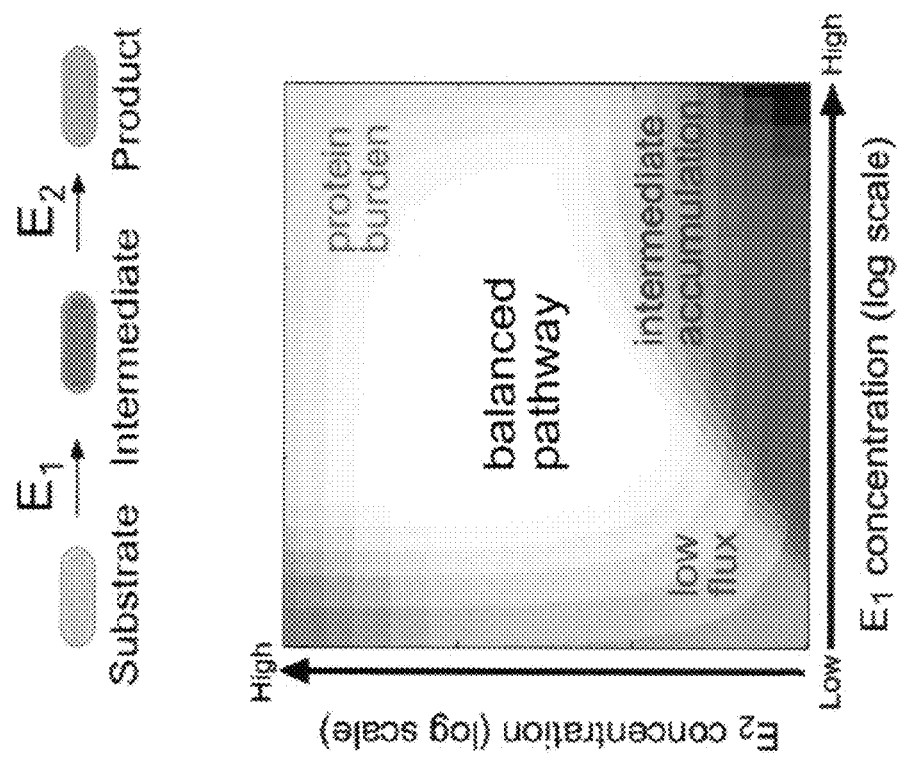
Figure 15D:
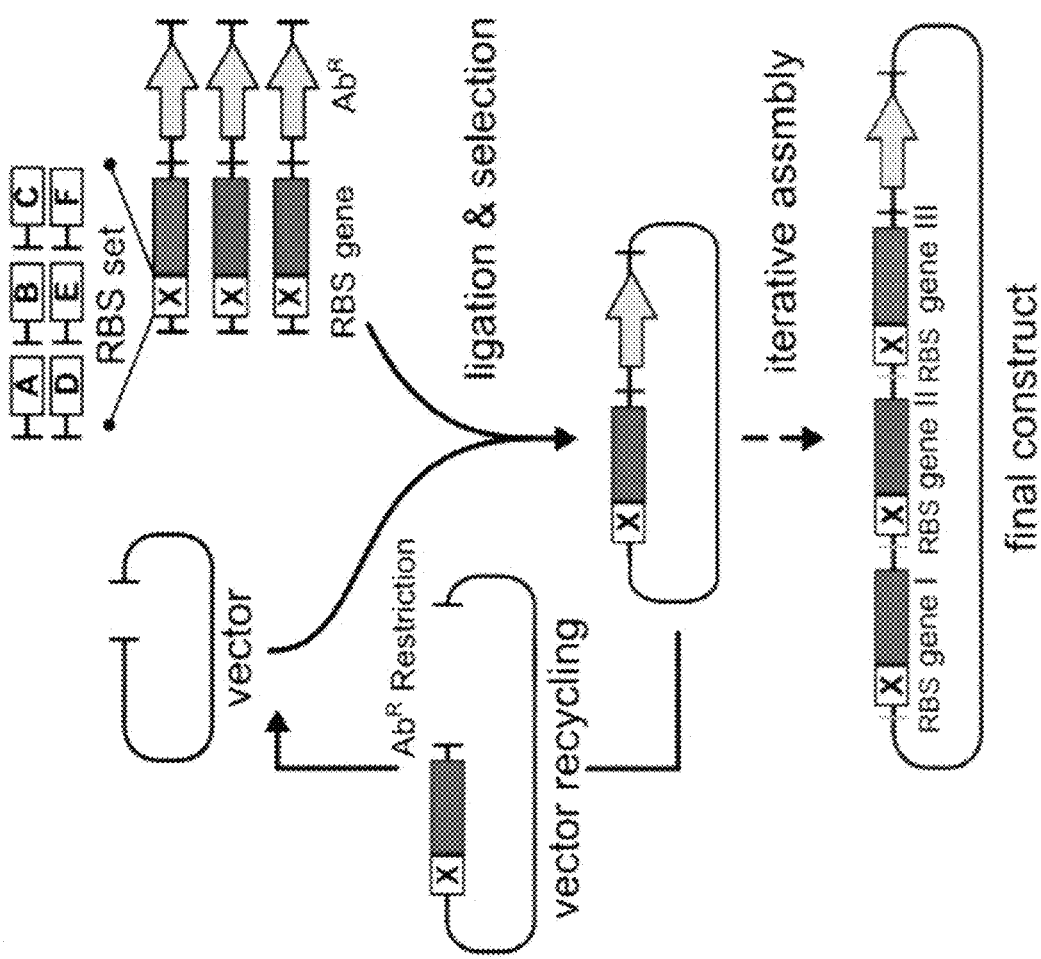
Figure 15C:
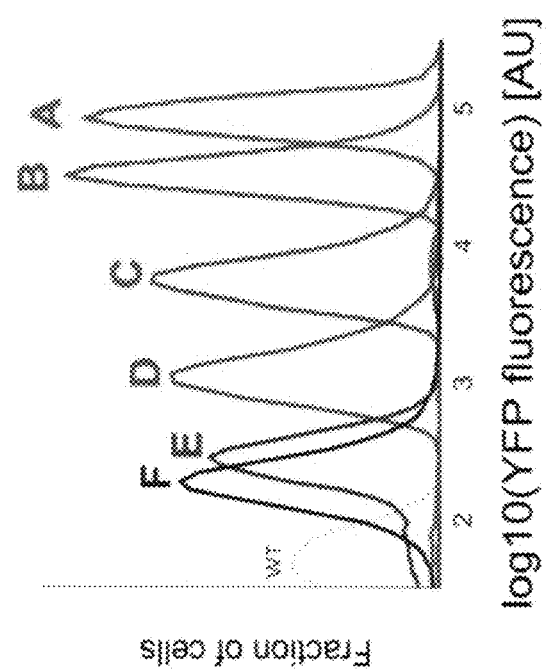

Six RBS sequences that had previously been found to span several orders of magnitude of protein expression were selected (9,14) (FIG. 15B). First, the effect of different RBS sequences was quantified on expression levels by placing each sequence upstream to an YFP reporter and measuring the fluorescence signal using flow cytometry (15). The six RBS were labeled 'A' to 'F' in descending order by expression level. As shown in FIG. 15C, a small set of RBS can span several orders of magnitude of protein expression levels. Next, the present inventors asked whether it was possible to use this small set of RBS sequences to assemble a library that spans the expression space of several genes simultaneously. A library of operons was generated where each member contains the same genes but under the translational regulation of different RBS sequences. To achieve this, the present inventors combinatorially paired each of the genes of interest with a set of RBS sequences and assembled these RBS-gene constructs to generate a library of synthetic operons (15).

An augmented BioBrick (16) cloning strategy was developed to facilitate the assembly process. Genetic parts were iteratively assembled using a positive-selection procedure that bypasses the need for time-consuming screening steps (15). Briefly, a chloramphenicol (Cm) resistance cassette was joined to all the genetic parts that were to be assembled. In each step, an additional genetic part was inserted into the construct (FIG. 15D) while the resistance cassette enabled a direct selection for properly assembled constructs. The vector was then "recycled" for the next iteration by excising the resistance cassette (FIG. 15D). This strategy bypasses intermediate screening steps and enables fast and efficient operon construction. The resulting library of operons was then transformed into cells and screened for a desired phenotype.

Inference of the RBS composition of a specific clone was performed by sequencing a barcode located at the 3' UTR of the gene (as described in the Materials and methods). The barcode was generated during the assembly process by iteratively concatenating a short identifying sequence onto the 3' UTR of the operon. Each genetic variant in the library contains a distinct barcode sequence from which the RBS composition of all the genes in the operon can be inferred in a single sequencing reaction.

To test whether RBS combinatorics can span a multi-dimensional expression space, a tri-color reporter system was constructed. CFP, YFP and mCherry were each randomly paired with three representatives of the present RBS set (RBS sequences 'A', 'C' and 'E') and assembled together into an operon. The resulting operon library therefore contained $3^3=27$ genetic variants, where each member contains the three genes in the same order but under the regulation of different RBS sequences (FIG. 16A). Upon transformation, colonies display distinct color patterns (FIG. 16B), resulting from differential expression of the fluorescent reporters. The observed color space indicates that the combinatorial assembly of RBS sequences can significantly modulate expression level of multiple genes within the operon (FIG. 16C). The present inventors verified that the different colors observed were attributed to different combinations of RBS sequences by sequencing sample clones and quantifying their fluorescence levels (15). In addition, the present inventors measured the fluorescence levels of an operon consisting of YFP and mCherry and found a grid of nine clusters as shown in FIG. 16D. Each cluster contains clones which have identical RBS. Moreover, the spread of the clusters demonstrates that RBS modulation spans ~100 fold in each dimension of the expression space. Notably, the expression level of YFP is dependent only on the RBS sequence regulating it. All colonies with the same RBS upstream to YFP (located first in this operon) are aligned vertically and show a similar level of protein expression. However, mCherry fluorescence (located downstream to YFP) depends both on its RBS and on the expression level of the upstream gene (FIG. 16D). Coupling over more than two orders of magnitude with a power law exponent of ~¼ was found, showing an expression increases by about 2 fold for every 10 fold increase in the expression of the upstream gene (FIG. 16D). The dependency is not due to cross fluorescence (15), but is rather a manifestation of translational coupling (17) between adjacent genes in the operon.

The present tri-color reporter system demonstrates that a combinatorial assembly of RBS sequences can span a large fraction of the expression space. The present inventors asked what the effect of such expression modulation had on the operation of a metabolic pathway. To address this question, seven genes which compose the carotenoid biosynthesis pathway were cloned into E. coli. The end product of this exogenous metabolic pathway is astaxanthin, a high value xanthophylls (19) known for its potent antioxidant properties. To explore the effect of combinatorial RBS modulation on the biosynthesis of astaxanthin in E. coli, each of the genes of the carotenoid pathway was randomly paired with the RBS set and assembled into a synthetic operon (FIG. 17A). The resulting library contains $6^7$ genetic variants in a single test tube. As shown in FIG. 17B, the transformed E. coli colonies display a large variety of colors and intensities. The color pattern of each colony is attributed to differential accumulation of distinct carotenoid intermediates, each having a unique color.

The RBS composition of sampled clones was determined by sequencing and the carotenoid profile was analyzed using HPLC (15). FIG. 17C shows that clones differing in their RBS composition exhibit diverse carotenoid profiles. Some clones accumulate mainly a single product while others produced significant levels of a variety of carotenoids. Using the present combinatorial RBS approach, it was possible to increase astaxanthin productivity to 2.6 mg/g of cell dry weight, about twice as much as previously produced in *E. coli*. Moreover, incorporating dxs—a gene feeding into the carotenoid pathway—into the operon under RBS-modulation increased astaxanthin production to 5.8 mg/g of cell dry weight. This represents a 4-fold increase in astaxanthin production over the best previously reported results.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. P. Lu, C. Vogel, R. Wang, X. Yao, E. M. Marcotte, Absolute protein expression profiling estimates the relative contributions of transcriptional and translational regulation, *Nat Biotechnol* 25, 117-124 (2006).
2. M. Scott, C. W. Gunderson, E. M. Mateescu, Z. Zhang, T. Hwa, Interdependence of Cell Growth and Gene Expression: Origins and Consequences, *Science* 330, 1099-1102 (2010).
3. D. Na, T. Y. Kim, S. Y. Lee, Construction and optimization of synthetic pathways in metabolic engineering, *Current Opinion in Microbiology* 13, 363-370 (2010).
4. E. Dekel, U. Alon, Optimality and evolutionary tuning of the expression level of a protein, *Nature* 436, 588-592 (2005).
5. M. Koffas, Engineering metabolism and product formation in *Corynebacterium glutamicum* by coordinated gene overexpression, *Metabolic Engineering* 5, 32-41 (2003).
6. D. J. Pitera, C. J. Paddon, J. D. Newman, J. D. Keasling, Balancing a heterologous mevalonate pathway for improved isoprenoid production in *Escherichia coli*, *Metabolic Engineering* 9, 193-207 (2007).
7. B. R. Glick, Metabolic load and heterologous gene expression, *Biotechnol. Adv* 13, 247-261 (1995).
8. K. Hammer, I. Mijakovic, P. R. Jensen, Synthetic promoter libraries—tuning of gene expression, *Trends in Biotechnology* 24, 53-55 (2006).
9. H. M. Salis, E. A. Mirsky, C. A. Voigt, Automated design of synthetic ribosome binding sites to control protein expression, *Nat Biotechnol* 27, 946-950 (2009).
10. H. H. Wang et al., Programming cells by multiplex genome engineering and accelerated evolution, *Nature* 460, 894-898 (2009).
11. B. F. Pfleger, D. J. Pitera, C. D. Smolke, J. D. Keasling, Combinatorial engineering of intergenic regions in operons tunes expression of multiple genes, *Nat. Biotechnol* 24, 1027-1032 (2006).
12. A. H. Babiskin, C. D. Smolke, A synthetic library of RNA control modules for predictable tuning of gene expression in yeast, *Mol Syst Biol* 7 (2011), doi: 10.1038/msb.2011.4.
13. K. E. McGinness, T. A. Baker, R. T. Sauer, Engineering Controllable Protein Degradation, *Molecular Cell* 22, 701-707 (2006).
14. D. Baker et al., Engineering Life: Building a FAB for Biology, *Scientific American* 294, 44-51 (2006).
15. Materials and methods are available as supporting material on Science Online. 16. R. P. Shetty, D. Endy, T. F. Knight, Engineering BioBrick vectors from BioBrick parts, *J Biol Eng* 2, 5 (2008).
17. Translational coupling during expression of the tr . . . [Genetics. 1980]—PubMed result (available at worldwidewebdotncbidotnlmdotnih(dot)gov/pubmed/6162715).
18. L. Løvdok et al., A. Levchenko, Ed. Role of Translational Coupling in Robustness of Bacterial Chemotaxis Pathway, *PLoS Biol* 7, e1000171 (2009).
19. F. X. Cunningham, E. Gantt, Elucidation of the Pathway to Astaxanthin in the Flowers of *Adonis aestivalis*, *THE PLANT CELL ONLINE* 23, 3055-3069 (2011).
20. X.-G. Zhu, E. de Sturler, S. P. Long, Optimizing the distribution of resources between enzymes of carbon metabolism can dramatically increase photosynthetic rate: a numerical simulation using an evolutionary algorithm, *Plant Physiol* 145, 513-526 (2007).
21. J. Holatko et al., Metabolic engineering of the L-valine biosynthesis pathway in *Corynebacterium glutamicum* using promoter activity modulation, *Journal of Biotechnology* 139, 203-210 (2009).
22. K. Lemuth, K. Steuer, C. Albermann, Engineering of a plasmid-free *Escherichia coli* strain for improved in vivo biosynthesis of astaxanthin, *Microbial Cell Factories* 10, 29 (2011).
23. DSpace@MIT: Idempotent Vector Design for Standard Assembly of Biobricks (available at dspacedotmitdotedu/handle/1721.1/21168).
24. R. M. Horton, H. D. Hunt, S. N. Ho, J. K. Pullen, L. R. Pease, Engineering hybrid genes without the use of restriction enzymes: gene splicing by overlap extension, *Gene* 77, 61-68 (1989).
25. H. M. Salis, E. A. Mirsky, C. A. Voigt, Automated design of synthetic ribosome binding sites to control protein expression, *Nature Biotechnology* 27, 946-950 (2009).
26. Salis Lab: The Ribosome Binding Site Calculator (available at salisdotpsudotedu/software/).
27. BIOFAB Data Access Client (available at /biofabdotjbeidotorg/services/studio/dac/).
28. J. H. Davis, A. J. Rubin, R. T. Sauer, Design, construction and characterization of a set of insulated bacterial promoters, *Nucleic Acids Research* 39, 1131-1141 (2010).
29. N. C. Shaner, P. A. Steinbach, R. Y. Tsien, A guide to choosing fluorescent proteins, *Nature Methods* 2, 905-909 (2005).
30. G. Baughman, M. Nomura, Localization of the target site for translational regulation of the L11 operon and direct evidence for translational coupling in *Escherichia coli*, *Cell* 34, 979-988 (1983).
31. L. Løvdok et al., A. Levchenko, Ed. Role of Translational Coupling in Robustness of Bacterial Chemotaxis Pathway, *PLoS Biology* 7, e1000171 (2009).

32. D. Schümperli, K. McKenney, D. A. Sobieski, M. Rosenberg, Translational coupling at an intercistronic boundary of the *Escherichia coli* galactose operon, *Cell* 30, 865-871 (1982).
33. G. Rex, B. Surin, G. Besse, B. Schneppe, J. E. McCarthy, The mechanism of translational coupling in *Escherichia coli*. Higher order structure in the atpHA mRNA acts as a conformational switch regulating the access of de novo initiating ribosomes, *J. Biol. Chem.* 269, 18118-18127 (1994).
34. R. Rydzanicz, X. S. Zhao, P. E. Johnson, Assembly PCR oligo maker: a tool for designing oligodeoxynucleotides for constructing long DNA molecules for RNA production, *Nucleic Acids Research* 33, W521-W525 (2005).
35. G. Britton, vol. Vol. 1B: Spectroscopy (1995), pp. 13-62.
36. F. L. Chu, L. Pirastru, R. Popovic, L. Sleno, Carotenogenesis Up-regulation in Scenedesmus sp. Using a Targeted Metabolomics Approach by Liquid Chromatography—High-Resolution Mass Spectrometry, *Journal of Agricultural and Food Chemistry* 59, 3004-3013 (2011).

What is claimed is:

1. A kit comprising a plurality of isolated polynucleotide sequences encoding enzymes of the astaxanthin pathway comprising:
   (i) a polynucleotide which encodes Phytoene dehydrogenase (crtI) operatively linked to a first ribosome binding site (RBS);
   (ii) a polynucleotide which encodes Beta-lycopene cyclase (lcy-B) operatively linked to a second RBS;
   (iii) a polynucleotide which encodes Beta-carotene ketolase (crtW) operatively linked to a third RBS;
   (iv) a polynucleotide which encodes Isopentenyl pyrophosphate (idi) operatively linked to a fourth RBS;
   (v) a polynucleotide which encodes Geranylgeranyl pyrophosphate synthase (crtE) operatively linked to a fifth RBS;
   (vi) a polynucleotide which encodes Prephytoene pyrophosphate synthase operatively linked to a sixth RBS; and
   (vii) a polynucleotide which encodes Beta-carotene hydroxylase (crtZ) operatively linked to a seventh RBS,
   wherein the second RBS and the third RBS enhance expression of an operatively linked fluorescent reporter polypeptide sequence in a vector within a suitable host cell at least five times more than the first RBS enhances expression of said operatively linked fluorescent reporter polypeptide sequence in the same position of said vector in said host cell, as measured by flow cytometry.

2. The kit of claim 1, wherein said second RBS and said third RBS enhance expression of the operatively linked fluorescent reporter polypeptide sequence ten times more than the first RBS enhances expression of said fluorescent reporter polypeptide sequence which is operatively linked thereto, as measured by flow cytometry.

3. The kit of claim 1, wherein the sequence of the first RBS set forth in SEQ ID NO: 4, 5, 6 or 7;
   wherein the sequence of said second RBS is set forth in SEQ ID NO: 2 or 3;
   wherein the sequence of said third RBS is set forth in SEQ ID NO: 2 or 3.

4. The kit of claim 3, wherein the sequence of said fourth RBS is set forth in SEQ ID NO: 5;
   wherein the sequence of said fifth RBS is set forth in SEQ ID NO: 5;
   wherein the sequence of said sixth RBS is set forth in SEQ ID NO: 3;
   wherein the sequence of said first RBS is set forth in SEQ ID NO: 7;
   wherein the sequence of said second RBS is set forth in SEQ ID NO: 2;
   wherein the sequence of said third RBS is set forth in SEQ ID NO: 3; and wherein the sequence of said seventh RBS is set forth in SEQ ID NO: 6.

5. The kit of claim 1, further comprising:
(viii) a polynucleotide encoding a deoxyxylulose-5-phosphate synthase (DXS) operatively linked to an eighth RBS.

6. The kit of claim 5, wherein said eighth RBS is set forth in SEQ ID NO: 6.

7. The kit of claim 1, wherein said plurality of polynucleotide sequences are comprised in a single expression vector.

8. The kit of claim 1, wherein said plurality of polynucleotide sequences are comprised in a plurality of expression vectors.

9. The kit of claim 1, wherein said plurality of polynucleotide sequences comprise the sequence as set forth in SEQ ID NO: 8 upstream of each of said RBS.

10. A bacterial cell comprising:
(i) a polynucleotide which encodes Phytoene dehydrogenase (crtI) operatively linked to a first ribosome binding site (RBS);
(ii) a polynucleotide which encodes Beta-lycopene cyclase (lcy-B) operatively linked to a second RBS;
(iii) a polynucleotide which encodes Beta-carotene ketolase (crtW) operatively linked to a third RBS;
(iv) a polynucleotide which encodes Isopentenyl pyrophosphate (idi) operatively linked to a fourth RBS;
(v) a polynucleotide which encodes Geranylgeranyl pyrophosphate synthase (crtE) operatively linked to a fifth RBS;
(vi) a polynucleotide which encodes Prephytoene pyrophosphate synthase operatively linked to a sixth RBS; and
(vii) a polynucleotide which encodes Beta-carotene hydroxylase (crtZ) operatively linked to a seventh RBS,
wherein the second RBS and the third RBS enhance expression of an operatively linked fluorescent reporter polypeptide sequence in a vector within a suitable host cell at least five times more than the first RBS enhances expression of said operatively linked fluorescent reporter polypeptide sequence in the same position of said vector in said host cell, as measured by flow cytometry.

* * * * *